(12) United States Patent
Stenkamp et al.

(10) Patent No.: US 7,524,862 B2
(45) Date of Patent: Apr. 28, 2009

(54) ALKYNE COMPOUNDS WITH MCH ANTAGONISTIC ACTIVITY AND MEDICAMENTS COMPRISING THESE COMPOUNDS

(75) Inventors: Dirk Stenkamp, Biberach (DE); Stephan Georg Mueller, Warthausen (DE); Philipp Lustenberger, Warthausen (DE); Thorsten Lehmann-Lintz, Ochsenhausen (DE); Gerald Juergen Roth, Biberach (DE); Klaus Rudolf, Warthausen (DE); Marcus Schindler, Biberach (DE); Leo Thomas, Biberach (DE); Ralf Lotz, Schemmerhofen (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 462 days.

(21) Appl. No.: 11/104,914

(22) Filed: Apr. 13, 2005

(65) Prior Publication Data

US 2005/0267115 A1 Dec. 1, 2005

Related U.S. Application Data

(60) Provisional application No. 60/563,688, filed on Apr. 20, 2004.

(30) Foreign Application Priority Data

Apr. 14, 2004 (DE) .................. 10 2004 017 932

(51) Int. Cl.
A61K 31/47 (2006.01)
A61K 31/44 (2006.01)
C07D 215/38 (2006.01)
C07D 491/02 (2006.01)
C07D 405/00 (2006.01)

(52) U.S. Cl. .............. 514/313; 514/314; 514/317; 514/322; 514/337; 514/338; 514/339; 546/113; 546/159; 546/199; 546/273.4; 546/283.1

(58) Field of Classification Search .............. 546/283.1, 546/159, 193, 199, 273.4; 549/401; 514/305, 514/313, 314, 317, 322, 337, 338, 339
See application file for complete search history.

(56) References Cited

U.S. PATENT DOCUMENTS

| | | | | |
|---|---|---|---|---|
| 6,090,810 | A * | 7/2000 | Klein et al. | 514/252.01 |
| 6,262,269 | B1 * | 7/2001 | Hayes et al. | 546/159 |
| 6,366,268 | B1 | 4/2002 | Forrest et al. | |
| 6,388,081 | B1 * | 5/2002 | Hayes et al. | 506/15 |
| 2002/0052383 | A1 | 5/2002 | Bakthavatchalam et al. | |

FOREIGN PATENT DOCUMENTS

| EP | 0 237 678 A1 | 9/1987 |
|---|---|---|
| EP | 1 283 199 A1 | 2/2003 |
| JP | 04054118 | 2/1992 |
| JP | 2000086603 | 3/2000 |
| WO | WO 98/38156 | 9/1998 |
| WO | WO 99/02497 A2 | 1/1999 |
| WO | WO 99/29674 | 6/1999 |
| WO | WO 00/05223 | 2/2000 |
| WO | WO 00/06153 | 2/2000 |
| WO | WO 00/49005 | 8/2000 |
| WO | WO 01/02344 | 1/2001 |
| WO | WO 01/21577 | 3/2001 |
| WO | WO 01 55066 A2 | 8/2001 |
| WO | WO 01/82925 | 8/2001 |
| WO | WO 02 04433 A2 | 1/2002 |
| WO | WO 02/06245 A1 | 1/2002 |
| WO | WO 02 28182 A1 | 4/2002 |
| WO | WO 02/051809 A1 | 7/2002 |
| WO | WO 02/057233 A1 | 7/2002 |
| WO | WO 02/092068 | 11/2002 |
| WO | WO 03 013247 A1 | 2/2003 |
| WO | WO 03/014111 A1 | 2/2003 |
| WO | WO 03/018579 A1 | 3/2003 |
| WO | WO 03/032980 A1 | 4/2003 |
| WO | WO 03/033476 A1 | 4/2003 |
| WO | WO 03/035055 | 5/2003 |
| WO | WO 03/045313 | 6/2003 |
| WO | WO 03 050087 A2 | 6/2003 |
| WO | WO 2004/024702 A1 | 3/2004 |
| WO | WO 2004/039764 A1 | 5/2004 |
| WO | WO 2004/039780 | 5/2004 |
| WO | WO 2004/072018 | 8/2004 |

OTHER PUBLICATIONS

McGraw-Hill Dictionary of Chemical Terms(1990), pp. 282.*
Concise Encyclopedia Chemistry (1993), pp. 490.*

(Continued)

Primary Examiner—Janet L. Andres
Assistant Examiner—Raymond Covington
(74) Attorney, Agent, or Firm—Michael P. Morris; Mary-Ellen M. Devlin; Timothy X. Witkowski

(57) ABSTRACT

Alkyne compounds of formula I

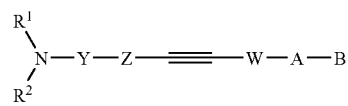

wherein A, B, W, X, Y, Z, $R^1$, and $R^2$ have the meanings given herein, which have MCH-receptor antagonistic activity and are useful for preparing pharmaceutical compositions for the treatment of metabolic disorders and/or eating disorders, particularly obesity and diabetes.

27 Claims, No Drawings

OTHER PUBLICATIONS

Hawley's Condensed Chemical Dictionary (1993), pp. 594.*

Yanyun Chen, et al. "Targeted Disruption of the Melanin-Concentrating Hormone Receptor-1 Results in Hyperphagia and Resistance to Diet-Induced Obesity", Endocrinology 143(7):2469-2477 2002.

Daqing Qu, et al. "A role for melanin-concentrating hormone in the central regulation of feeding behaviour" Nature vol. 380, pp. 243-247 1996.

Masako Shimada, et al. "Mice lacking melanin-concentrating hormone are hypophagic and lean" Nature vol. 396, pp. 670-674 1998.

Beth Borowsky, et al. "Antidepressant, anxiolytic and anorectic effects of a melanin-concentrating hormone-1 receptor antagonist" Nature Medicine vol. 8, No. 8, pp. 825-830, 2002.

Donald J. Marsh, et al. "Melanin-concentrating hormone 1 receptor-deficient mice are lean, hyperactive, and hyperphagic and have altered metabolism" PNAS, vol. 99, No. 5, pp. 3240-3245, 2002.

Shiro Takekawa, et al. "T-226296: a novel, orally active and selective melanin-concentrating hormone receptor antagonist" E. Journal of Pharm. vol. 438, pp. 129-135, 2002.

J. Krapcho, et al; "Immunosuppressive Activity of 2'-(3-Dimethylaminopropylthio)cinnamanilide (Cinanserin) and Relateld Compounds" J. Med. Chemistry. 1969, 12(1), 164-166.

Stenkamp, D. et al; U.S. Appl. No. 11/104,915—Alkyne Compounds with MCH Antagonistic Activity and Medicaments Comprising These Compounds filed Apr. 13, 2005.

Stenkamp, D. et al; U.S. Appl. No. 11/105,010—Alkyne Compounds with MCH Antagonistic Activity and Medicaments Comprising These Compounds filed Apr. 13, 2005.

Stenkamp, D. et al; U.S. Appl. No. 11/104,832—Alkyne Compounds with MCH Antagonistic Activity and Medicaments Comprising These Compounds filed Apr. 13, 2005.

Stenkamp, D. et al; U.S. Appl. No. 11/104,889—Alkyne Compounds with MCH Antagonistic Activity and Medicaments Comprising These Compounds filed Apr. 13, 2005.

* cited by examiner

ALKYNE COMPOUNDS WITH MCH ANTAGONISTIC ACTIVITY AND MEDICAMENTS COMPRISING THESE COMPOUNDS

RELATED APPLICATIONS

This application claims benefit of U.S. Ser. No. 60/563,388, filed Apr. 20, 2004, and claims priority to German Application No. 10 2004 017 932.8, filed Apr. 14, 2004, each of which is hereby incorporated by reference in its entirety.

FIELD OF THE INVENTION

The present invention relates to new alkyne compounds, the physiologically acceptable salts thereof as well as their use as MCH antagonists and their use in preparing a pharmaceutical preparation which is suitable for the prevention and/or treatment of symptoms and/or diseases caused by MCH or causally connected with MCH in some other way. The invention also relates to the use of a compound according to the invention for influencing eating behavior and for reducing body weight and/or for preventing any increase in body weight in a mammal. It further relates to compositions and medicaments containing a compound according to the invention and processes for preparing them.

BACKGROUND OF THE INVENTION

The intake of food and its conversion in the body is an essential part of life for all living creatures. Therefore, deviations in the intake and conversion of food generally lead to problems and also illness. The changes in the lifestyle and nutrition of humans, particularly in industrialized countries, have promoted morbid overweight (also known as corpulence or obesity) in recent decades. In affected people, obesity leads directly to restricted mobility and a reduction in the quality of life. There is the additional factor that obesity often leads to other diseases such as, for example, diabetes, dyslipidemia, high blood pressure, arteriosclerosis, and coronary heart disease. Moreover, high bodyweight alone puts an increased strain on the support and mobility apparatus, which can lead to chronic pain and diseases such as arthritis or osteoarthritis. Thus, obesity is a serious health problem for society.

The term obesity means an excess of adipose tissue in the body. In this connection, obesity is fundamentally to be seen as the increased level of fatness which leads to a health risk. There is no sharp distinction between normal individuals and those suffering from obesity, but the health risk accompanying obesity is presumed to rise continuously as the level of fatness increases. For simplicity's sake, in the present invention, individuals with a Body Mass Index (BMI), which is defined as the bodyweight measured in kilograms divided by the height (in meters) squared, above a value of 25 and more particularly above 30, are preferably regarded as suffering from obesity.

Apart from physical activity and a change in nutrition, there is currently no convincing treatment option for effectively reducing bodyweight. As obesity is a major risk factor in the development of serious and even life-threatening diseases, however, it is all the more important to have access to pharmaceutical active substances for the prevention and/or treatment of obesity. One approach which has been proposed very recently is the therapeutic use of MCH antagonists (cf. inter alia WO 01/21577 and WO 01/82925).

Melanin-concentrating hormone (MCH) is a cyclic neuropeptide consisting of 19 amino acids. It is synthesized predominantly in the hypothalamus in mammals and from there travels to other parts of the brain by the projections of hypothalamic neurons. Its biological activity is mediated in humans through two different glycoprotein-coupled receptors (GPCRs) from the family of rhodopsin-related GPCRs, namely the MCH receptors 1 and 2 (MCH-1R, MCH-2R).

Investigations into the function of MCH in animal models have provided good indications for a role of the peptide in regulating the energy balance, i.e., changing metabolic activity and food intake. D. Qu, et al., *A role for melanin-concentrating hormone in the central regulation of concentrating feeding behavior*, Nature, 1996, 380(6571): pp. 243-7; M. Shimada, et al., *Mice lacking melanin-concentrating hormone are hypophagic and lean*, Nature, 1998, 396(6712): pp. 670-4. For example, after intraventricular administration of MCH in rats, food intake was increased compared with control animals. Additionally, transgenic rats which produce more MCH than control animals, when given a high-fat diet, responded by gaining significantly more weight than animals without an experimentally altered MCH level. It was also found that there is a positive correlation between phases of increased desire for food and the quantity of MCH mRNA in the hypothalamus of rats. However, experiments with MCH knock-out mice are particularly important in showing the function of MCH. Loss of the neuropeptide results in lean animals with a reduced fat mass, which take in significantly less food than control animals.

The anorectic effects of MCH are presumably mediated in rodents through the G-Galpha i-coupled MCH-1R [B. Borowsky, et al., *Antidepressant, anxiolytic and anorectic effects of a melanin-concentrating hormone-1 receptor antagonist*, Nat Med, 2002, 8(8): pp. 825-30; Y. Chen, et al., *Targeted disruption of the melanin-concentrating hormone receptor-1 results in hyperphagia and resistance to diet-induced obesity*, Endocrinology, 2002, 143(7): pp. 2469-77; D. J. Marsh, et al., *Melanin-concentrating hormone 1 receptor-deficient mice are lean, hyperactive, and hyperphagic and have altered metabolism*. Proc Natl Acad Sci USA, 2002, 99(5): pp. 3240-5; S. Takekawa, et al., *T-226296: A novel, orally active and selective melanin-concentrating hormone receptor antagonist*. Eur J Pharmacol, 2002, 438(3): pp. 129-35.], as, unlike primates, ferrets, and dogs, no second MCH receptor subtype has hitherto been found in rodents. After losing the MCH-1R, knock-out mice have a lower fat mass, an increased energy conversion and, when fed on a high fat diet, do not put on weight, compared with control animals. Another indication of the importance of the MCH system in regulating the energy balance results from experiments with a receptor antagonist (SNAP-7941). B. Borowsky, et al., Nat Med, 2002, 8(8): pp. 825-30. In long term trials, the animals treated with the antagonist lose significant amounts of weight.

In addition to its anorectic effect, the MCH-1R antagonist SNAP-7941 also achieves additional anxiolytic and antidepressant effects in behavioral experiments on rats. B. Borowsky, et al., Nat Med, 2002, 8(8): pp. 825-30. Thus, there are clear indications that the MCH-MCH-1R system is involved not only in regulating the energy balance but also in affectivity.

In the patent literature certain amine compounds are proposed as MCH antagonists. Thus, WO 01/21577 (Takeda) describes compounds of formula

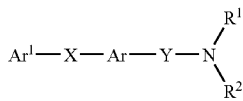

wherein $Ar^1$ denotes a cyclic group, X denotes a spacer, Y denotes a bond or a spacer, Ar denotes an aromatic ring which may be fused with a non-aromatic ring, $R^1$ and $R^2$ independently of one another denote H or a hydrocarbon group, while $R^1$ and $R^2$ together with the adjacent N atom may form an N-containing hetero ring and $R^2$ with Ar may also form a spirocyclic ring, and R together with the adjacent N atom and Y may form an N-containing hetero ring, as MCH antagonists for the treatment of obesity.

Moreover WO 01/82925 (Takeda) also describes compounds of formula

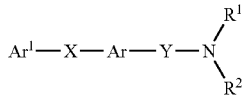

wherein $Ar^1$ denotes a cyclic group, X and Y represent spacer groups, Ar denotes an optionally substituted fused polycyclic aromatic ring, $R^1$ and $R^2$ independently of one another represent H or a hydrocarbon group, while $R^1$ and $R^2$ together with the adjacent N atom may form an N-containing heterocyclic ring and $R^2$ together with the adjacent N atom and Y may form an N-containing hetero ring, as MCH antagonists for the treatment of obesity, inter alia.

WO 2004/024702 proposes carboxylic acid amide compounds of formula I

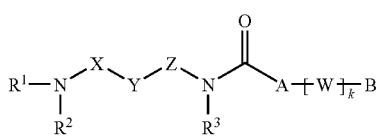

wherein Y, A and B may represent cyclic groups and X, Z, and W may denote bridges or bonds, as MCH-antagonists.

WO 04/039780 A1 describes alkyne compounds of formula I

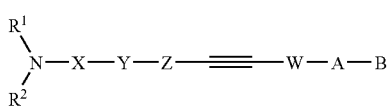

wherein Y, A, and B may denote cyclic groups and X, Z, and W may denote bridges or bonds, as MCH-antagonists.

WO 04/039764 A1 describes amide compounds of formula I

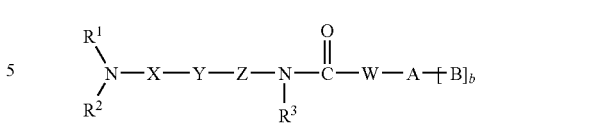

wherein Y, A and B may denote cyclic groups and X denotes an alkylene bridge, Z denotes a bridge or bond, and W is selected from the group comprising —$CR^{6a}R^{6b}$—O—, —$CR^{7a}$=$CR^{7c}$—, —$CR^{6a}R^{6b}$—$NR^8$—, —$CR^{7a}R^{7b}$—$CR^{7c}R^{7d}$—, and —$NR^8$—$CR^{6a}R^{6b}$—, as MCH-antagonists.

The aim of the present invention is to identify new alkyne compounds, particularly those which are especially effective as MCH antagonists. The invention also sets out to provide new alkyne compounds which can be used to influence the eating habits of mammals and achieve a reduction in body weight, particularly in mammals, and/or prevent an increase in body weight.

The present invention further sets out to provide new pharmaceutical compositions which are suitable for the prevention and/or treatment of symptoms and/or diseases caused by MCH or otherwise causally connected to MCH. In particular, the aim of this invention is to provide pharmaceutical compositions for the treatment of metabolic disorders such as obesity and/or diabetes as well as diseases and/or disorders which are associated with obesity and diabetes. Other objectives of the present invention are concerned with demonstrating advantageous uses of the compounds according to the invention. The invention also sets out to provide a process for preparing the amide compounds according to the invention. Other aims of the present invention will be immediately apparent to the skilled person from the foregoing remarks and those that follow.

SUMMARY OF THE INVENTION

In a first aspect the present invention relates to alkyne compounds of general formula I

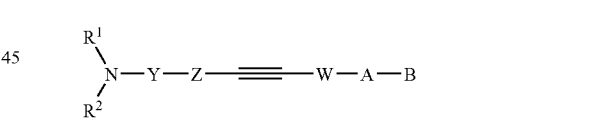

wherein:
$R^1$ and $R^2$ independently of one another denote H, $C_{1-8}$-alkyl, $C_{3-7}$-cycloalkyl, or a phenyl or pyridinyl group optionally mono- or polysubstituted by identical or different groups $R^{20}$ and/or monosubstituted by nitro, while the alkyl or cycloalkyl group may be mono- or polysubstituted by identical or different groups $R^{11}$, and a —$CH_2$— group in position 3 or 4 of a 5-, 6-, or 7-membered cycloalkyl group may be replaced by —O—, —S—, or —$NR^{13}$—, or
$R^1$ and $R^2$ form a $C_{3-8}$-alkylene bridge, wherein a —$CH_2$— group not adjacent to the N atom of the $R^1R^2N$ group may be replaced by —CH=N—, —CH=CH—, —O—, —S—, —SO—, —($SO_2$)—, —CO—, —C(=$CH_2$)—, or —$NR^{13}$—, while in the alkylene bridge defined hereinbefore one or more H atoms may be replaced by identical or different groups $R^{14}$, and the alkylene bridge defined hereinbefore may be substituted by one or two identical or different carbo- or heterocyclic groups Cy in such a way that the bond between the alkylene bridge and the group Cy is made via a single or double bond, via a common C atom forming a spirocyclic ring system, via two common adjacent C and/or N atoms forming a fused bicyclic ring system, or via three or more C and/or N atoms forming a bridged ring system;

W and Z independently of one another denote a single bond or a $C_{1-2}$-alkylene bridge, while two adjacent C atoms may be joined together with an additional $C_{1-4}$-alkylene bridge, and one or two C atoms independently of one another may be substituted by one or two identical or different $C_{1-3}$-alkyl groups, while two alkyl groups may be joined together to form a carbocyclic ring;

Y is selected from the definitions of the partial formulae Y1 to Y9

Y1
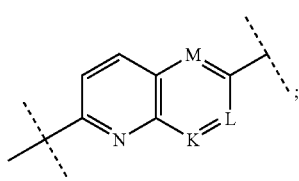

Y2
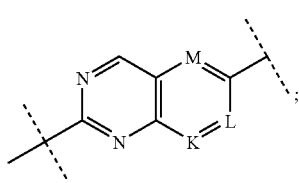

Y3
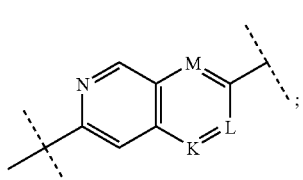

Y4
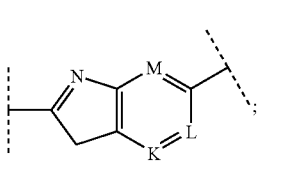

Y5
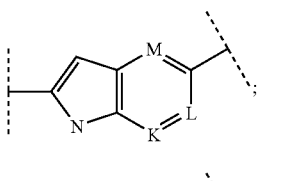

Y6
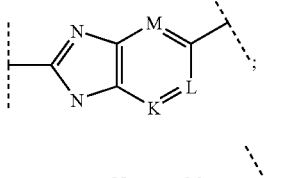

Y7
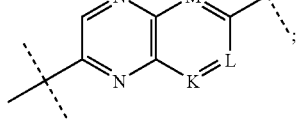

Y8
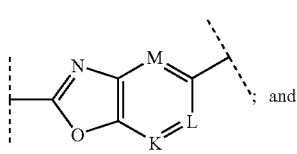
; and

Y9
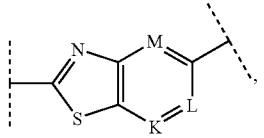

wherein the groups M, K, and L represent a CH group, while one of the groups M, K, and L may also represent an N atom, and in the partial formulae Y1 to Y9 one or more C atoms may be substituted independently of one another by $R^{20}$, and in the partial formulae Y5 and Y6 an NH group may be substituted by $C_{1-4}$-alkyl;

A is selected from among the bivalent cyclic groups phenyl, pyridinyl, pyrimidinyl, pyrazinyl, pyridazinyl, naphthyl, tetrahydronaphthyl, indolyl, dihydroindolyl, quinolinyl, dihydroquinolinyl, tetrahydroquinolinyl, isoquinolinyl, dihydroisoquinolinyl, tetrahydroisoquinolinyl, benzimidazolyl, benzoxazolyl, thienyl, furanyl, benzothienyl, or benzofuranyl, while the abovementioned cyclic groups may be mono- or polysubstituted at one or more C atoms by identical or different groups $R^{20}$, or in the case of a phenyl ring may also additionally be monosubstituted by nitro, and/or one or more NH groups may be substituted by $R^{21}$;

B has one of the meanings given for A or denotes $C_{1-6}$-alkyl, $C_{1-6}$-alkenyl, $C_{1-6}$-alkynyl, $C_{3-7}$-cycloalkyl, $C_{5-7}$-cycloalkenyl, $C_{3-7}$-cycloalkyl-$C_{1-3}$-alkyl, $C_{3-7}$-cycloalkenyl-$C_{1-3}$-alkyl, $C_{3-7}$-cycloalkyl-$C_{1-3}$-alkenyl, or $C_{3-7}$-cycloalkyl-$C_{1-3}$-alkynyl, wherein one or more C atoms independently of one another may be mono- or polysubstituted by halogen and/or monosubstituted by hydroxy or cyano and/or cyclic groups may be mono- or polysubstituted by identical or different groups $R^{20}$;

Cy denotes a carbo- or heterocyclic group selected from one of the following meanings a saturated 3- to 7-membered carbocyclic group, an unsaturated 4- to 7-membered carbocyclic group, a phenyl group, a saturated 4- to 7-membered or unsaturated 5- to 7-membered heterocyclic group with an N, O, or S atom as heteroatom, a saturated or unsaturated 5- to 7-membered heterocyclic group with two or more N atoms or with one or two N atoms and an O or S atom as heteroatoms, an aromatic heterocyclic 5- or 6-membered group with one or more identical or different heteroatoms selected from N, O, and/or S, while the abovementioned saturated 6- or 7-membered groups may also be present as bridged ring systems with an imino, ($C_{1-4}$-alkyl)-imino, methylene, ($C_{1-4}$-alkyl)-methylene or di-($C_{1-4}$-alkyl)-methylene bridge, and while the abovementioned cyclic groups may be mono- or polysubstituted at one or more C atoms by identical or different groups $R^{20}$, or in the case of a phenyl group may also additionally be monosubstituted by nitro, and/or one or more NH groups may be substituted by $R^{21}$;

$R^{11}$ denotes halogen, $C_{1-6}$-alkyl, $C_{2-6}$-alkenyl, $C_{2-6}$-alkynyl, $R^{15}$—O—, $R^{15}$—O—CO—, $R^{15}$—CO—O—, cyano, $R^{16}R^{17}N$, $R^{18}R^{19}N$—CO—, or Cy, while in the abovementioned groups one or more C atoms may be substituted independently of one another by substituents selected from halogen, OH, CN, CF$_3$, C$_{1-3}$-alkyl, or hydroxy-C$_{1-3}$-alkyl;

R$^{13}$ has one of the meanings given for R$^{17}$;

R$^{14}$ denotes halogen, cyano, C$_{1-6}$-alkyl, C$_{2-6}$-alkenyl, C$_{2-6}$-alkynyl, R$^{15}$—O—, R$^{15}$—O—CO—, R$^{15}$—CO—, R$^{15}$—CO—O—, R$^{16}$R$^{17}$N, R$^{18}$R$^{19}$N—CO—, R$^{15}$—O—C$_{1-3}$-alkyl, R$^{15}$—O—CO—C$_{1-3}$-alkyl, R$^{15}$—SO$_2$—NH, R$^{15}$—O—CO—NH—C$_{1-3}$-alkyl, R$^5$—SO$_2$—NH-C$_{1-3}$-alkyl, R$^{15}$—CO—C$_{1-3}$-alkyl, R$^{15}$—CO—O—C$_{1-3}$-alkyl, R$^{16}$R$^{17}$N—C$_{1-3}$-alkyl, R$^{18}$R$^{19}$N—CO—C$_{1-3}$-alkyl, or Cy-C$_{1-3}$-alkyl;

R$^{15}$ denotes H, C$_{1-4}$-alkyl, C$_{3-7}$-cycloalkyl, C$_{3-7}$-cycloalkyl-C$_{1-3}$-alkyl, phenyl, phenyl-C$_{1-3}$-alkyl, pyridinyl, or pyridinyl-C$_{1-3}$-alkyl;

R$^{16}$ denotes H, C$_{1-6}$-alkyl, C$_{3-7}$-cycloalkyl, C$_{3-7}$-cycloalkyl-C$_{1-3}$-alkyl, C$_{4-7}$-cycloalkenyl, C$_{4-7}$-cycloalkenyl-C$_{1-3}$-alkyl, ω-hydroxy-C$_{2-3}$-alkyl, ω-(C$_{1-4}$-alkoxy)-C$_{2-3}$-alkyl, amino-C$_{2-6}$-alkyl, C$_{1-4}$-alkyl-amino-C$_{2-6}$-alkyl, di-(C$_{1-4}$-alkyl)-amino-C$_{2-6}$-alkyl, or cyclo-C$_{3-6}$-alkyleneimino-C$_{2-6}$-alkyl;

R$^{17}$ has one of the meanings given for R$^{16}$ or denotes phenyl, phenyl-C$_{1-3}$-alkyl, pyridinyl, C$_{1-4}$-alkylcarbonyl, hydroxycarbonyl-C$_{1-3}$-alkyl, C$_{1-4}$-alkoxycarbonyl, C$_{1-4}$-alkoxycarbonyl-C$_{1-3}$-alkyl, C$_{1-4}$-alkylcarbonylamino-C$_{2-3}$-alkyl, N—(C$_{1-4}$-alkylcarbonyl)-N—(C$_{1-4}$-alkyl)-amino-C$_{2-3}$-alkyl, C$_{1-4}$-alkylsulfonyl, C$_{1-4}$-alkylsulfonylamino-C$_{2-3}$-alkyl, or N—(C$_4$-alkylsulfonyl)-N(—C$_{1-4}$-alkyl)-amino-C$_{2-3}$-alkyl;

R$^{18}$ and R$^{19}$ independently of one another denote H or C$_{1-6}$-alkyl;

R$^{20}$ denotes halogen, hydroxy, cyano, C$_{1-6}$-alkyl, C$_{2-6}$-alkenyl, C$_{2-6}$-alkynyl, C$_{3-7}$-cycloalkyl, C$_{3-7}$-cycloalkyl-C$_{1-3}$-alkyl, hydroxy-C$_{1-3}$-alkyl, R$^{22}$—C$_{1-3}$-alkyl, or has one of the meanings given for R$^{22}$;

R$^{21}$ denotes C$_{1-4}$-alkyl, ω-hydroxy-C$_{2-6}$-alkyl, ω-C$_{1-4}$-alkoxy-C$_{2-6}$-alkyl, ω-C$_{1-4}$-alkyl-amino-C$_{2-6}$-alkyl, ω-di-(C$_{1-4}$-alkyl)-amino-C$_{2-6}$-alkyl, ω-Cyclo-C$_{3-6}$-alkylene-imino-C$_{2-6}$-alkyl, phenyl, phenyl-C$_{1-3}$-alkyl, C$_{1-4}$-alkylcarbonyl, C$_{1-4}$-alkoxy-carbonyl, C$_{1-4}$-alkylsulfonyl, aminosulfonyl, C$_{1-4}$-alkylaminosulfonyl, di-C$_{1-4}$-alkylaminosulfonyl, or cyclo-C$_{3-6}$-alkylene-iminosulfonyl; and R$^{22}$ denotes pyridinyl, phenyl, phenyl-C$_{1-3}$-alkoxy, cyclo-C$_{3-6}$-alkyleneimino-C$_{2-4}$-alkoxy, OHC—, HO—N═HC—, C$_{1-4}$-alkoxy-N═HC—, C$_{1-4}$-alkoxy, C$_{1-4}$-alkylthio, carboxy, C$_{1-4}$-alkylcarbonyl, C$_{1-4}$-alkoxycarbonyl, aminocarbonyl, C$_{1-4}$-alkylaminocarbonyl, di-(C$_{1-4}$-alkyl)-aminocarbonyl, cyclo-C$_{3-6}$-alkyl-aminocarbonyl, cyclo-C$_{3-6}$-alkyleneimino-carbonyl, phenylaminocarbonyl, cyclo-C$_{3-6}$-alkyleneimino-C$_{2-4}$-alkyl-aminocarbonyl, C$_{1-4}$-alkyl-sulfonyl, C$_{1-4}$-alkyl-sulfinyl, C$_{1-4}$-alkyl-sulfonylamino, amino, C$_{1-4}$-alkylamino, di-(C$_{1-4}$-alkyl)-amino, C$_{1-4}$-alkyl-carbonylamino, Cyclo-C$_{3-6}$-alkyleneimino, phenyl-C$_{1-3}$-alkylamino, N—(C$_{1-4}$-alkyl)-phenyl-C$_{1-3}$-alkylamino, acetylamino, propionylamino, phenylcarbonyl, phenylcarbonylamino, phenylcarbonylmethylamino, hydroxy-C$_{2-3}$-alkylaminocarbonyl, (4-morpholinyl)carbonyl, (1-pyrrolidinyl)carbonyl, (1-piperidinyl)carbonyl, (hexahydro-1-azepinyl)carbonyl, (4-methyl-1-piperazinyl)carbonyl, methylenedioxy, aminocarbonylamino, or C$_{1-4}$-alkylaminocarbonylamino;

while in the abovementioned groups and radicals, particularly in W, Z, R$^{13}$ to R$^{22}$, in each case one or more C atoms may additionally be mono- or polysubstituted by F and/or in each case one or two C atoms independently of one another may additionally be monosubstituted by Cl or Br and/or in each case one or more phenyl rings may additionally comprise independently of one another one, two or three substituents selected from the group F, Cl, Br, I, cyano, C$_{1-4}$-alkyl, C$_{1-4}$-alkoxy, difluoromethyl, trifluoromethyl, hydroxy, amino, C$_{1-3}$-alkylamino, di-(C$_{1-3}$-alkyl)-amino, acetylamino, aminocarbonyl, difluoromethoxy, trifluoromethoxy, amino-C$_{1-3}$-alkyl, C$_{1-3}$-alkylamino-C$_{1-3}$-alkyl-, and di-(C$_{1-3}$-alkyl)-amino-C$_{1-3}$-alkyl, and/or may be monosubstituted by nitro, and the H atom of any carboxy group present or an H atom bound to an N atom may in each case be replaced by a group which can be cleaved in vivo, the tautomers, the diastereomers, the enantiomers, the mixtures thereof, and the salts thereof.

The invention also relates to the compounds in the form of the individual optical isomers, mixtures of the individual enantiomers or racemates, in the form of the tautomers and in the form of the free bases or corresponding acid addition salts with pharmacologically acceptable acids. The subject of the invention also includes the compounds according to the invention, including their salts, wherein one or more hydrogen atoms are replaced by deuterium.

This invention also includes the physiologically acceptable salts of the alkyne compounds according to the invention as described above and hereinafter.

Also covered by this invention are compositions containing at least one alkyne compound according to the invention and/or a salt according to the invention optionally together with one or more physiologically acceptable excipients.

Also covered by this invention are pharmaceutical compositions containing at least one alkyne compound according to the invention and/or a salt according to the invention optionally together with one or more inert carriers and/or diluents.

This invention also relates to the use of at least one alkyne compound according to the invention and/or a salt according to the invention for influencing the eating behavior of a mammal.

The invention further relates to the use of at least one alkyne compound according to the invention and/or a salt according to the invention for reducing the body weight and/or for preventing an increase in the body weight of a mammal.

The invention also relates to the use of at least one alkyne compound according to the invention and/or a salt according to the invention for preparing a pharmaceutical composition with an MCH receptor-antagonistic activity, particularly with an MCH-1 receptor-antagonistic activity.

This invention also relates to the use of at least one alkyne compound according to the invention and/or a salt according to the invention for preparing a pharmaceutical composition which is suitable for the prevention and/or treatment of symptoms and/or diseases which are caused by MCH or are otherwise causally connected with MCH.

A further object of this invention is the use of at least one alkyne compound according to the invention and/or a salt according to the invention for preparing a pharmaceutical composition which is suitable for the prevention and/or treatment of metabolic disorders and/or eating disorders, particularly obesity, bulimia, bulimia nervosa, cachexia, anorexia, anorexia nervosa and hyperphagia.

The invention also relates to the use of at least one alkyne compound according to the invention and/or a salt according to the invention for preparing a pharmaceutical composition which is suitable for the prevention and/or treatment of diseases and/or disorders associated with obesity, particularly diabetes, especially type II diabetes, complications of diabetes including diabetic retinopathy, diabetic neuropathy, diabetic nephropathy, insulin resistance, pathological glucose tolerance, encephalorrhagia, cardiac insufficiency, cardiovascular diseases, particularly arteriosclerosis and high blood pressure, arthritis and gonitis.

In addition the present invention relates to the use of at least one alkyne compound according to the invention and/or a salt according to the invention for preparing a pharmaceutical composition which is suitable for the prevention and/or treatment of hyperlipidemia, cellulitis, fat accumulation, malignant mastocytosis, systemic mastocytosis, emotional disorders, affective disorders, depression, anxiety, sleep disorders, reproductive disorders, sexual disorders, memory disorders, epilepsy, forms of dementia and hormonal disorders.

The invention also relates to the use of at least one alkyne compound according to the invention and/or a salt according to the invention for preparing a pharmaceutical composition which is suitable for the prevention and/or treatment of urinary problems, such as, for example, urinary incontinence, overactive bladder, urgency, nycturia, and enuresis.

The invention further relates to the use of at least one alkyne compound according to the invention and/or a salt according to the invention for preparing a pharmaceutical composition which is suitable for the prevention and/or treatment of dependencies and/or withdrawal symptoms.

The invention further relates to processes for preparing for preparing a pharmaceutical composition according to the invention, characterized in that at least one alkyne compound according to the invention and/or a salt according to the invention is incorporated in one or more inert carriers and/or diluents by a non-chemical method.

The invention also relates to a pharmaceutical composition containing a first active substance which is selected from the alkyne compounds according to the invention and/or the corresponding salts as well as a second active substance which is selected from the group consisting of active substances for the treatment of diabetes, active substances for the treatment of diabetic complications, active substances for the treatment of obesity, preferably other than MCH antagonists, active substances for the treatment of high blood pressure, active substances for the treatment of dyslipidemia or hyperlipidemia, including arteriosclerosis, active substances for the treatment of arthritis, active substances for the treatment of anxiety states and active substances for the treatment of depression, optionally together with one or more inert carriers and/or diluents.

Moreover, in one aspect, the invention relates to a process for preparing alkyne compounds of formula A.5

$$R^1R^2N\text{—}Y\text{—}C\equiv C\text{—}W\text{-}A\text{-}B \quad (A.5)$$

while in formulae A.1, A.2, A.3, A.4, and A.5, $R^1$, $R^2$, Y, W, A, and B have one of the meanings given hereinbefore and hereinafter, wherein a halogen compound of formula A.1

$$HO\text{—}Y\text{-}Hal \quad (A.1)$$

wherein Hal denotes chlorine, bromine, or iodine, preferably bromine or iodine is reacted with an alkyne compound of formula A.2

$$H\text{—}C\equiv C\text{—}W\text{-}A\text{-}B \quad (A.2)$$

in the presence of a suitable palladium catalyst, a suitable base, and copper (I) iodide in a suitable solvent, and the compound of formula A.3 obtained $$HO\text{—}Y\text{—}C\equiv C\text{—}W\text{-}A\text{-}B \quad (A.3)$$

is reacted with a suitable halogenating agent to form the halide derivative A.4 in which Hal' denotes Cl, Br, or I, $$Hal'\text{-}Y\text{—}C\equiv C\text{—}W\text{-}A\text{-}B \quad (A.4)$$

which is further reacted with an amine of formula $H\text{—}NR^1R^2$ to form the end product A.5.

This invention further relates to a process for preparing alkyne compounds of formula B.5

$$R^1R^2N\text{—}Y\text{-}Z\text{-}C\equiv C\text{-}A\text{-}B \quad (B.5)$$

while in formulae B.1, B.2, B.3, B.4, and B.5, $R^1$, $R^2$, Y, Z, A, and B have one of the meanings given hereinbefore and hereinafter, wherein a halogen compound of formula B.1

$$Hal\text{-}A\text{-}B \quad (B.1)$$

wherein Hal denotes chlorine, bromine, or iodine, preferably bromine or iodine, is reacted with an alkyne compound of formula B.2

$$HO\text{—}Y\text{-}Z\text{-}C\equiv C\text{—}H \quad (B.2)$$

in the presence of a suitable palladium catalyst, a suitable base, and copper (I) iodide in a suitable solvent, and the resulting compound of formula B.3

$$HO\text{—}Y\text{-}Z\text{-}C\equiv C\text{-}A\text{-}B \quad (B.3)$$

is reacted with a suitable halogenating agent to form the halide derivative B.4 in which Hal' denotes Cl, Br, or I, $$Hal'\text{-}Y\text{-}Z\text{-}C\equiv C\text{-}A\text{-}B \quad (B.4)$$

which is reacted further with an amine of formula $H\text{—}NR^1R^2$ to form the end product B.5.

In addition, the invention relates to a process for preparing alkyne compounds of formula C.3

$$R^1R^2N\text{—}Y\text{—}C\equiv C\text{—}W\text{-}A\text{-}B \quad (C.3)$$

while in formulae C.1, C.2, and C.3, $R^1$, $R^2$, Y, W, A, and B have one of the meanings given hereinbefore and hereinafter, wherein a halogen compound of formula C.1

$$R^1R^2N\text{—}Y\text{-}Hal \quad (C.1)$$

wherein Hal denotes chlorine, bromine, or iodine, preferably bromine or iodine, is further reacted with an alkyne compound of formula C.2

$$H\text{—}C\equiv C\text{—}W\text{-}A\text{-}B \quad (C.2)$$

in the presence of a suitable palladium catalyst, a suitable base, and copper (I) iodide in a suitable solvent to yield the end product C.3.

In another aspect the invention relates to a process for preparing alkyne compounds of formula D.3

$$R^1R^2N\text{—}Y\text{-}Z\text{-}C\equiv C\text{-}A\text{-}B \quad (D.3)$$

while in formulae D.1, D.2, and D.3, $R^1$, $R^2$, Y, Z, A, and B have one of the meanings given hereinbefore and hereinafter, wherein a halogen compound of formula D.2

$$Hal\text{-}A\text{-}B \quad (D.2)$$

wherein Hal denotes chlorine, bromine, or iodine, preferably bromine or iodine, is reacted with an alkyne compound of formula D.1

$$R^1R^2N\text{—}Y\text{-}Z\text{-}C\equiv C\text{—}H \quad (D.1)$$

in the presence of a suitable palladium catalyst, a suitable base, and copper (I) iodide in a suitable solvent to form the end product D.3.

The starting materials and intermediate products used in the synthesis according to the invention are also a subject of this invention.

DETAILED DESCRIPTION OF THE INVENTION

Unless otherwise specified, the groups, residues and substituents, particularly A, B, W, Y, Z, Cy, $R^1$, $R^2$, $R^{11}$, $R^{13}$ to $R^{22}$, M, K, and L, have the meanings given hereinbefore.

If groups, residues and/or substituents occur more than once in a compound, they may have the same or different meanings in each case.

If $R^1$ and $R^2$ are not joined together via an alkylene bridge, $R^1$ and $R^2$ independently of one another preferably denote a $C_{1-8}$-alkyl or $C_{3-7}$-cycloalkyl group mono- or polysubstituted by identical or different groups $R^{11}$, while a —$CH_2$— group in position 3 or 4 of a 5-, 6-, or 7-membered cycloalkyl group may be replaced by —O—, —S— or —$NR^{13}$—, or a phenyl or pyridinyl group optionally mono- or polysubstituted by identical or different groups $R^{20}$ and/or monosubstituted by nitro, while one or both of the groups $R^1$ and $R^2$ may also represent H.

Preferred meanings of the group $R^{11}$ are F, Cl, Br, $C_{1-6}$-alkyl, $C_{2-6}$-alkenyl, $C_{2-6}$-alkynyl, $R^{15}$—O—, cyano, $R^{16}R^{17}N$, $C_{3-7}$-cycloalkyl, cyclo-$C_{3-6}$-alkyleneimino, pyrrolidinyl, N—($C_{1-4}$-alkyl)-pyrrolidinyl, piperidinyl, N—($C_{1-4}$-alkyl)-piperidinyl, phenyl, and pyridyl, while in the above-mentioned groups and radicals one or more C atoms may be mono- or polysubstituted independently of one another by F, $C_{1-3}$-alkyl or hydroxy-$C_{1-3}$-alkyl, and/or one or two C atoms may be monosubstituted independently of one another by Cl, Br, OH, $CF_3$, or CN, and the abovementioned cyclic groups may be mono- or polysubstituted at one or more C atoms by identical or different radicals $R^{20}$, or in the case of a phenyl group may also additionally be monosubstituted by nitro, and/or one or more NH groups may be substituted by $R^2$. If $R^{11}$ has one of the meanings $R^{15}$—O—, cyano, $R^{16}R^{17}N$, or cyclo-$C_{3-6}$-alkyleneimino, the C atom of the alkyl or cycloalkyl group substituted by $R^{11}$ is preferably not directly connected to a heteroatom, such as, for example, the group —N—X—.

Preferably the groups $R^1$, $R^2$ independently of one another represent H, $C_{1-6}$-alkyl, $C_{3-5}$-alkenyl, $C_{3-5}$-alkynyl, $C_{3-7}$-cycloalkyl, hydroxy-$C_{3-7}$-cycloalkyl, $C_{3-7}$-cycloalkyl-$C_{1-3}$-alkyl, (hydroxy-$C_{3-7}$-cycloalkyl)-$C_{1-3}$-alkyl, hydroxy-$C_{2-4}$-alkyl, ω-NC—$C_{2-3}$-alkyl, $C_{1-4}$-alkoxy-$C_{2-4}$-alkyl, hydroxy-$C_4$-alkoxy-$C_{2-4}$-alkyl, $C_{1-4}$-alkoxy-carbonyl-$C_{1-4}$-alkyl, carboxyl-$C_{1-4}$-alkyl, amino-$C_{2-4}$-alkyl, $C_{1-4}$-alkyl-amino-$C_{2-4}$-alkyl, di-($C_{1-4}$-alkyl)-amino-$C_{2-4}$-alkyl, cyclo-$C_{3-6}$-alkyleneimino-$C_{2-4}$-alkyl, pyrrolidin-3-yl, N—($C_{1-4}$-alkyl)-pyrrolidin-3-yl, pyrrolidinyl-$C_{1-3}$-alkyl, N—($C_{1-4}$-alkyl)-pyrrolidinyl-$C_{1-3}$-alkyl, piperidin-3-yl, piperidin-4-yl, N—($C_{1-4}$-alkyl)-piperidin-3-yl, N—($C_{1-4}$-alkyl)-piperidin-4-yl, piperidinyl-$C_{1-3}$-alkyl, N—($C_{1-4}$-alkyl)-piperidinyl-$C_{1-3}$-alkyl, tetrahydropyran-3-yl, tetrahydropyran-4-yl, tetrahydrofuran-2-ylmethyl, tetrahydrofuran-3-ylmethyl, phenyl, phenyl-$C_{1-3}$-alkyl, pyridyl, or pyridyl-$C_{1-3}$-alkyl, while in the above-mentioned groups and radicals one or more C atoms independently of one another may be mono- or polysubstituted by F, $C_{1-3}$-alkyl, or hydroxy-$C_{1-3}$-alkyl, and/or one or two C atoms independently of one another may be monosubstituted by Cl, Br, OH, $CF_3$, or CN, and the abovementioned cyclic groups may be mono- or polysubstituted at one or more C atoms by identical or different radicals $R^{20}$, in the case of a phenyl group may also additionally be monosubstituted by nitro, and/or one or more NH groups may be substituted by $R^{21}$. Preferred substituents of the abovementioned phenyl or pyridyl groups are selected from the group F, Cl, Br, I, cyano, $C_{1-4}$-alkyl, $C_{1-4}$-alkoxy, difluoromethyl, trifluoromethyl, hydroxy, amino, $C_{1-3}$-alkylamino, di-($C_{1-3}$-alkyl)-amino, acetylamino, aminocarbonyl, difluoromethoxy, trifluoromethoxy, amino-$C_{1-3}$-alkyl, $C_{1-3}$-alkylamino-$C_{1-3}$-alkyl, and di-($C_{1-3}$-alkyl)-amino-$C_{1-3}$-alkyl, while a phenyl group may also be monosubstituted by nitro.

Particularly preferred definitions of the groups $R^1$ and/or $R^2$ are selected from the group consisting of H, $C_{1-4}$-alkyl, hydroxy-$C_{1-4}$-alkyl, $C_{3-5}$-alkenyl, $C_{3-5}$-alkynyl, $C_{3-7}$-cycloalkyl, hydroxy-$C_{3-7}$-cycloalkyl, dihydroxy-$C_{3-6}$-alkyl, $C_{3-7}$-cycloalkyl-$C_{1-3}$-alkyl, tetrahydropyran-3-yl, tetrahydropyran-4-yl, tetrahydrofuran-2-ylmethyl, tetrahydrofuran-3-ylmethyl, (hydroxy-$C_{3-7}$-cycloalkyl)-$C_{1-3}$-alkyl, ω-($C_{1-4}$-alkoxy)-$C_{2-3}$-alkyl, di-($C_{1-3}$-alkyl)amino-$C_{2-3}$-alkyl, pyrrolidin-N-yl-$C_{2-3}$-alkyl, piperidin-N-yl-$C_{2-3}$-alkyl, pyridyl, and benzyl, while an alkyl, cycloalkyl or cycloalkyl-alkyl group may additionally be mono- or disubstituted by hydroxy and/or hydroxy-$C_{1-3}$-alkyl, and/or mono- or polysubstituted by F or $C_{1-3}$-alkyl and/or monosubstituted by $CF_3$, Br, Cl, or CN.

Most particularly preferred groups $R^1$ and/or $R^2$ are selected from the group consisting of H, methyl, ethyl, n-propyl, isopropyl, prop-2-enyl, but-2-enyl, prop-2-ynyl, but-2-ynyl, 2-methoxyethyl, cyclopropyl, cyclopentyl, cyclohexyl, cyclopropylmethyl, cyclopentylmethyl, hydroxy-$C_{3-7}$-cycloalkyl, (hydroxy-$C_{1-3}$-alkyl)-hydroxy-$C_{3-7}$-cycloalkyl, dihydroxy-$C_{3-5}$-alkyl, 2-hydroxy-1-(hydroxymethyl)ethyl, 1,1-di(hydroxymethyl)ethyl, (1-hydroxy-$C_{3-6}$-cycloalkyl)-methyl, tetrahydropyran-3-yl, tetrahydropyran-4-yl, tetrahydrofuran-2-ylmethyl, tetrahydrofuran-3-ylmethyl, 2-hydroxyethyl, 3-hydroxypropyl, di-($C_{1-3}$-alkyl)aminoethyl, pyrrolidin-N-ylethyl, piperidin-N-ylethyl, benzyl, and pyridyl, while the abovementioned groups may be mono- or polysubstituted by F and/or $C_{1-3}$-alkyl, and the phenyl and pyridyl rings may be substituted as specified.

Examples of most particularly preferred groups $R^1$ and/or $R^2$ are therefore H, methyl, ethyl, n-propyl, isopropyl, prop-2-enyl, prop-2-ynyl, 2-methoxyethyl, cyclopropyl, cyclopentyl, cyclohexyl, cyclopropylmethyl, cyclopentylmethyl, hydroxycyclopentyl, hydroxycyclohexyl, (hydroxymethyl)hydroxycyclopentyl, (hydroxymethyl)hydroxycyclohexyl, 2,3-dihydroxypropyl, (1-hydroxycyclopropyl)methyl, tetrahydropyran-3-yl, tetrahydropyran-4-yl, tetrahydrofuran-2-ylmethyl, tetrahydrofuran-3-ylmethyl, 2-hydroxyethyl, 3-hydroxypropyl, dimethylaminoethyl, benzyl, and pyridyl.

Particularly preferably, at least one of the groups $R^1$, $R^2$ has a meaning other than H.

If $R^1$ and $R^2$ form an alkylene bridge, this is preferably a $C_{3-7}$-alkylene bridge or a $C_{3-7}$-alkylene bridge, wherein a —$CH_2$— group not adjacent to the N atom of the $R^1R^2N$ group is replaced by —CH=N—, —CH=CH—, —O—, —S—, —CO—, or —$NR^{13}$—, while in the alkylene bridge defined hereinbefore one or more H atoms may be replaced by identical or different groups $R^{14}$, and the alkylene bridge defined hereinbefore may be substituted with a carbo- or heterocyclic group Cy in such a way that the bond between the alkylene bridge and the group Cy is made via a single or double bond, via a common C atom forming a spirocyclic ring system, via two common adjacent C— and/or N atoms forming a fused bicyclic ring system or via three or more C— and/or N atoms forming a bridged ring system.

Preferably also, $R^1$ and $R^2$ form an alkylene bridge such that $R^1R^2N$— denotes a group which is selected from azetidine, pyrrolidine, piperidine, azepan, 2,5-dihydro-1H-pyrrole, 1,2,3,6-tetrahydropyridine, 2,3,4,7-tetrahydro-1H-azepine, 2,3,6,7-tetrahydro-1H-azepine, piperazine in which the free imine function is substituted by $R^{13}$, piperidin-4-one, morpholine, and thiomorpholine, is particularly preferably selected from pyrrolidine, piperidine, piperazine in which the free imine function is substituted by $R^{13}$, and morpholine, while according to the general definition of $R^1$ and $R^2$ one or more H atoms may be replaced by identical or different groups $R^{14}$, and/or the abovementioned groups may be substituted by one or two identical or different carbo- or heterocyclic groups Cy in a manner specified according to the general definition of $R^1$ and $R^2$, while the group Cy may be mono- or polysubstituted by $R^{20}$.

Particularly preferred groups Cy are $C_{3-7}$-cycloalkyl and aza-$C_{4-7}$-cycloalkyl, particularly cyclo-$C_{3-6}$-alkyleneimino, as well as 1-$C_{1-4}$-alkyl-aza-$C_{4-7}$-cycloalkyl, while the group Cy may be mono- or polysubstituted by $R^{20}$.

The $C_{3-8}$-alkylene bridge formed by $R^1$ and $R^2$, wherein —$CH_2$— groups may be replaced as specified, may be substituted, as described, by one or two identical or different carbo- or heterocyclic groups Cy, which may be substituted as specified hereinbefore.

In the event that the alkylene bridge is linked to a group Cy through a single bond, Cy is preferably selected from the group consisting of $C_{3-7}$-cycloalkyl, cyclo-$C_{3-6}$-alkyleneimino, 1H-imidazole, thienyl, and phenyl.

In the event that the alkylene bridge is linked to a group Cy via a common C atom forming a spirocyclic ring system, Cy is preferably selected from the group consisting of $C_{3-7}$-cycloalkyl, aza-$C_{4-8}$-cycloalkyl, oxa-$C_{4-8}$-cycloalkyl, and 2,3-dihydro-1H-quinazolin-4-one.

In the event that the alkylene bridge is linked to a group Cy via two common adjacent C and/or N atoms forming a fused bicyclic ring system, Cy is preferably selected from the group consisting of $C_{4-7}$-cycloalkyl, phenyl, and thienyl.

In the event that the alkylene bridge is linked to a group Cy via three or more C and/or N atoms forming a bridged ring system, Cy preferably denotes $C_{4-8}$-cycloalkyl or aza-$C_{4-8}$-cycloalkyl.

In the event that the heterocyclic group $R^1R^2N$— is substituted by a group Cy, the group Cy is preferably linked to the group $R^1R^2N$— through a single bond, while Cy is preferably selected from the group consisting of $C_{3-7}$-cycloalkyl and cyclo-$C_{3-6}$-alkyleneimino, while these groups may be substituted as specified, preferably by fluorine, $C_{1-3}$-alkyl, hydroxy-$C_{1-3}$-alkyl, and hydroxy.

Particularly preferably the group

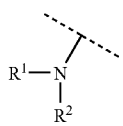

is defined according to one of the following partial formulae:

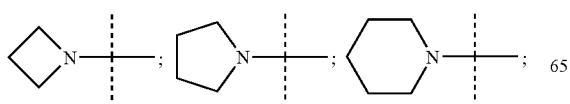

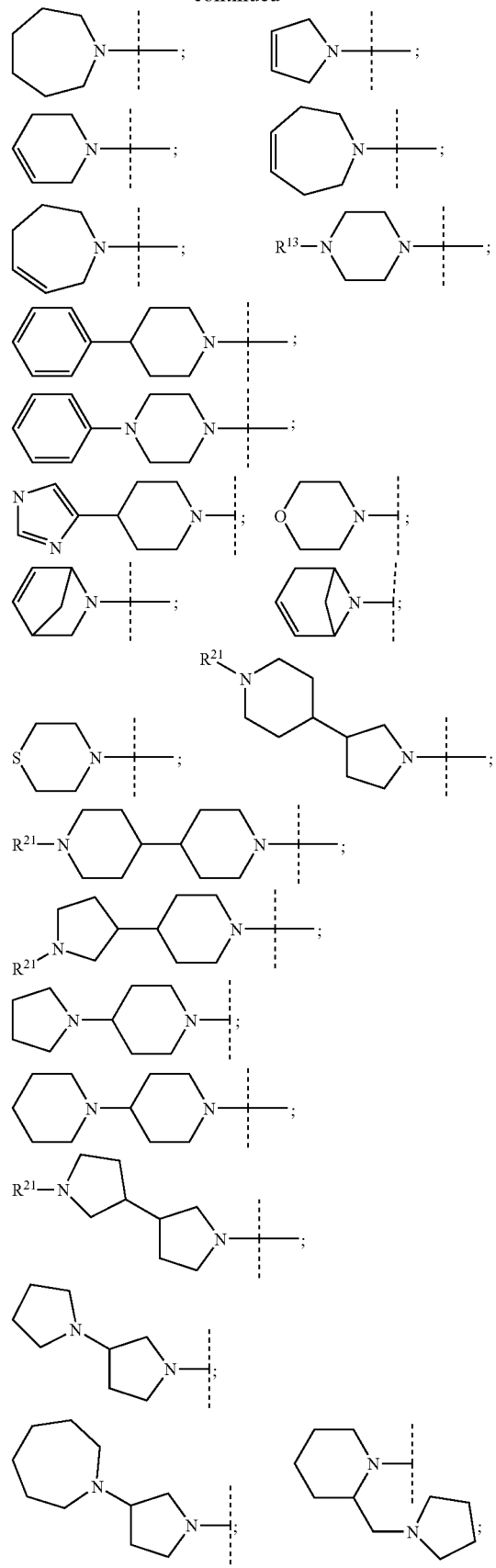

-continued

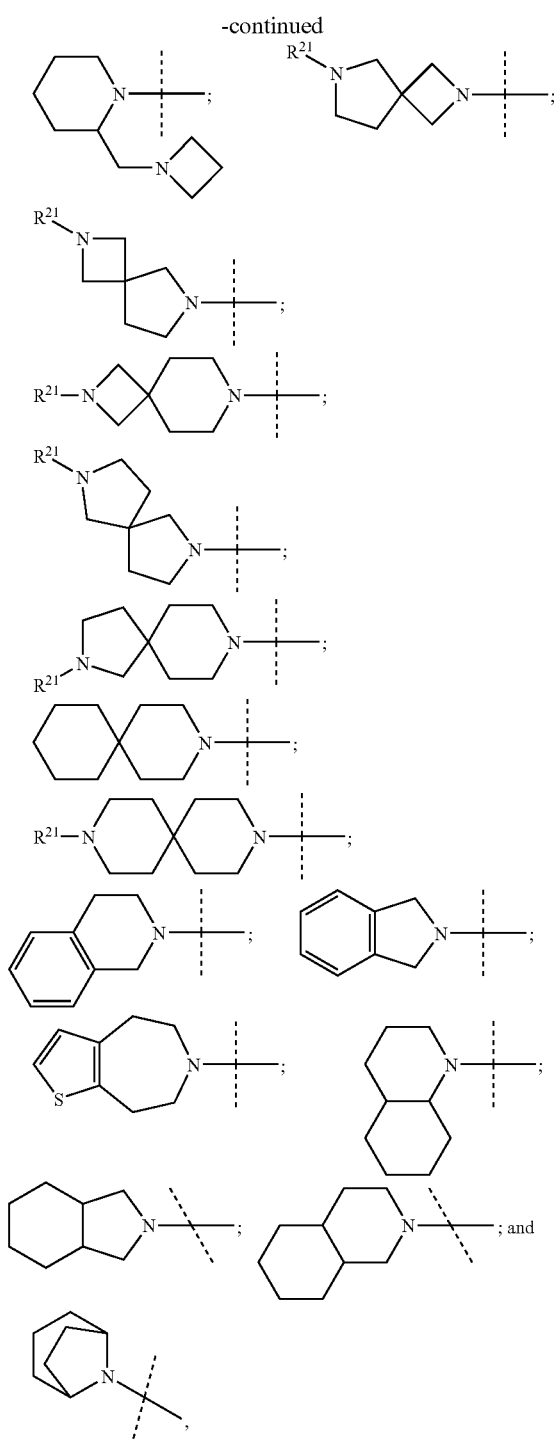

wherein one or more H atoms of the heterocycle formed by the group $R^1R^2N$— may be replaced by identical or different groups $R^{14}$, and the heterocycle formed by the group $R^1R^2N$— may be substituted by one or two, preferably one $C_{3-7}$-cycloalkyl group, while the cycloalkyl group may be mono- or polysubstituted by $R^{20}$, and the ring attached to the heterocycle formed by the group $R^1R^2N$— may be mono- or polysubstituted at one or more C atoms by $R^{20}$, or in the case of a phenyl ring may also additionally be monosubstituted by nitro and wherein $R^{13}$, $R^{14}$, $R^{20}$, and $R^{21}$ have the meanings given hereinbefore and hereinafter.

If the heterocycle formed by the group $R^1R^2N$— is substituted as specified by one or two cycloalkyl groups mono- or polysubstituted by $R^{20}$, the substituents $R^{20}$ independently of one another preferably denote $C_{1-4}$-alkyl, $C_{1-4}$-alkoxy-$C_{1-3}$-alkyl, hydroxy-$C_{1-3}$-alkyl, hydroxy, fluorine, chlorine, bromine, or $CF_3$, particularly hydroxy.

Most particularly preferably the group

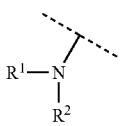

is defined according to one of the following partial formulae:

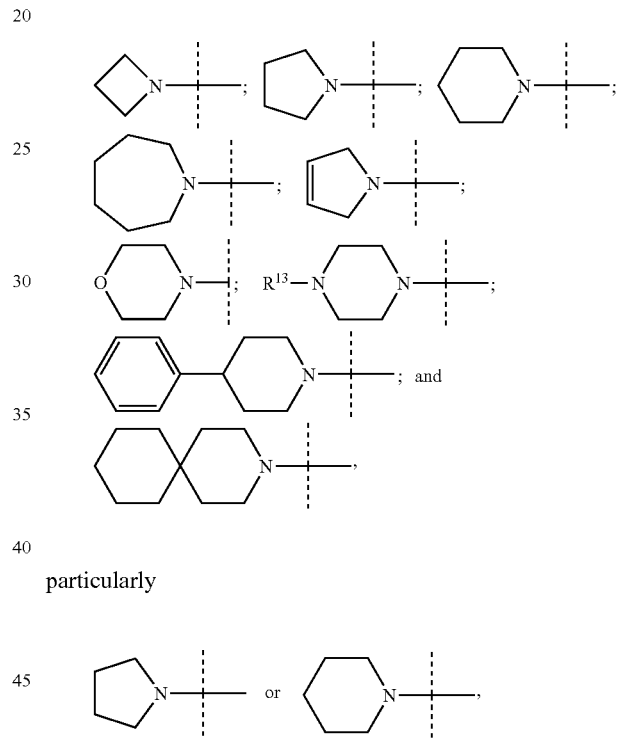

particularly

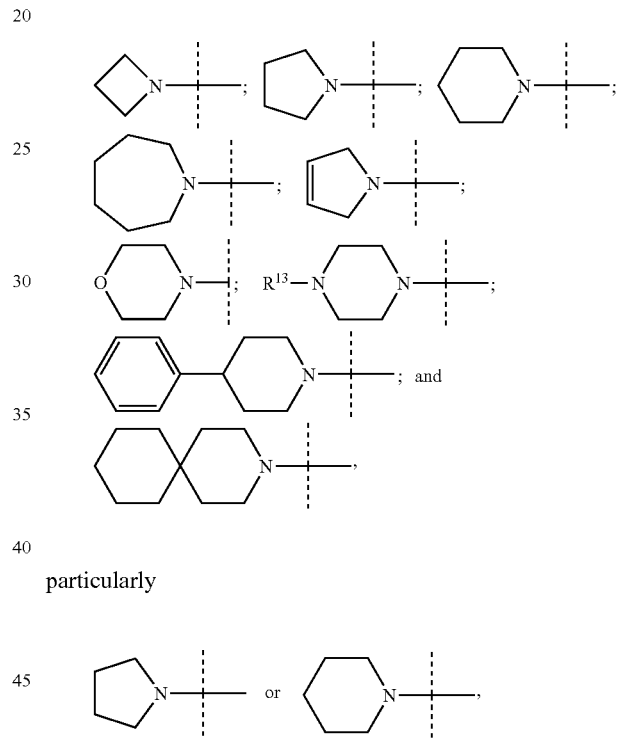

where $R^{13}$ has the meanings given above and hereinafter, and the heterocycle formed by the group $R^1R^2N$— may be substituted by $C_{3-6}$-cycloalkyl, hydroxy-$C_{3-6}$-cycloalkyl, or (hydroxy-$C_{3-6}$-cycloalkyl)-$C_{1-3}$-alkyl, and the heterocycle formed by the group $R^1R^2N$— may be mono-, di-, or trisubstituted by identical or different groups $R^{14}$. The substituents $R^{14}$ preferably denote independently of one another F, Cl, Br, OH, $C_{1-4}$-alkyl, $C_{1-4}$-alkoxy, $C_{1-4}$-alkoxy-$C_{1-3}$-alkyl, hydroxy-$C_{1-4}$-alkyl, or $CF_3$, particularly hydroxy, $C_{1-3}$-alkyl, $CF_3$, or hydroxy-$C_{1-3}$-alkyl.

If the partial formulae shown above are substituted as specified, the following definitions of the group $R^1R^2N$ are particularly preferred: hydroxypyrrolidinyl, hydroxypiperidinyl, 3,4-dihydroxypyrrolidinyl, 3,4-dihydroxypiperidinyl, 3,5-dihydroxypiperidinyl, (hydroxymethyl)pyrrolidinyl, (hydroxymethyl)piperidinyl, (hydroxymethyl)hydroxypyrrolidinyl, or (hydroxymethyl)hydroxypiperidinyl, while in the groups mentioned a hydroxymethyl group may be monoor disubstituted at the C atom by methyl, while two methyl substituents may be joined together, forming a cyclopropyl group, and in one or two hydroxy groups the H atom may be replaced by a methyl group, and the groups mentioned have no further substituents or have one or two substituents selected independently of one another from fluorine, hydroxy, $C_{1-3}$-alkyl, hydroxy-$C_{1-3}$-alkyl, and $CF_3$.

The following partial formulae are most particularly preferred definitions of the heterocyclic group

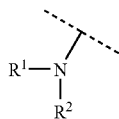

specified above:

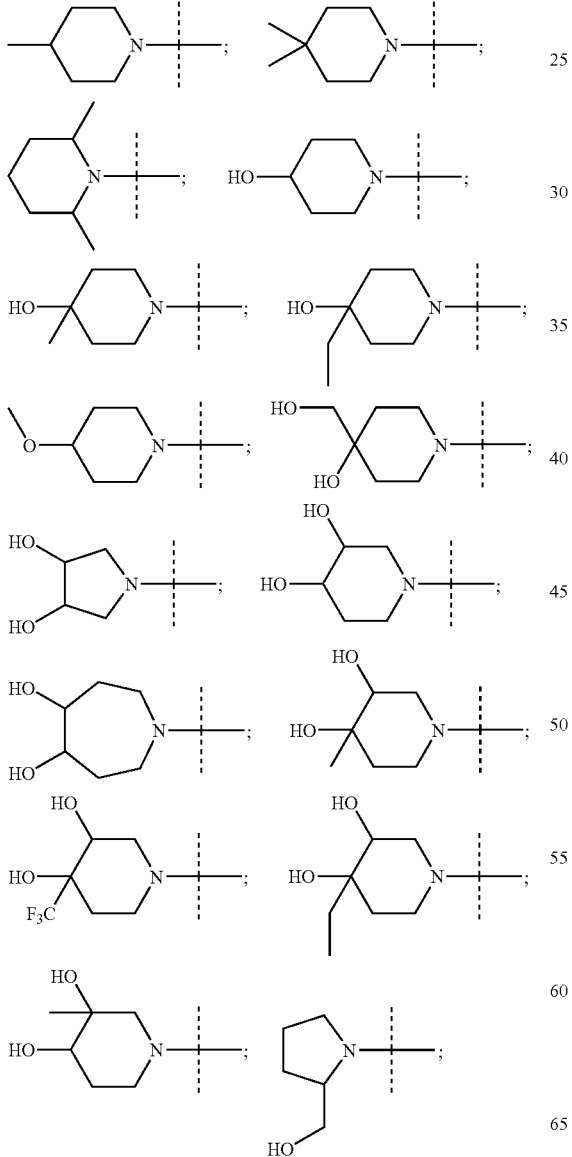

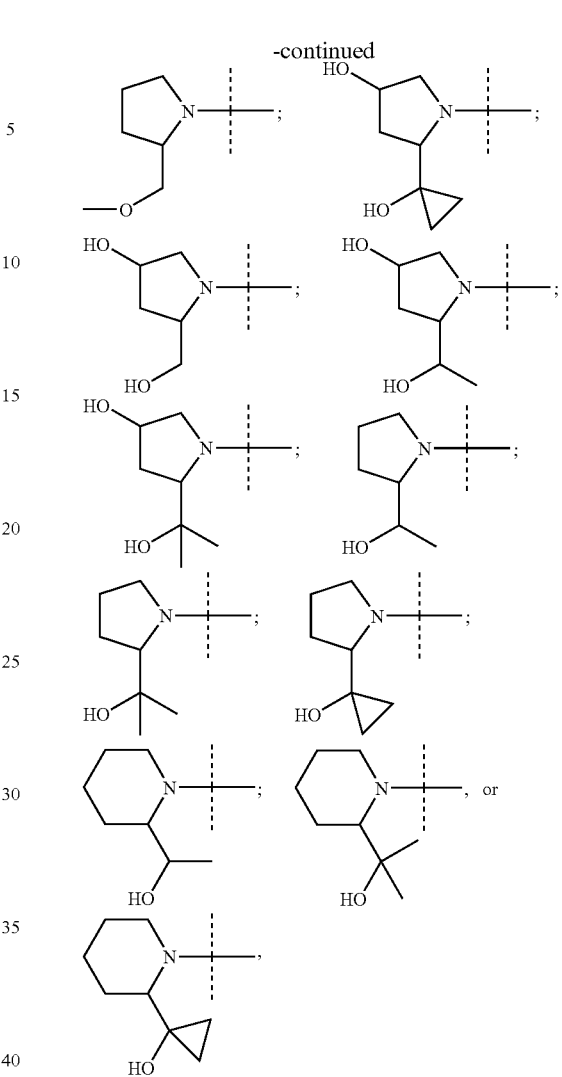

wherein the groups mentioned are not further substituted, or wherein methyl or ethyl groups may be mono-, di-, or trisubstituted by fluorine, and wherein one or more H atoms of the heterocycle formed by the group $R^1R^2N$— which are bound to carbon may be substituted independently of one another by fluorine, chlorine, CN, $CF_3$, $C_{1-3}$-alkyl, or hydroxy-$C_{1-3}$-alkyl, particularly $C_{1-3}$-alkyl or $CF_3$, preferably methyl, ethyl, or $CF_3$.

Among the abovementioned preferred and particularly preferred meanings of $R^1R^2N$, the following definitions of the substituent $R^{14}$ are preferred: F, Cl, Br, cyano, $C_{1-4}$-alkyl, $C_{2-4}$-alkenyl, $C_{2-4}$-alkynyl, $C_{3-7}$-cycloalkyl, $C_{3-7}$-cycloalkyl-$C_{1-3}$-alkyl, hydroxy, hydroxy-$C_{1-3}$-alkyl, $C_{1-4}$-alkoxy, ω-($C_{1-4}$-alkoxy)-$C_{1-3}$-alkyl, $C_{1-4}$-alkyl-carbonyl, carboxy, $C_{1-4}$-alkoxycarbonyl, hydroxy-carbonyl-$C_{1-3}$-alkyl, $C_{1-4}$-alkoxycarbonyl-$C_{1-3}$-alkyl, $C_{1-4}$-alkoxy-carbonylamino, $C_{1-4}$-alkoxy-carbonylamino-$C_{1-3}$-alkyl, amino, $C_{1-4}$-alkyl-amino, $C_{3-7}$-cycloalkyl-amino, N—($C_{3-7}$-cycloalkyl)-N—($C_{1-4}$-alkyl)-amino, di-($C_{1-4}$-alkyl)-amino, cyclo-$C_{3-6}$-alkyleneimino, amino-$C_{1-3}$-alkyl, $C_{1-4}$-alkyl-amino-$C_{1-3}$-alkyl, $C_{3-7}$-cycloalkyl-amino-$C_{1-3}$-alkyl, N—($C_{3-7}$-cycloalkyl)-N—($C_{1-4}$-alkyl)-amino-$C_{1-3}$-alkyl, di-($C_{1-4}$-alkyl)-amino-$C_{1-3}$-alkyl, cyclo-$C_{3-6}$-alkyleneimino-$C_{1-3}$-alkyl, aminocarbonyl, $C_{1-4}$-alkyl-aminocarbonyl, $C_{3-7}$-cycloalkyl-aminocarbonyl, N—($C_{3-7}$-cycloalkyl)-N—($C_{1-4}$-alkyl)- aminocarbonyl, di-($C_{1-4}$-alkyl)-aminocarbonyl, pyridinyloxy, pyridinylamino, or pyridinyl-$C_{1-3}$-alkyl-amino.

Particularly preferred meanings of the substituent $R^{14}$ are F, Cl, Br, $C_{1-4}$-alkyl, hydroxy, hydroxy-$C_{1-3}$-alkyl, $C_{1-4}$-alkoxy, ω-($C_{1-4}$-alkoxy)-$C_{1-3}$-alkyl, amino-$C_{1-3}$-alkyl, $C_{1-4}$-alkyl-amino-$C_{1-3}$-alkyl, $C_{3-7}$-cycloalkyl-amino-$C_{1-3}$-alkyl, N—($C_{3-7}$-cycloalkyl)-N—($C_{1-4}$-alkyl)-amino-$C_{1-3}$-alkyl, di-($C_{1-4}$-alkyl)-amino-$C_{1-3}$-alkyl, cyclo-$C_{3-6}$-alkyleneimino-$C_{1-3}$-alkyl, aminocarbonyl, and pyridylamino.

In the abovementioned preferred meanings of $R^{14}$ in each case one or more C atoms may additionally be mono- or polysubstituted by F and/or in each case one or two C atoms may independently of one another additionally be monosubstituted by Cl or Br. Thus, preferred meanings of $R^{14}$ also include, for example, —$CF_3$, —$OCF_3$, $CF_3$—CO—, and $CF_3$—CHOH—.

Most particularly preferred meanings of the substituent $R^{14}$ are $C_{1-3}$-alkyl, hydroxy-$C_{1-3}$-alkyl, methoxymethyl, hydroxy, $CF_3$, $CF_3$—CHOH—, particularly hydroxy, methyl, ethyl, $CF_3$, and hydroxymethyl.

The bridge W preferably denotes a single bond or ethylene, particularly preferably a single bond.

The bridge Z preferably denotes a single bond or ethylene which may have one or two methyl substituents which may be joined together, forming a cyclopropyl group. Particularly preferably Z denotes a single bond.

In the group Y, the groups K, L, and M preferably denote CH, while one or more CH groups may be substituted independently of one another by $R^{20}$.

According to another embodiment, one of the groups K, L, and M preferably denotes an N atom, while the other two groups selected from K, L, and M denote a CH group which may be substituted independently of one another by $R^{20}$.

Preferred definitions of the group Y are selected from the partial formulae:

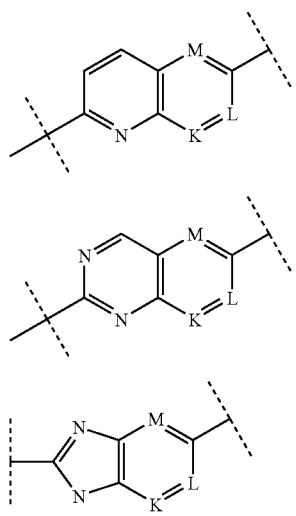

wherein the groups M, K, and L represent a CH group, while one of the groups M, K, and L may also represent an N atom, and in the partial formulae Y1, Y2, and Y6 one or more CH groups may be substituted independently of one another by $R^{20}$, and in partial formula Y6 an NH group may be substituted by $C_{1-4}$-alkyl.

Most particularly preferably the group Y denotes quinoline according to partial formula Y1, while K, L, and M denote a CH group, the quinoline group is preferably unsubstituted or one or more CH groups of the quinoline group are substituted independently of one another by $R^{20}$.

The group Y is preferably unsubstituted or mono- or disubstituted.

A most particularly preferred definition of the group Y is quinoline, which may be substituted, particularly in the 4-position. Therefore Y preferably denotes:

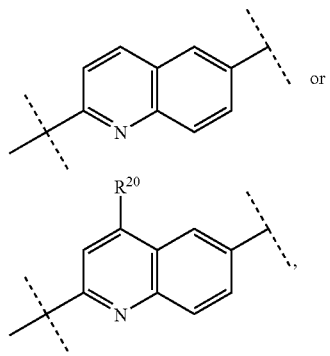

where $R^{20}$ is defined as below, and particularly denotes $C_{1-3}$-alkyl, and most particularly methyl.

Particularly preferred substituents $R^{20}$ of the group Y are selected from among fluorine, chlorine, bromine, cyano, nitro, $C_{1-4}$-alkyl, $C_{2-6}$-alkenyl, hydroxy, ω-hydroxy-$C_{1-3}$-alkyl, $C_{1-4}$-alkoxy, trifluoromethyl, trifluoromethoxy, $C_{2-4}$-alkynyl, $C_{1-4}$-alkoxycarbonyl, ω-($C_{1-4}$-alkoxy)-$C_{1-3}$-alkyl, $C_{1-4}$-alkoxy-carbonylamino, amino, $C_{1-4}$-alkyl-amino, di-($C_{1-4}$-alkyl)-amino, aminocarbonyl, $C_{1-4}$-alkyl-aminocarbonyl, and di-($C_{1-4}$-alkyl)-aminocarbonyl.

Most particularly preferred substituents $R^{20}$ of the group Y are selected from among fluorine, chlorine, bromine, cyano, $C_{1-3}$-alkyl, $C_{2-3}$-alkenyl, $C_{2-3}$-alkynyl, $C_{1-3}$-alkoxy, $C_{1-4}$-alkoxycarbonyl, trifluoromethyl, or trifluoromethoxy, or in the case of a phenyl ring nitro as well. Examples of most particularly preferred meanings of the substituent $R^{20}$ are F, Cl, Br, methyl, ethyl, acetyl, or methoxy.

Preferably the group A is selected from among the bivalent cyclic groups phenyl, pyridinyl, pyrimidinyl, pyrazinyl, or pyridazinyl, which may be mono- or polysubstituted at one or more C atoms by identical or different groups $R^{20}$, or in the case of a phenyl ring may also additionally be monosubstituted by nitro.

Most particularly preferably A is one of the following groups

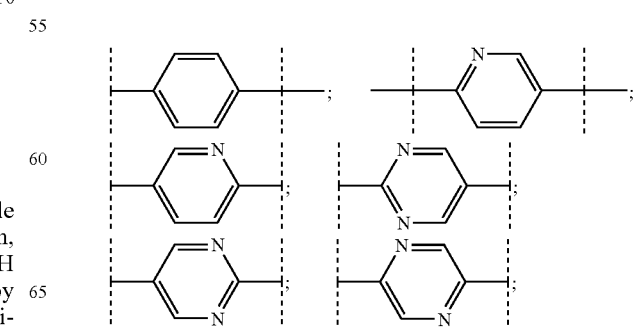

-continued

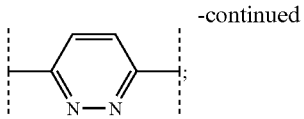

particularly

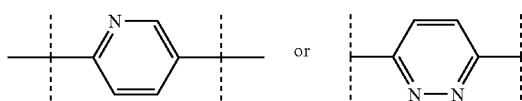

most particularly preferably

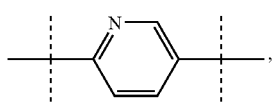

while the groups listed may be substituted as specified hereinbefore.

Particularly preferred substituents $R^{20}$ of the group A are, independently of one another, fluorine, chlorine, bromine, amino, $CF_3$, methoxy, and $C_{1-3}$-alkyl.

Preferably the group A is unsubstituted or monosubstituted by $R^{20}$, as specified.

Preferred definitions of the group B according to a first preferred embodiment are selected from the group comprising phenyl, pyridyl, thienyl, and furanyl. Particularly preferably the group B denotes phenyl. The group B with the meanings given may be mono- or polysubstituted by identical or different groups $R^{20}$, while a phenyl group may additionally also be monosubstituted by nitro. Preferably the group B is unsubstituted or mono-, di-, or trisubstituted, particularly unsubstituted or mono- or disubstituted. In the case of a monosubstitution, the substituent is preferably in the para-position to the group A.

Preferred substituents $R^{20}$ of the group B are selected from the group comprising fluorine, chlorine, bromine, cyano, nitro, $C_{1-4}$-alkyl, hydroxy, $CHF_2$, $CHF_2$—O—, hydroxy-$C_{1-3}$-alkyl, $C_{1-4}$-alkoxy, trifluoromethyl, trifluoromethoxy, $C_{2-4}$-alkynyl, carboxy, $C_{1-4}$-alkoxycarbonyl, ω-($C_{1-4}$-alkoxy)-$C_{1-3}$-alkyl, $C_{1-4}$-alkoxy-carbonylamino, amino, $C_{1-4}$-alkyl-amino, di-($C_{1-4}$-alkyl)-amino, cyclo-$C_{3-6}$-alkyleneimino, aminocarbonyl, $C_{1-4}$-alkyl-aminocarbonyl, and di-($C_{1-4}$-alkyl)-aminocarbonyl.

Particularly preferred substituents $R^{20}$ of the group B are selected from the group comprising fluorine, chlorine, bromine, cyano, $CF_3$, $C_{1-3}$-alkyl, $C_{1-4}$-alkoxy, and trifluoromethoxy.

Most particularly preferred substituents $R^{20}$ of the group B are selected from the group comprising chlorine, bromine, and methoxy.

According to a second embodiment the meaning of the group B is preferably selected from $C_{1-6}$-alkyl, $C_{2-6}$-alkenyl, $C_{2-6}$-alkynyl, $C_{3-7}$-cycloalkyl, $C_{5-7}$-cycloalkenyl, $C_{3-7}$-cycloalkyl-$C_{1-3}$-alkyl, $C_{3-7}$-cycloalkenyl-$C_{1-3}$-alkyl, $C_{3-7}$-cycloalkyl-$C_{1-3}$-alkenyl, and $C_{3-7}$-cycloalkyl-$C_{1-3}$-alkynyl, while one or more C atoms in the groups mentioned for B hereinbefore may be mono- or polysubstituted by fluorine. In the cyclic groups according to the abovementioned embodiment one or more C atoms may be substituted by $R^{20}$.

Particularly preferred according to this embodiment are the groups $C_{3-6}$-alkyl, $C_{3-6}$-alkenyl, $C_{3-6}$-alkynyl, cyclopentyl, cyclopentenyl, cyclohexyl, cyclohexenyl, cycloheptyl, cycloheptenyl, cyclopentyl-$C_{1-3}$-alkyl, cyclopentenyl-$C_{1-3}$-alkyl, cyclohexyl-$C_{1-3}$-alkyl, cyclohexenyl-$C_{1-3}$-alkyl, cycloheptyl-$C_{1-3}$-alkyl, and cycloheptenyl-$C_{1-3}$-alkyl, while one or more C atoms in the groups mentioned for B hereinbefore may be mono- or polysubstituted by fluorine, and in cyclic groups one or more C atoms may be substituted by identical or different $R^{20}$.

Most particularly preferably, according to this second embodiment B denotes cyclohexenyl which is unsubstituted or comprises 1, 2, or 3 identical or different substituents $R^{20}$, particularly methyl.

The following are preferred definitions of other substituents according to the invention:

Preferably the substituent $R^{13}$ has one of the meanings given for $R^{16}$. Particularly preferably $R^{13}$ denotes H, $C_{1-4}$-alkyl, $C_{3-7}$-cycloalkyl, $C_{3-7}$-cycloalkyl-$C_{1-3}$-alkyl, ω-hydroxy-$C_{2-3}$-alkyl, and ω-($C_{1-4}$-alkoxy)-$C_{2-3}$-alkyl. Most particularly preferably $R^{13}$ denotes H or $C_{1-4}$-alkyl. The alkyl groups mentioned hereinbefore may be monosubstituted by Cl or mono- or polysubstituted by F.

Preferred meanings of the substituent $R^{15}$ are H, $C_{1-4}$-alkyl, $C_{3-7}$-cycloalkyl, and $C_{3-7}$-cycloalkyl-$C_{1-3}$-alkyl, while, as defined hereinbefore, in each case one or more C atoms may additionally be mono- or polysubstituted by F and/or in each case one or two C atoms independently of one another may additionally be monosubstituted by Cl or Br. Particularly preferably $R^{15}$ denotes H, $CF_3$, methyl, ethyl, propyl, or butyl.

The substituent $R^{16}$ preferably denotes H, $C_{1-4}$-alkyl, $C_{3-7}$-cycloalkyl, $C_{3-7}$-cycloalkyl-$C_{1-3}$-alkyl, ω-hydroxy-$C_{2-3}$-alkyl, or ω-($C_{1-4}$-alkoxy)-$C_{2-3}$-alkyl, while, as hereinbefore defined, in each case one or more C atoms may additionally be mono- or polysubstituted by F and/or in each case one or two C atoms independently of one another may additionally be monosubstituted by Cl or Br. Particularly preferably $R^{16}$ denotes H, $CF_3$, $C_{1-3}$-alkyl, $C_{3-6}$-cycloalkyl, or $C_{3-6}$-cycloalkyl-$C_{1-3}$-alkyl.

Preferably the substituent $R^{17}$ has one of the meanings given for $R^{16}$ as being preferred or denotes phenyl, phenyl-$C_{1-3}$-alkyl, pyridinyl, or $C_{1-4}$-alkylcarbonyl. Particularly preferably $R^{17}$ has one of the meanings given for $R^{16}$ as being preferred.

Preferably one or both of the substituents $R^{18}$ and $R^{19}$ independently of one another denotes hydrogen or $C_{1-4}$-alkyl, particularly hydrogen.

The substituent $R^{20}$ preferably denotes halogen, hydroxy, cyano, $C_{1-4}$-alkyl, $C_{2-4}$-alkenyl, $C_{2-4}$-alkynyl, $C_{3-7}$-cycloalkyl, $C_{3-7}$-cycloalkyl-$C_{1-3}$-alkyl, hydroxy-$C_{1-4}$-alkyl, $R^{22}$—$C_{1-3}$-alkyl, or has one of the meanings given for $R^{22}$ as being preferred, while, as hereinbefore defined, in each case one or more C atoms may additionally be mono- or polysubstituted by F and/or in each case one or two C atoms independently of one another may additionally be monosubstituted by Cl or Br.

Particularly preferred definitions of the group $R^{20}$ are halogen, hydroxy, cyano, $C_{1-4}$-alkyl, $C_{1-4}$-alkylcarbonyl, $C_{3-7}$-cycloalkyl, and $C_{1-4}$-alkoxy, while, as hereinbefore defined, in each case one or more C atoms may additionally be mono- or polysubstituted by F and/or in each case one or two C atoms independently of one another may additionally be monosubstituted by Cl or Br. Most particularly preferably $R^{20}$ denotes F, Cl, Br, I, OH, cyano, methyl, difluoromethyl, trifluoromethyl, ethyl, n-propyl, isopropyl, acetyl, methoxy, difluoromethoxy, trifluoromethoxy, ethoxy, n-propoxy, or isopropoxy.

The substituent $R^{22}$ preferably denotes $C_{1-4}$-alkoxy, $C_{1-4}$-alkylthio, carboxy, $C_{1-4}$-alkylcarbonyl, $C_{1-4}$-alkoxycarbonyl, aminocarbonyl, $C_{1-4}$-alkylaminocarbonyl, di-($C_{1-4}$-alkyl)-aminocarbonyl, $C_{1-4}$-alkyl-sulfonyl, $C_{1-4}$-alkyl-sulfinyl, $C_{1-4}$-alkyl-sulfonylamino, amino, $C_{1-4}$-alkylamino, di-($C_{1-4}$-alkyl)-amino, $C_{1-4}$-alkyl-carbonylamino, hydroxy-$C_{1-3}$-alkylaminocarbonyl, aminocarbonyl-amino, or $C_{1-4}$-alkylaminocarbonylamino, while, as hereinbefore defined, in each case one or more C atoms may additionally be mono- or polysubstituted by F and/or in each case one or two C atoms independently of one another may additionally be monosubstituted by Cl or Br. Most particularly preferred meanings for $R^{22}$ are $C_{1-4}$-alkoxy, $C_{1-4}$-alkylcarbonyl, amino, $C_{1-4}$-alkylamino, and di-($C_{1-4}$-alkyl)-amino, wherein one or more H atoms may be replaced by fluorine.

Preferred definitions of the group $R^{21}$ are $C_{1-4}$-alkyl, $C_{1-4}$-alkylcarbonyl, $C_{1-4}$-alkylsulfonyl, —$SO_2$—$NH_2$, —$SO_2$—$NH$-$C_{1-3}$-alkyl, —$SO_2$—$N(C_{1-3}$-alkyl$)_2$, and cyclo-$C_{3-6}$-alkyleneimino-sulfonyl, while, as hereinbefore defined, in each case one or more C atoms may additionally be mono- or polysubstituted by F and/or in each case one or two C atoms independently of one another may additionally be monosubstituted by Cl or Br. Most particularly preferably $R^{21}$ denotes $C_{1-4}$-alkyl or $CF_3$.

Cy preferably denotes a $C_{3-7}$-cycloalkyl, particularly a $C_{3-6}$-cycloalkyl group, a $C_{5-7}$-cycloalkenyl group, pyrrolidinyl, piperidinyl, piperazinyl, morpholinyl, thiomorpholinyl, aryl, or heteroaryl, and the abovementioned cyclic groups may be mono- or polysubstituted at one or more C atoms by identical or different groups $R^{20}$, or in the case of a phenyl group may also additionally be monosubstituted by nitro, and/or one or more NH groups may be substituted by $R^{21}$. Most particularly preferred definitions of the group Cy are $C_{3-6}$-cycloalkyl, pyrrolidinyl, and piperidinyl, which may be substituted as specified.

The term aryl preferably denotes phenyl or naphthyl, particularly phenyl.

The term heteroaryl preferably comprises pyridyl, indolyl, quinolinyl, and benzoxazolyl.

Preferred compounds according to the invention are those wherein one or more of the groups, radicals, substituents and/or indices have one of the meanings given hereinbefore as being preferred.

Particularly preferred compounds according to the invention may be described by a general formula IIa, IIb, IIc and IId, particularly IIa and IIb,

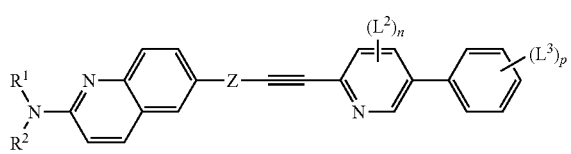

IIa

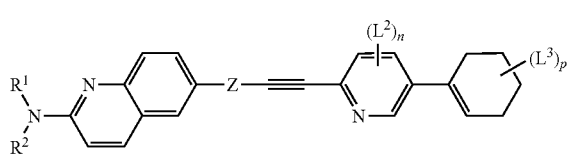

IIb

-continued

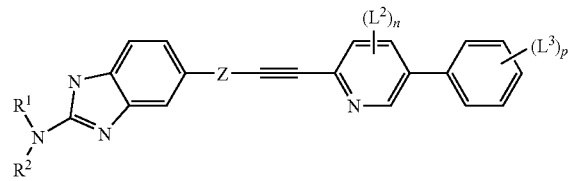

IIc

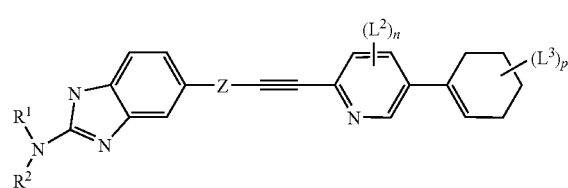

IId wherein:

the quinoline and benzimidazole groups are unsubstituted or mono- or disubstituted by $L^1$, while a quinoline group is preferably unsubstituted or monosubstituted in the 4-position by $R^{20}$, particularly $C_{1-3}$-alkyl, most particularly methyl;

$R^1$, $R^2$, and Z have one of the abovementioned meanings;

$L^1$, $L^2$, and $L^3$ independently of one another have one of the meanings given for $R^{20}$; and n and p independently of one another represent the values 0, 1, or 2, and p also denotes the value 3.

In particular in formulae IIa, IIb, IIc, and IId, preferably IIa and IIb,

Z denotes a single bond;

$L^1$ denotes fluorine, chlorine, bromine, cyano, $C_{1-3}$-alkyl, $C_{1-3}$-alkoxy, $C_{1-4}$-alkoxycarbonyl, trifluoromethyl, trifluoromethoxy, or nitro, particularly $C_{1-3}$-alkyl;

$L^2$ denotes fluorine, chlorine, bromine, CN, amino, $CF_3$, methoxy, or $C_{1-3}$-alkyl;

n denotes 0 or 1;

$L^3$ are selected independently of one another from the meanings fluorine, chlorine, bromine, cyano, nitro, $C_{1-4}$-alkyl, hydroxy, ω-hydroxy-$C_{1-3}$-alkyl, $C_{1-4}$-alkoxy, trifluoromethyl, trifluoromethoxy, $C_{2-4}$-alkynyl, carboxy, $C_{1-4}$-alkoxycarbonyl, ω-($C_{1-4}$-alkoxy)-$C_{1-3}$-alkyl, $C_{1-4}$-alkoxycarbonylamino, amino, $C_{1-4}$-alkyl-amino, di-($C_{1-4}$-alkyl)-amino, cyclo-$C_{3-6}$-alkyleneimino, aminocarbonyl, $C_{1-4}$-alkyl-aminocarbonyl, or di-($C_{1-4}$-alkyl)-aminocarbonyl, particularly preferred are fluorine, chlorine, bromine, cyano, $CF_3$, $C_{1-3}$-alkyl, $C_{1-4}$-alkoxy, and trifluoromethoxy, with the proviso that a phenyl ring may only be monosubstituted by nitro; and p denotes 0, 1, 2, or 3, particularly 1 or 2.

Most particularly preferably in formulae IIa, IIb, IIc, and IId, particularly IIa and IIb, $R^1$ and $R^2$ independently of one another denote $C_{1-4}$-alkyl, hydroxy-$C_{1-4}$-alkyl, $C_{3-5}$-alkenyl, $C_{3-5}$-alkynyl, $C_{3-7}$-cycloalkyl, hydroxy-$C_{3-7}$-cycloalkyl, dihydroxy-$C_{3-6}$-alkyl, $C_{3-7}$-cycloalkyl-$C_{1-3}$-alkyl, tetrahydropyran-3-yl, tetrahydropyran-4-yl, tetrahydrofuran-2-ylmethyl, tetrahydrofuran-3-ylmethyl, (hydroxy-$C_{3-7}$-cycloalkyl)-$C_{1-3}$-alkyl, ω-($C_{1-4}$-alkoxy)-$C_{2-3}$-alkyl, di-($C_{1-3}$-alkyl)amino-$C_{2-3}$-alkyl, pyrrolidine-N-yl-$C_{2-3}$-alkyl, piperidin-N-yl-$C_{2-3}$-alkyl, pyridyl, or benzyl, while an alkyl, cycloalkyl, or cycloalkyl-alkyl group may additionally be mono- or disubstituted by hydroxy and/or hydroxy-$C_{1-3}$-alkyl, and/or mono- or polysubstituted by F or $C_{1-3}$-alkyl and/or monosubstituted by $CF_3$, Br, Cl, or CN, and one or both, preferably one of the groups $R^1$ and $R^2$ may also represent H, and phenyl and pyridyl rings may be mono- or polysubstituted by identical or different groups $R^{20}$, and phenyl may also be monosubstituted by nitro, or $R^1$ and $R^2$ are joined together and form together with the N atom to which they are bound a heterocyclic group which is selected from pyrrolidine, piperidine, piperazine wherein the free imine function is substituted by $R^{13}$, and morpholine, wherein one or more H atoms may be replaced by identical or different groups $R^{14}$, and the heterocyclic group defined hereinbefore may be substituted via a single bond by a carbo- or heterocyclic group Cy, while Cy is selected from the group comprising $C_{3-7}$-cycloalkyl and cyclo-$C_{3-6}$-alkyleneimino, while Cy may be mono- or polysubstituted by identical or different groups $R^{20}$, where $R^{20}$ is as hereinbefore defined and is preferably selected from fluorine, $CF_3$, $C_{1-3}$-alkyl, hydroxy-$C_{1-3}$-alkyl, and hydroxy; and $R^{14}$ is selected from F, Cl, Br, $C_{1-4}$-alkyl, hydroxy, hydroxy-$C_{1-3}$-alkyl, $C_{1-4}$-alkoxy, ω-($C_{1-4}$-alkoxy)-$C_{1-3}$-alkyl, amino-$C_{1-3}$-alkyl, $C_{1-4}$-alkyl-amino-$C_{1-3}$-alkyl, $C_{3-7}$-cycloalkyl-amino-$C_{1-3}$-alkyl, N—($C_{3-7}$-cycloalkyl)-N—($C_{1-4}$-alkyl)-amino-$C_{1-3}$-alkyl, di-($C_{1-4}$-alkyl)-amino-$C_{1-3}$-alkyl, cyclo-$C_{3-6}$-alkyleneimino-$C_{1-3}$-alkyl, aminocarbonyl; and pyridylamino, while in the abovementioned meanings in each case one or more C atoms may additionally be mono- or polysubstituted by F and/or in each case one or two C atoms independently of one another may additionally be monosubstituted by Cl or Br.

The compounds listed in the experimental section, including the tautomers, the diastereomers, the enantiomers, the mixtures thereof, and the salts thereof, are preferred according to the invention.

Some expressions used hereinbefore and below to describe the compounds according to the invention will now be defined more fully.

The term halogen denotes an atom selected from among F, Cl, Br, and I, particularly F, Cl, and Br.

The term $C_{1-n}$-alkyl, where n has a value of 3 to 8, denotes a saturated, branched or unbranched hydrocarbon group with 1 to n C atoms. Examples of such groups include methyl, ethyl, n-propyl, isopropyl, butyl, isobutyl, sec-butyl, tert-butyl, n-pentyl, isopentyl, neopentyl, tert-pentyl, n-hexyl, isohexyl, etc.

The term $C_{1-n}$-alkylene, where n may have a value of 1 to 8, denotes a saturated, branched or unbranched hydrocarbon bridge with 1 to n C atoms. Examples of such groups include methylene (—$CH_2$—), ethylene (—$CH_2$—$CH_2$—), 1-methylethylene (—CH($CH_3$)—$CH_2$—), 1,1-dimethylethylene (—C($CH_3$)$_2$—$CH_2$—), n-prop-1,3-ylene (—$CH_2$—$CH_2$—$CH_2$—), 1-methylprop-1,3-ylene (—CH($CH_3$)—$CH_2$—$CH_2$—), 2-methylprop-1,3-ylene (—$CH_2$—CH($CH_3$)—$CH_2$—), etc., as well as the corresponding mirror-symmetrical forms.

The term $C_{2-n}$-alkenyl, where n has a value of 3 to 6, denotes a branched or unbranched hydrocarbon group with 2 to n C atoms and at least one C=C-double bond. Examples of such groups include vinyl, 1-propenyl, 2-propenyl, isopropenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 2-hexenyl, 3-hexenyl, 4-hexenyl, 5-hexenyl, etc.

The term $C_{2-n}$-alkynyl, where n has a value of 3 to 6, denotes a branched or unbranched hydrocarbon group with 2 to n C atoms and a C≡C triple bond. Examples of such groups include ethynyl, 1-propynyl, 2-propynyl, isopropynyl, 1-butynyl, 2-butynyl, 3-butynyl, 2-methyl-1-propynyl, 1-pentynyl, 2-pentynyl, 3-pentynyl, 4-pentynyl, 3-methyl-2-butynyl, 1-hexynyl, 2-hexynyl, 3-hexynyl, 4-hexynyl, 5-hexynyl, etc.

The term $C_{2-n}$-alkoxy denotes a $C_{1-n}$-alkyl-O— group, wherein $C_{1-n}$-alkyl is defined as above. Examples of such groups include methoxy, ethoxy, n-propoxy, isopropoxy, n-butoxy, isobutoxy, sec-butoxy, tert-butoxy, n-pentoxy, isopentoxy, neopentoxy, tert-pentoxy, n-hexoxy, isohexoxy, etc.

The term $C_{1-n}$-alkylthio denotes a $C_{1-n}$-alkyl-S— group, wherein $C_{1-n}$-alkyl is defined as above. Examples of such groups include methylthio, ethylthio, n-propylthio, isopropylthio, n-butylthio, isobutylthio, sec-butylthio, tert-butylthio, n-pentylthio, isopentylthio, neopentylthio, tert-pentylthio, n-hexylthio, isohexylthio, etc.

The term $C_{1-n}$-alkylcarbonyl denotes a $C_{1-n}$-alkyl—C(=O)— group, wherein $C_{1-n}$-alkyl is defined as above. Examples of such groups include methylcarbonyl, ethylcarbonyl, n-propylcarbonyl, isopropylcarbonyl, n-butylcarbonyl, isobutylcarbonyl, sec-butylcarbonyl, tert-butylcarbonyl, n-pentylcarbonyl, isopentylcarbonyl, neopentylcarbonyl, tert-pentylcarbonyl, n-hexylcarbonyl, isohexylcarbonyl, etc.

The term $C_{3-n}$-cycloalkyl denotes a saturated mono-, bi-, tri-, or spirocarbocyclic, preferably monocarbocyclic group with 3 to n C atoms. Examples of such groups include cyclopropyl, cyclobutyl, cyclopentyl, cyclohexyl, cycloheptyl, cyclooctyl, cyclononyl, cyclododecyl, bicyclo[3,2,1]octyl, spiro[4,5]decyl, norpinyl, norbonyl, norcaryl, adamantyl, etc.

The term $C_{5-n}$-cycloalkenyl denotes a monounsaturated mono-, bi-, tri-, or spirocarbocyclic, preferably monocarboxylic group with 5 to n C atoms. Examples of such groups include cyclopentenyl, cyclohexenyl, cycloheptenyl, cyclooctenyl, cyclononenyl, etc.

The term $C_{3-n}$-cycloalkylcarbonyl denotes a $C_{3-n}$-cycloalkyl-C(=O) group, wherein $C_{3-n}$-cycloalkyl is as hereinbefore defined.

The term aryl denotes a carbocyclic, aromatic ring system, such as, for example, phenyl, biphenyl, naphthyl, anthracenyl, phenanthrenyl, fluorenyl, indenyl, pentalenyl, azulenyl, biphenylenyl, etc. A particularly preferred meaning of "aryl" is phenyl.

The term cyclo-$C_{3-6}$-alkyleneimino denotes a 4- to 7-membered ring which comprises 3 to 6 methylene units as well as an imino group, while the bond to the residue of the molecule is made via the imino group.

The term cyclo-$C_{3-6}$-alkyleneimino-carbonyl denotes a cyclo-$C_{3-6}$-alkyleneimino ring as hereinbefore defined which is linked to a carbonyl group via the imino group.

The term heteroaryl used in this application denotes a heterocyclic, aromatic ring system which comprises in addition to at least one C atom one or more heteroatoms selected from N, O and/or S. Examples of such groups are furanyl, thiophenyl, pyrrolyl, oxazolyl, thiazolyl, imidazolyl, isoxazolyl, isothiazolyl, 1,2,3-triazolyl, 1,3,5-triazolyl, pyranyl, pyridyl, pyridazinyl, pyrimidinyl, pyrazinyl, 1,2,3-triazinyl, 1,2,4-triazinyl, 1,3,5-triazinyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, thiadiazinyl, indolyl, isoindolyl, benzofuranyl, benzothiophenyl (thianaphthenyl), indazolyl, benzimidazolyl, benzthiazolyl, benzisothiazolyl, benzoxazolyl, benzisoxazolyl, purinyl, quinazolinyl, quinozilinyl, quinolinyl, isoquinolinyl, quinoxalinyl, naphthyridinyl, pteridinyl, carbazolyl, azepinyl, diazepinyl, acridinyl, etc. The term heteroaryl also comprises the partially hydrogenated heterocyclic, aromatic ring systems, particularly those listed above. Examples of such partially hydrogenated ring systems are 2,3-dihydrobenzofuranyl, pyrolinyl, pyrazolinyl, indolinyl, oxazolidinyl, oxazolinyl, oxazepinyl, etc. Particularly preferably heteroaryl denotes a heteroaromatic mono- or bicyclic ring system.

Terms such as $C_{3-7}$-cycloalkyl-$C_{1-n}$-alkyl, heteroaryl-$C_{1-n}$-alkyl, etc. refer to $C_{1-n}$-alkyl, as defined above, which is substituted with a $C_{3-7}$-cycloalkyl, aryl or heteroaryl group.

Many of the terms given above may be used repeatedly in the definition of a formula or group and in each case have one of the meanings given above, independently of one another. Thus, for example, in the group di-$C_{1-4}$-alkyl-amino, the two alkyl groups may have the same or different meanings.

The term "unsaturated", for example, in "unsaturated carbocyclic group" or "unsaturated heterocyclic group", as used particularly in the definition of the group Cy, comprises in addition to the mono- or polyunsaturated groups, the corresponding, totally unsaturated groups, but particularly the mono- and diunsaturated groups.

The term "optionally substituted" used in this application indicates that the group thus designated is either unsubstituted or mono- or polysubstituted by the substituents specified. If the group in question is polysubstituted, the substituents may be identical or different.

The style used hereinbefore and hereinafter, according to which in a cyclic group a bond of a substituent is shown towards the centre of this cyclic group, indicates unless otherwise stated that this substituent may be bound to any free position of the cyclic group carrying an H atom.

Thus in the example

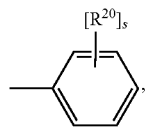

the substituent $R^{20}$ where s=1 may be bound to any of the free positions of the phenyl ring; where s=2 selected substituents $R^{20}$ may independently of one another be bound to different free positions of the phenyl ring.

The H atom of any carboxy group present or an H atom bound to an N atom (imino or amino group) may in each case be replaced by a group which can be cleaved in vivo. By a group which can be cleaved in vivo from an N atom is meant, for example, a hydroxy group, an acyl group such as the benzoyl or pyridinoyl group or a $C_{1-16}$-alkanoyl group such as the formyl, acetyl, propionyl, butanoyl, pentanoyl, or hexanoyl group, an allyloxycarbonyl group, a $C_{1-16}$-alkoxycarbonyl group such as the methoxycarbonyl, ethoxycarbonyl, propoxycarbonyl, isopropoxycarbonyl, butoxycarbonyl, tert-butoxycarbonyl, pentoxycarbonyl, hexyloxycarbonyl, octyloxycarbonyl, nonyloxycarbonyl, decyloxycarbonyl, undecyloxycarbonyl, dodecyloxycarbonyl, or hexadecyloxycarbonyl group, a phenyl-$C_{1-6}$-alkoxycarbonyl group such as the benzyloxycarbonyl, phenylethoxycarbonyl, or phenylpropoxycarbonyl group, a $C_{1-3}$-alkylsulfonyl-$C_{2-4}$-alkoxycarbonyl, $C_{1-3}$-alkoxy-$C_{2-4}$-alkoxy-$C_{2-4}$-alkoxy-carbonyl, or $R_eCO-O-(R_fCR_g)-O-CO-$ group wherein $R_e$ denotes a $C_{1-8}$-alkyl, $C_{5-7}$-cycloalkyl, phenyl, or phenyl-$C_{1-3}$-alkyl group, $R_f$ denotes a hydrogen atom, a $C_{1-3}$-alkyl, $C_{5-7}$-cycloalkyl, or phenyl group and $R_g$ denotes a hydrogen atom, a $C_{1-3}$-alkyl, or $R_eCO-O-(R_fCR_h)-O$ group wherein $R_e$ and $R_f$ are as hereinbefore defined and $R_h$ is a hydrogen atom or a $C_{1-3}$-alkyl group, while the phthalimido group is an additional possibility for an amino group, and the abovementioned ester groups may also be used as a group which can be converted in vivo into a carboxy group.

The residues and substituents described above may be mono- or polysubstituted by fluorine as described. Preferred fluorinated alkyl groups are fluoromethyl, difluoromethyl, and trifluoromethyl. Preferred fluorinated alkoxy groups are fluoromethoxy, difluoromethoxy, and trifluoromethoxy. Preferred fluorinated alkylsulfinyl and alkylsulfonyl groups are trifluoromethylsulfinyl and trifluoromethylsulfonyl.

The compounds of general formula I according to the invention may have acid groups, predominantly carboxyl groups, and/or basic groups such as, e.g., amino functions. Compounds of general formula I may therefore be present as internal salts, as salts with pharmaceutically useable inorganic acids such as hydrochloric acid, sulfuric acid, phosphoric acid, sulfonic acid, or organic acids (such as, for example, maleic acid, fumaric acid, citric acid, tartaric acid, or acetic acid) or as salts with pharmaceutically useable bases such as alkali or alkaline earth metal hydroxides or carbonates, zinc or ammonium hydroxides, or organic amines such as, e.g., diethylamine, triethylamine, or triethanolamine inter alia.

The compounds according to the invention may be obtained using methods of synthesis which are known in principle. Preferably the compounds are obtained analogously to the methods of preparation explained more fully hereinafter.

The two reaction plans A and B that follow show the synthesis of the compounds A.5 and B.5 according to the invention, while $R^1$, $R^2$, X, Y, Z, W, A, and B have one of the meanings described hereinbefore. Hal denotes chlorine, bromine, or iodine, particularly bromine or iodine, particularly preferably iodine.

According to Reaction Plan A, the halogen compound A.1 is reacted with the alkyne compound A.2 in a molar ratio of about 1.5:1 to 1:1.5 under a protective has atmosphere in the presence of a suitable palladium catalyst, a suitable base, and copper (I) iodide in a suitable solvent. A preferred amount of copper (I) iodide is in the range from 1 to 15 mol %, particularly 5 to 10 mol % based on the educt A.1. Suitable palladium catalysts are, for example, $Pd(PPh_3)_4$, $Pd_2(dba)_3$, $Pd(OAc)_2$, $Pd(PPh_3)_2Cl_2$, $Pd(CH_3CN)_2Cl_2$, and $Pd(dppf)Cl_2$. The palladium catalyst is preferably used in an amount from 1 to 15 mol %, particularly 5 to 10 mol % based on the educt A.1. Suitable bases are particularly amines, such as, for example, triethylamine or ethyldiisopropylamine, as well as $Cs_2CO_3$. The base is preferably used in an at least equimolar amount based on the educt A.1, in excess or as the solvent. Moreover, suitable solvents are dimethylformamide or ether, such as, for example, tetrahydrofuran, including the mixtures thereof. The reaction takes place over a period of about 2 to 24 hours in a temperature range of about 20° C. to 90° C.

The alkyne compound A.3 obtained is reacted directly or after prior purification with a suitable halogenating agent to obtain the halide derivative A.4, wherein Hal' denotes chlorine, bromine, or iodine. Suitable halogenating agents include, for example, $POCl_3$ or $N(butyl)_4Br$ with $P_2O_5$. The reaction conditions required are known to the skilled person as such. Suitable reaction temperatures are usually in the range from 15° C. to 150° C.

The reaction solution containing the halide derivative A.4 or the purified halide derivative A.4, dissolved in a suitable solvent, is reacted with an amine H—NR$^1$R$^2$ to yield the end product A.5 and then optionally purified. If the amine H—NR$^1$R$^2$ has another primary or secondary amino function, this is advantageously provided with a protective group beforehand, which can be cleaved again after the reaction has ended, using methods known from the literature. The product thus obtained may, for example, be converted into the salt form by reaction with a corresponding acid. A preferred molar ratio of the derivative A.4 to the amine compound is in the range from 1.5:1 to 1:1.5. Suitable solvents are dimethylformamide or ether, such as, for example, tetrahydrofuran, including the mixtures thereof. The reaction to form the product A.5 is advantageously carried out in a temperature range from about 20° C. to 90° C.

Reaction Plan A:

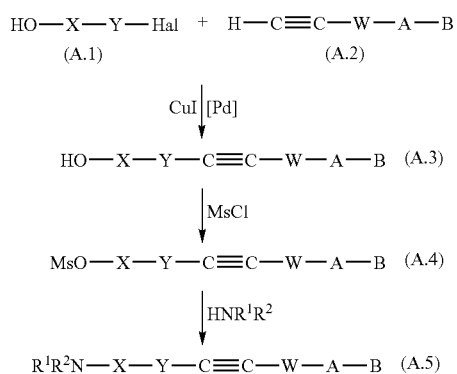

According to Reaction Plan B, the halogen compound B.2 is reacted with the alkyne compound B.1 in a molar ratio of about 1.5:1 to 1:1.5 under a protective gas atmosphere in the presence of a suitable palladium catalyst, a suitable base, and copper (I) iodide in a suitable solvent. Information on suitable reaction conditions, including catalysts, bases, and solvents, may be found in the explanations of Reaction Plan A.

The alkyne compound B.3 obtained is reacted directly or after prior purification with a suitable halogenating agent to obtain the halide derivative B.4, wherein Hal' denotes chlorine, bromine, or iodine. The reaction conditions to be respected can again be found in the remarks accompanying Reaction Plan A.

The reaction solution containing the halide derivative B.4 or the purified halide derivative B.4, dissolved in a suitable solvent, is reacted with an amine H—NR$^1$R$^2$ to yield the end product B.5 and then optionally purified. Here again, the remarks concerning Reaction Plan A apply.

Reaction Plan B:

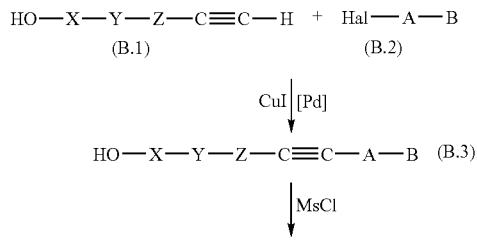

-continued

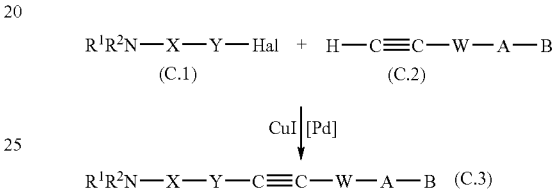

According to the other Reaction Plan C, the halogen compound C.1 is reacted with the alkyne compound C.2 in a molar ratio of about 1.5:1 to 1:1.5 under a protective gas atmosphere in the presence of a suitable palladium catalyst, a suitable base, and copper (I) iodide in a suitable solvent to form the product C.3 directly. Information on suitable reaction conditions, including catalysts, bases, and solvents, may be found in the explanatory remarks accompanying Reaction Plan A.

Reaction Plan C:

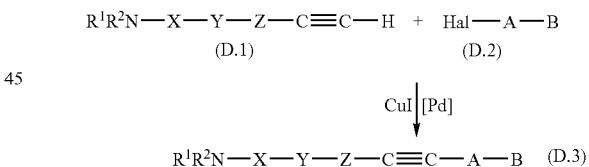

An alternative method of synthesis to this is shown in Reaction Plan D. According to this, the halogen compound D.2 is reacted with the alkyne compound D.1 in a molar ratio of about 1.5:1 to 1:1.5 under a protective gas atmosphere in the presence of a suitable palladium catalyst, a suitable base, and copper (I) iodide in a suitable solvent to form the product D.3 directly. Once again, information on suitable reaction conditions, including catalysts, bases, and solvents, may be found in the explanatory remarks accompanying Reaction Plan A.

Reaction Plan D:

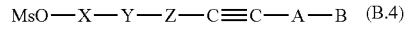
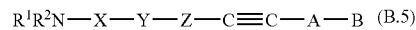

The reactions according to Plans A, B, C, and D are particularly advantageously carried out with the corresponding iodine compounds A.1, B.2, C.1, and D.2. In the event that Hal denotes bromine in compounds A.1, B.2, C.1, or D.2, it is advantageous to convert it into the corresponding iodine compound beforehand. One particularly advantageous method is the Aryl-Finkelstein reaction (Artis Klapars and Stephen L. Buchwald, *Copper-Catalyzed Halogen Exchange in Aryl Halides: An Aromatic Finkelstein Reaction*, J. Am. Chem. Soc. (2002), 124 (50), pp. 14844-14845). Thus, for example, the halogen compound A.1, B.2, C.1, or D.2 may be reacted with sodium iodide in the presence of N,N'-dimethylethylenediamine and copper (I) iodide in a suitable solvent to form the corresponding iodine compound. An advantageous molar ratio of the halogen compound to sodium iodide is 1:1.8 to 1:2.3. N,N'-dimethylethylenediamine is advantageously used in a molar ratio of 10 to 30 mol % based on the halogen compound A.1, B.2, C.1, or D.2. Preferred amounts of copper (I) iodide are in the range from 5 to 20 mol % based on the halogen compound A.1, B.2, C.1, or D.2. A suitable solvent is, for example, 1,4-dioxane. Suitable reaction temperatures are in the range from about 20° C. to 1 10° C. The reaction is substantially complete after 2 to 72 hours.

The compounds according to the invention may be obtained using methods of synthesis which are known in principle. Preferably the compounds are obtained analogously to the methods of preparation explained more filly in the experimental section.

Stereoisomeric compounds according to the present invention may chiefly be separated by conventional methods. The diastereomers are separated on the basis of their different physiCO—Chemical properties, e.g., by fractional crystallization from suitable solvents, by high pressure liquid or column chromatography, using chiral or preferably non-chiral stationary phases. Racemates may be separated, for example, by HPLC on suitable chiral stationary phases (e.g., Chiral AGP, CHIRALPAK® AD). Racemates which contain a basic or acidic function can also be separated via the diastereomeric, optically active salts which are produced on reacting with an optically active acid, for example, (+) or (−)-tartaric acid, (+) or (−)-diacetyl tartaric acid, (+) or (−)-monomethyl tartrate, or (+)-camphorsulfonic acid, or an optically active base, for example, with (R)-(+)-1-phenylethylamine, (S)-(−)-1-phenylethylamine, or (S)-brucine.

According to a conventional method of separating isomers, the racemate of a compound according to the invention is reacted with one of the abovementioned optically active acids or bases in equimolar amounts in a solvent and the resulting crystalline, diastereomeric, optically active salts thereof are separated using their different solubilities. This reaction may be carried out in any type of solvent provided that it is sufficiently different in terms of the solubility of the salts. Preferably, methanol, ethanol, or mixtures thereof, for example, in a ratio by volume of 50:50, are used. Then each of the optically active salts is dissolved in water, carefully neutralized with a base such as sodium carbonate or potassium carbonate, or with a suitable acid, e.g., with dilute hydrochloric acid or aqueous methanesulfonic acid and in this way the corresponding free compound is obtained in the (+) or (−) form.

The (R) or (S) enantiomer alone or a mixture of two optically active diastereomeric compounds according to the invention may also be obtained by performing the syntheses described above with a suitable reaction component in the (R) or (S) configuration.

As already mentioned, the compounds of formula (I) may be converted into the salts thereof, particularly for pharmaceutical use into the physiologically and pharmacologically acceptable salts thereof. These salts may be present on the one hand as physiologically and pharmacologically acceptable acid addition salts of the compounds of formula (I) with inorganic or organic acids. The acid addition salts may be prepared, for example, using hydrochloric acid, hydrobromic acid, sulfuric acid, phosphoric acid, methanesulfonic acid, ethanesulfonic acid, toluenesulfonic acid, benzenesulfonic acid, acetic acid, fumaric acid, succinic acid, lactic acid, citric acid, tartaric acid, or maleic acid. Moreover, mixtures of the abovementioned acids may be used.

The compounds according to the present invention, including the physiologically acceptable salts, are effective as antagonists of the MCH receptor, particularly the MCH-1 receptor, and exhibit good affinity in MCH receptor binding studies. Pharmacological test systems for MCH-antagonistic properties are described in the following experimental section.

As antagonists of the MCH receptor the compounds according to the invention are advantageously suitable as pharmaceutical active substances for the prevention and/or treatment of symptoms and/or diseases caused by MCH or causally connected with MCH in some other way. Generally the compounds according to the invention have low toxicity, they are well absorbed by oral route and have good intracerebral transitivity, particularly brain accessibility.

Therefore, MCH antagonists which contain at least one compound according to the invention are particularly suitable in mammals, such as, for example, rats, mice, guinea pigs, hares, dogs, cats, sheep, horses, pigs, cattle, monkeys, and humans, for the treatment and/or prevention of symptoms and/or diseases which are caused by MCH or are otherwise causally connected with MCH.

Diseases caused by MCH or otherwise causally connected with MCH are particularly metabolic disorders, such as, for example, obesity, and eating disorders, such as, for example, bulimia, including bulimia nervosa. The indication obesity includes in particular exogenic obesity, hyperinsulinemic obesity, hyperplasmic obesity, hyperphyseal adiposity, hypoplasmic obesity, hypothyroid obesity, hypothalamic obesity, symptomatic obesity, infantile obesity, upper body obesity, alimentary obesity, hypogonadal obesity, central obesity. This range of indications also includes cachexia, anorexia, and hyperphagia.

Compounds according to the invention may be particularly suitable for reducing hunger, curbing appetite, controlling eating behavior and/or inducing a feeling of satiation.

In addition, the diseases caused by MCH or otherwise causally connected with MCH also include hyperlipidemia, cellulitis, fatty accumulation, malignant mastocytosis, systemic mastocytosis, emotional disorders, affectivity disorders, depression, anxiety states, reproductive disorders, sexual disorders, memory disorders, epilepsy, forms of dementia, and hormonal disorders.

Compounds according to the invention are also suitable as active substances for the prevention and/or treatment of other illnesses and/or disorders, particularly those which accompany obesity, such as, for example, diabetes, diabetes mellitus, particularly type II diabetes, hyperglycemia, particularly chronic hyperglycemia, complications of diabetes including diabetic retinopathy, diabetic neuropathy, diabetic nephropathy, etc., insulin resistance, pathological glucose tolerance, encephalorrhagia, cardiac insufficiency, cardiovascular diseases, particularly arteriosclerosis and high blood pressure, arthritis, and gonitis.

MCH antagonists and formulations according to the invention may advantageously be used in combination with a dietary therapy, such as, for example, a dietary diabetes treatment, and exercise.

Another range of indications for which the compounds according to the invention are advantageously suitable is the prevention and/or treatment of micturition disorders, such as, for example, urinary incontinence, hyperactive bladder, urgency, nycturia, and enuresis, while the hyperactive bladder and urgency may or may not be connected with benign prostatic hyperplasia.

Generally speaking, the compounds according to the invention are potentially suitable for preventing and/or treating dependencies, such as, for example, alcohol and/or nicotine dependency, and/or withdrawal symptoms, such as, for example, weight gain in smokers coming off nicotine. By "dependency" is generally meant here an irresistible urge to take an addictive substance and/or to perform certain actions, particularly in order to either achieve a feeling of wellbeing or to eliminate negative emotions. In particular, the term "dependency" is used here to denote a dependency on an addictive substance. By "withdrawal symptoms" are meant here, in general, symptoms which occur or may occur when addictive substances are withdrawn from patients dependent on one or more such substances. The compounds according to the invention are potentially suitable particularly as active substances for reducing or ending tobacco consumption, for the treatment or prevention of a nicotine dependency and/or for the treatment or prevention of nicotine withdrawal symptoms, for reducing the craving for tobacco and/or nicotine and generally as an anti-smoking agent. The compounds according to the invention may also be useful for preventing or at least reducing the weight gain typically seen when smokers are coming off nicotine. The substances may also be suitable as active substances which prevent or at least reduce the craving for and/or relapse into a dependency on addictive substances. The term addictive substances refers particularly but not exclusively to substances with a psycho-motor activity, such as narcotics or drugs, particularly alcohol, nicotine, cocaine, amphetamine, opiates, benzodiazepines, and barbiturates.

The dosage required to achieve such an effect is conveniently, by intravenous or subcutaneous route, 0.001 to 30 mg/kg of body weight, preferably 0.01 to 5 mg/kg of body weight, and by oral or nasal route or by inhalation, 0.01 to 50 mg/kg of body weight, preferably 0.1 to 30 mg/kg of body weight, in each case 1 to 3× daily.

For this purpose, the compounds prepared according to the invention may be formulated, optionally in conjunction with other active substances as described hereinafter, together with one or more inert conventional carriers and/or diluents, e.g., with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose, or fatty substances such as hard fat or suitable mixtures thereof, to produce conventional galenic preparations such as plain or coated tablets, capsules, lozenges, powders, granules, solutions, emulsions, syrups, aerosols for inhalation, ointments, or suppositories.

In addition to pharmaceutical compositions, the invention also includes compositions containing at least one alkyne compound according to the invention and/or a salt according to the invention optionally together with one or more physiologically acceptable excipients. Such compositions may also be, for example, foodstuffs which may be solid or liquid, in which the compound according to the invention is incorporated.

For the abovementioned combinations it is possible to use as additional active substances particularly those which, for example, potentiate the therapeutic effect of an MCH antagonist according to the invention in terms of one of the indications mentioned above and/or which make it possible to reduce the dosage of an MCH antagonist according to the invention. Preferably one or more additional active substances are selected from among active substances for the treatment of diabetes, active substances for the treatment of diabetic complications, active substances for the treatment of obesity, preferably other than MCH antagonists, active substances for the treatment of high blood pressure, active substances for the treatment of hyperlipidemia, including arteriosclerosis, active substances for the treatment of dyslipidemia, including arteriosclerosis, active substances for the treatment of arthritis, active substances for the treatment of anxiety states, and active substances for the treatment of depression.

The abovementioned categories of active substances will now be explained in more detail by means of examples.

Examples of active substances for the treatment of diabetes are insulin sensitizers, insulin secretion accelerators, biguanides, insulins, α-glucosidase inhibitors, and $\beta_3$ adrenoreceptor agonists. Insulin sensitizers include glitazones, particularly pioglitazone and its salts (preferably hydrochloride), troglitazone, rosiglitazone and its salts (preferably maleate), JTT-501, GI-262570, MCC-555, YM-440, DRF-2593, BM-13-1258, KRP-297, R-119702, and GW-1929.

Insulin secretion accelerators include sulfonylureas, such as, for example, tolbutamide, chloropropamide, tolazamide, acetohexamide, glyclopyramide and its ammonium salts, glibenclamide, gliclazide, and glimepiride. Further examples of insulin secretion accelerators are repaglinide, nateglinide, mitiglinide (KAD-1229), and JTT-608. Biguanides include metformin, buformin, and phenformin. Insulins include those obtained from animals, particularly cattle or pigs, semisynthetic human insulins which are synthesized enzymatically from insulin obtained from animals, human insulin obtained by genetic engineering, e.g., from *Escherichia coli* or yeasts. Moreover, the term insulin also includes insulin-zinc (containing 0.45 to 0.9 percent by weight of zinc) and protamine-insulin-zinc obtainable from zinc chloride, protamine sulfate, and insulin. Insulin may also be obtained from insulin fragments or derivatives (for example INS-1, etc.). Insulin may also include different kinds, e.g., with regard to the onset time and duration of effect ("ultra immediate action type", "immediate action type", "two phase type", "intermediate type", "prolonged action type", etc.), which are selected depending on the pathological condition of the patient. α-Glucosidase inhibitors include acarbose, voglibose, miglitol, and emiglitate. $\beta_3$ Adrenoreceptor agonists include AJ-9677, BMS-196085, SB-226552, and AZ40140. Active substances for the treatment of diabetes other than those mentioned above include ergoset, pramlintide, leptin, and BAY-27-9955 as well as glycogen phosphorylase inhibitors, sorbitol dehydrogenase inhibitors, protein tyrosine phosphatase 1B inhibitors, dipeptidyl protease inhibitors, glipazide, and glyburide.

Active substances for the treatment of diabetic complications include, for example, aldose reductase inhibitors, glycation inhibitors and protein kinase C inhibitors, DPP-IV blockers, GLP-1 or GLP-2 analogues, and SGLT-2 inhibitors. Aldose reductase inhibitors are, for example, tolrestat, epalrestat, imirestat, zenarestat, SNK-860, zopolrestat, ARI -50i, and AS-3201. An example of a glycation inhibitor is pimagedine. Protein Kinase C inhibitors are, for example, NGF, and LY-333531. DPP-IV blockers are, for example, LAF237 (Novartis), MK431 (Merck), as well as 815541, 823093, and 825964 (all GlaxoSmithKline). GLP-1 analogues are, for example, Liraglutide (NN2211) (Novo Nordisk), CJC-1131 (Conjuchem), and Exenatide (Amylin). SGLT-2 inhibitors are, for example, AVE-2268 (Aventis) and T-1095 (Tanabe, Johnson & Johnson). Active substances other than those mentioned above for the treatment of diabetic complications include alprostadil, thiapride hydrochloride, cilostazol, mexiletine hydrochloride, ethyl eicosapentate, memantine, and pimagedine (ALT-711).

Active substances for the treatment of obesity, preferably other than MCH antagonists, include lipase inhibitors and anorectics. A preferred example of a lipase inhibitor is orlistat. Examples of preferred anorectics are phentermine, mazindol, fluoxetine, sibutramine, baiamine, (S)-sibutramine, SR-141716, and NGD-95-1. Active substances other than those mentioned above for the treatment of obesity include lipstatin.

Moreover, for the purposes of this application, the active substance group of anti-obesity active substances also includes the anorectics, of which the $\beta_3$ agonists, thyromimetic active substances and NPY antagonists should be emphasized. The range of substances which may be considered as preferred anti-obesity or anorectic active substances is indicated by the following additional list, by way of example: phenylpropanolamine, ephedrine, pseudoephedrine, phentermine, a cholecystokinin-A (hereinafter referred to as CCK-A) agonist, a monoamine reuptake inhibitor (such as, for example, sibutramine), a sympathomimetic active substance, a serotonergic active substance (such as, for example, dexfenfluramine, fenfluramine, a 5-HT2C agonist such as BVT.933 or APD356, or duloxetine), a dopamine antagonist (such as, for example, bromocriptine or pramipexole), a melanocyte-stimulating hormone receptor agonist or mimetic, an analogue of melanocyte-stimulating hormone, a cannabinoid receptor antagonist (ACOMPLIA® (rimonabant)), an MCH antagonist, the OB protein (hereinafter referred to as leptin), a leptin analogue, a fatty acid synthase (FAS) antagonist, a leptin receptor agonist, a galanine antagonist, and a GI lipase inhibitor or reducer (such as, for example, orlistat). Other anorectics include bombesin agonists, dehydroepiandrosterone or its analogues, glucocorticoid receptor agonists and antagonists, orexin receptor antagonists, urocortin binding protein antagonists, agonists of the Glucagon-like Peptide-1 receptor, such as, for example, exendin, AC 2993, CJC-1131, IP10, or GRT0203Y, DPP-IV inhibitors and ciliary neurotrophic factors, such as, for example, axokines. In this context mention should also be made of the forms of therapy which produce weight loss by increasing the fatty acid oxidation in the peripheral tissue, such as, for example, inhibitors of acetyl-coA carboxylase.

Active substances for the treatment of high blood pressure include inhibitors of angiotensin converting enzyme, calcium antagonists, potassium channel openers, and angiotensin II antagonists. Inhibitors of angiotensin converting enzyme include captopril, enalapril, alacepril, delapril (hydrochloride), lisinopril, imidapril, benazepril, cilazapril, temocapril, trandolapril, and manidipine (hydrochloride). Examples of calcium antagonists are nifedipine, amlodipine, efonidipine, and nicardipine. Potassium channel openers include levcromakalim, L-27152, AL0671, and NIP-121. Angiotensin II antagonists include telmisartan, losartan, candesartan cilexetil, valsartan, irbesartan, CS-866, and E4177.

Active substances for the treatment of hyperlipidemia, including arteriosclerosis, include HMG-CoA reductase inhibitors and fibrate compounds. HMG-CoA reductase inhibitors include pravastatin, simvastatin, lovastatin, atorvastatin, fluvastatin, lipantil, cerivastatin, itavastatin, ZD-4522 and their salts. Fibrate compounds include bezafibrate, clinofibrate, clofibrate, and simfibrate.

Active substances for the treatment of dyslipidemia, including arteriosclerosis, include, e.g., medicaments which raise the HDL level, such as, e.g., nicotinic acid and derivatives and preparations thereof, such as, e.g., niaspan, as well as agonists of the nicotinic acid receptor.

Active substances for the treatment of arthritis include NSAIDs (non-steroidal anti-inflammatory drugs), particularly COX-2 inhibitors, such as, for example, meloxicam or ibuprofen.

Active substances for the treatment of anxiety states include chlordiazepoxide, diazepam, oxozolam, medazepam, cloxazolam, bromazepam, lorazepam, alprazolam, and fludiazepam.

Active substances for the treatment of depression include fluoxetine, fluvoxamine, imipramine, paroxetine, and sertraline.

The dosage for these active substances is conveniently $\frac{1}{5}$ of the lowest normal recommended dose up to $\frac{1}{1}$ of the normal recommended dose.

In another embodiment the invention also relates to the use of at least one alkyne compound according to the invention and/or a salt according to the invention for influencing the eating behavior of a mammal. This use is particularly based on the fact that compounds according to the invention may be suitable for reducing hunger, curbing appetite, controlling eating behavior and/or inducing a feeling of satiety. The eating behavior is advantageously influenced so as to reduce food intake. Therefore, the compounds according to the invention are advantageously used for reducing body weight. Another use according to the invention is the prevention of increases in body weight, for example, in people who had previously taken steps to lose weight and are interested in maintaining their lower body weight. According to this embodiment it is preferably a non-therapeutic use. Such a non-therapeutic use might be a cosmetic use, for example, to alter the external appearance, or an application to improve general health. The compounds according to the invention are preferably used non-therapeutically for mammals, particularly humans, not suffering from any diagnosed eating disorders, no diagnosed obesity, bulimia, diabetes and/or no diagnosed micturition disorders, particularly urinary incontinence. Preferably, the compounds according to the invention are suitable for non-therapeutic use in people whose BMI (body mass index), defined as their body weight in kilograms divided by their height (in meters) squared, is below a level of 30, particularly below 25.

The Examples that follow are intended to illustrate the invention.

Preliminary Remarks

As a rule, IR, $^1$H-NMR and/or mass spectra have been obtained for the compounds prepared.

Unless otherwise stated the $R_f$ values were determined using ready-made silica gel 60 TLC plates $F_{254}$ (E. Merck, Darmstadt, Item No. 1.05714) without chamber saturation. The $R_f$ values obtained under the heading Alox were determined using ready-made aluminum oxide 60 TLC plates $F_{254}$ (E. Merck, Darmstadt, Item No. 1.05713) without chamber saturation. For chromatographic purifications silica gel made by Messrs Millipore (MATREX™, 35-70 my) or Alox (E. Merck, Darmstadt, standardized aluminum oxide 90, 63-200 µm, Item No. 1.01097.9050) is used. The ratios specified for the eluants are based on units by volume of the solvents in question. The units by volume specified in the case of $NH_3$ relate to a concentrated solution of $NH_3$ in water. Unless otherwise stated, the acid, base, and salt solutions used for working up the reaction solutions are aqueous systems of the concentrations specified. The HPLC data specified were measured under the parameters indicated below:

Analytical columns: Zorbax column (Agilent Technologies), SB (Stable Bond)—C18; 3.5 µm; 4.5×75 mm; column temperature: 30° C.; flow: 0.8 mL/min; injection volume: 5 µL; detection at 254 nm (methods A and B).

| time (min) | percent by volume of water (with 0.1% formic acid) | percent by volume of acetonitrile (with 0.1% formic acid) |
|---|---|---|
| Method A: | | |
| 0 | 95 | 5 |
| 9 | 10 | 90 |
| 10 | 10 | 90 |
| 11 | 90 | 10 |
| Method B: | | |
| 0 | 95 | 5 |
| 4 | 10 | 90 |
| 10 | 10 | 90 |
| 11 | 90 | 10 |

Analytical columns: Zorbax column (Agilent Technologies), Bonus RP—C14; 3.5 μm; 4.6×75 mm; column temperature: 30° C.; flow: 0.8 mL/min; injection volume: 5 μL; detection at 254 nm (method C)

| | Method C: | |
|---|---|---|
| time (min) | percent by volume of water (with 0.1% formic acid) | percent by volume of acetonitrile (with 0.1% formic acid) |
| 0 | 95 | 5 |
| 9 | 10 | 90 |
| 10 | 10 | 90 |
| 11 | 90 | 10 |

Preparative column: Zorbax column (Agilent Technologies), SB (Stable Bond)~C18; 3.5 μm; 30×100 mm; column temperature: ambient temperature; flow: 30 mL/min; detection at 254 nm.

In preparative HPLC purification, as a rule the same gradients are used which were used when obtaining the analytical HPLC data. The products are collected under mass control, the fractions containing the product are combined and freeze-dried.

Temperatures are given in degrees Celsius (° C.); times are generally given in minutes (min), hours (h) or days (d). If there is no specific information as to the configuration, it is not clear whether there are pure enantiomers or whether partial or even total racemization has taken place.

The following abbreviations are used above and hereinafter:

Cyc cyclohexane
DCM dichloromethane
DIPE diisopropylether
DMF dimethylformamide
dppf 1,1'-bis(diphenylphosphino)ferrocene
EtOAc ethyl acetate
EtOH ethanol
MeOH methanol
MTBE methyl-tert-butylether
NMP N-methylpyrrolidinone
PE petroleum ether
RT ambient (room) temperature (approximately 20° C.)
TBAF tetrabutylammonium fluoride hydrate
THF tetrahydrofuran
→* denotes the bonding site of a group

EXAMPLE 1

{6-[5-(4-chlorophenyl)pyridin-2-ylethynyl]-4-methylquinolin-2-yl}methylamine

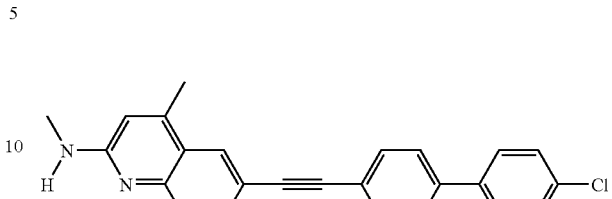

1a. N-(4-bromophenyl)-3-oxobutyramide

A solution of 25.72 mL (336 mmol) of diketene in 100 mL of toluene is added dropwise at 90° C. to a solution of 51.0 g (288 mmol) of 4-bromoaniline in 200 mL of toluene and the reaction mixture is kept for 5 hours at this temperature. The reaction solution is cooled in the ice bath, and the precipitate formed is filtered and then washed with toluene until the product is virtually colorless. Subsequently it is dried at 50° C. in the circulating air dryer until the weight is constant. Yield: 50.0 g (68% of theoretical); $C_{10}H_{10}BrNO_2$ (M=256.096); calc.: molpeak (M+H)$^+$: 256/258 (Br); found: molpeak (M+H)$^+$: 256/258 (Br); HPLC-MS: 4.7 min (method B).

1b. 6-bromo-4-methyl-1H-quinolin-2-one

A solution of 50.0 g (195 mmol) of N-(4-bromophenyl)-3-oxobutyramide in 217 mL of concentrated sulfuric acid is heated to 120° C. for 1 hour. After cooling to RT, the reaction solution is added to 1.5 L of ice water, stirred for 30 minutes, and the precipitate formed is filtered and washed again with 4 L of water. Subsequently it is dried at 35° C. in the circulating air dryer until the weight is constant. Yield: 24.0 g (52% of theoretical); $C_{10}H_8BrNO$ (M=238.081); calc.: molpeak (M+H)$^+$: 238/240 (Br); found: molpeak (M+H)$^+$: 238/240 (Br); HPLC-MS: 4.8 min (method B).

1c. 6-iodo-4-methyl-1H-quinolin-2-one

A mixture of 5.0 g (21.0 mmol) of 6-bromo-4-methyl-1H-quinolin-2-one and 400 mg (2.1 mmol) of CuI in 21 mL 1,4-dioxane is evacuated and gassed with argon. Then 6.3 g (42.0 mmol) of NaI and 0.45 mL (4.2 mmol) of N,N'-dimethylethylenediamine are added, the mixture is evacuated again and gassed with argon before being heated overnight to 110° C. HPLC analysis of the mixture shows approximately 20% reaction. Therefore another 400 mg (2.1 mmol) of CuI, 6.3 g (42.0 mmol) of NaI, 0.45 mL (4.2 mmol) of N,N'-dimethylethylenediamine, and 21 mL of 1,4-dioxane are added and this mixture is heated overnight again to 110° C. To complete the reaction, the above procedure is repeated another three times. After cooling, the suspension is combined with 10% NH$_3$ solution and water and the precipitated product is filtered off. This is then washed with 10% NH$_3$ solution, water, isopropanol, DIPE, EtOAc, and DCM and dried overnight in the air. The product, which still contains approximately 20% educt, is further reacted without purification. Yield: 3.0 g (40% of theoretical); $C_{10}H_8INO$ (M=285.081); calc.: molpeak (M+H)$^+$: 286; found: molpeak (M+H)$^+$: 286; HPLC-MS: 5.0 min (method B).

1d. 5-bromo-2-[(tert-butyldimethylsilanyl)ethynyl]pyridine

Under an argon atmosphere, 0.80 g (4.20 mmol) of CuI and 2.90 g (4.13 mmol) of bis(triphenylphosphane)palladium (II) chloride are added to a solution of 49.90 g (201.0 mmol) of 2,5-dibromopyridine and 43.0 mL (225.6 mmol) of tert-butylethynyldimethylsilane in 500 mL of dry THF and 120 mL of triethylamine at −7° C. and the mixture is stirred for 30 minutes at 0° C. The reaction mixture is stirred for a further 3.5 hours at RT, then filtered, and the filtrate is evaporated down in vacuo. The residue is dissolved in 1 L of EtOAc, and the organic phase is washed with water and saturated NaCl solution, dried over sodium sulfate ($Na_2SO_4$), and evaporated down in vacuo. The crude product is further reacted without purification. Yield: 59.5 g (quant. yield); $C_{13}H_{18}BrNSi$ (M=296.278); calc.: molpeak (M+H)$^+$: 296/298 (Br); found: molpeak (M+H)$^+$: 296/298 (Br); $R_f$ value: 0.75 (silica gel, Cyc/EtOAc 8:1).

1e. 2-[(tert-butyldimethylsilanyl)ethynyl]-5-(4-chlorophenyl)pyridine 250 mL of MeOH, 220 mL of 2N sodium carbonate ($Na_2CO_3$) solution, and 1.80 g (2.46 mmol) of $PdCl_2(dppf)$ are added to a solution of 59.5 g (201.0 mmol) of 5-bromo-2-[(tert-butyldimethylsilanyl)ethynyl]pyridine and 36.5 g (233.4 mmol) of 4-chlorophenylboric acid in 600 mL of 1,4-dioxane and the mixture is refluxed for 1 hour. The reaction mixture is evaporated down in vacuo and diluted with EtOAc. The organic phase is washed with water and semisaturated sodium bicarbonate ($NaHCO_3$) solution, dried over sodium sulfate, and evaporated down in vacuo. The residue is purified by column chromatography (silica gel, Cyc/EtOAc 9:1). Yield: 38.5 g (58% of theoretical); $C_{19}H_{22}ClNSi$ (M=327.923); calc.: molpeak (M+H)$^+$: 328/330 (Cl); found: molpeak (M+H)$^+$: 328/330 (Cl); $R_f$ value: 0.60 (silica gel, Cyc/EtOAc 8:1).

1f. 5-(4-chlorophenyl)-2-ethynylpyridine 43.66 g (156.0 mmol) of TBAF are added at $R_T$ to a solution of 46.50 g (142.0 mmol) of 2-[(tert-butyldimethylsilanyl)ethynyl]-5-(4-chlorophenyl)pyridine in 1 L of DCM and the mixture is stirred for 2 hours. The organic phase is washed with water, dried over sodium sulfate, and evaporated down in vacuo. The residue is stirred with DIPE, and the precipitate is filtered off and washed with PE. Yield: 26.0 g (86% of theoretical); $C_{13}H_8ClN$ (M=213.662); calc.: molpeak (M+H)$^+$: 214/216 (Cl); found: molpeak (M+H)$^+$: 214/216 (Cl); $R_f$ value: 0.30 (silica gel, Cyc/EtOAc 4:1).

1g. 6-[5-(4-chlorophenyl)pyridin-2-ylethynyl]-4-methyl-1H-quinolin-2-one 1.8 g (8.42 mmol) of 5-(4-chlorophenyl)-2-ethynylpyridine and 2.34 mL (16.84 mmol) of triethylamine are added to a suspension of 3.0 g (8.42 mmol) of 6-iodo-4-methyl-1H-quinolin-2-one in 20 mL of DMF and the mixture is evacuated three times and gassed with argon. Then 40.1 mg (0.21 mmol) of CuI and 153.9 mg (0.21 mmol) of $PdCl_2(dppf)$-DCM complex are added and the mixture is evacuated again and gassed with argon. The reaction mixture is stirred overnight at RT, combined with EtOAc, and the precipitated product is filtered off and with washed EtOAc. The residue is stirred with a THF/water mixture (1:1), filtered, washed with THF, and dried in the circulating air dryer at 50° C. until the weight is constant. Yield: 3.10 g (99% of theoretical); $C_{23}H_{15}ClN_2O$ (M=370.831); calc.: molpeak (M+H)$^+$: 371/373 (Cl); found: molpeak (M+H)$^+$: 371/373 (Cl).

1h. 2-chloro-6-[5-(4-chlorophenyl)pyridin-2-ylethynyl]-4-methylquinoline 3.0 g (8.09 mmol) of 6-[5-(4-chlorophenyl)pyridin-2-ylethynyl]-4-methyl-1H-quinolin-2-one is added batchwise to 37.1 mL of phosphorus oxychloride and refluxed for 2 hours. After cooling, the reaction mixture is slowly poured onto 500 mL of 10% $NH_3$ solution and stirred for 30 minutes in the ice bath. The mixture is extracted exhaustively with EtOAc, and the combined organic phases are washed with water and dried over magnesium sulfate ($MgSO_4$). After the desiccant and solvent have been eliminated, the residue is reacted further without purification. Yield: 1.40 g (44% of theoretical); $C_{23}H_{14}Cl_2N_2$ (M=389.276); calc.: molpeak (M+H)$^+$: 389/391/393 (2Cl); found: molpeak (M+H)$^+$: 389/391/393 (2Cl).

1i. 2-bromo-6-[5-(4-chlorophenyl)pyridin-2-ylethynyl]-4-methylquinoline 478 mg (1.48 mmol) of tetrabutylammonium bromide and 493 mg (3.37 mmol) of phosphorus pentoxide are added to a suspension of 500 mg (1.21 mmol) of 6-[5-(4-chlorophenyl)pyridin-2-ylethynyl]-4-methyl-1H-quinolin-2-one in 10 mL of toluene and the reaction mixture is heated to 95° C. for 1.5 hours. After cooling, the organic phase is decanted off, the residue is treated twice with toluene in the ultrasound bath, and the combined organic phases are washed with semisaturated sodium bicarbonate solution and water and dried over magnesium sulfate. After the desiccant and solvent have been eliminated, the residue is dried and reacted further without purification. Yield: 120 mg (18% of theoretical); $C_{23}H_{14}BrClN_2$ (M=433.730); calc.: molpeak (M+H)$^+$: 433/435/437 (BrCl); found: molpeak (M+H)$^+$: 433/435/437 (BrCl).

1k. {6-[5-(4-chlorophenyl)pyridin-2-ylethynyl]-4-methylquinolin-2-yl} methylamine 19.1 mg (0.617 mmol) of methylamine is added to a solution of 60 mg (0.154 mmol) of 2-chloro-6-[5-(4-chlorophenyl)pyridin-2-ylethynyl]-4-methylquinoline in 5 mL of 1,4-dioxane and the reaction mixture is heated to 130° C. for 70 hours in the sealed vessel. The mixture is evaporated down in vacuo, and the residue is triturated with a little isopropanol, filtered, and washed with isopropanol, EtOAc, and DIPE. The residue is dissolved in DCM, filtered to remove insoluble ingredients, evaporated down, and dried. Yield: 28 mg (47% of theoretical); $C_{24}H_{18}ClN_3$ (M=383.873); calc.: molpeak (M+H)$^+$: 384/386 (Cl); found: molpeak (M+H)$^+$: 384/386 (Cl); HPLC-MS: 5.7 min (method A).

The following Examples are prepared analogously, starting from 60 mg of 2-chloro-6-[5-(4-chlorophenyl)pyridin-2-ylethynyl]-4-methylquinoline (Example 1h) and the corresponding amines.

| | | | | HPLC retention time |
|---|---|---|---|---|
| Example | R | Yield (%) | Empirical formula | Mass spectrum | in min (method) |

(Structure at top: 4-methylquinoline with R at 2-position, 6-ethynyl connected to pyridine-5-(4-chlorophenyl))

| Example | R | Yield (%) | Empirical formula | Mass spectrum | HPLC retention time (method) |
|---|---|---|---|---|---|
| 1.1 | ethylaminomethyl (N-ethyl NH) | 60 | $C_{25}H_{20}ClN_3$ | 398/400 [M + H]$^+$ | 5.9 (A) |
| 1.2 | azetidinyl | 24 | $C_{26}H_{20}ClN_3$ | 409/411 [M + H]$^+$ | 4.9 (B) |
| 1.3 | 4-methylpiperazinyl | 52 | $C_{28}H_{25}ClN_4$ | 453/455 [M + H]$^+$ | 5.2 (A) |
| 1.4 | cyclobutylamino | 5 | $C_{27}H_{22}ClN_3$ | 424/426 [M + H]$^+$ | 6.3 (A) |
| 1.5 | cyclopentylamino | 10 | $C_{28}H_{24}ClN_3$ | 438/440 [M + H]$^+$ | 6.5 (A) |
| 1.6 | (R or S)-1-cyclohexylethylamino | 12 | $C_{31}H_{30}ClN_3$ | 480/482 [M + H]$^+$ | 7.2 (A) |
| 1.7 | (R or S)-1-cyclohexylethylamino | 4 | $C_{31}H_{30}ClN_3$ | 480/482 [M + H]$^+$ | 7.2 (A) |

Analogously to Example 1k, the following Examples may be prepared starting from 2-chloro-6-[5-(4-chlorophenyl)pyridin-2-ylethynyl]-4-methylquinoline (Example 1h) or 2-bromo-6-[5-(4-chlorophenyl)pyridin-2-ylethynyl]-4-methylquinoline (Example 1i) and the corresponding amines: Examples 1.8-1.9, 1.11, 1.15-1.21, 1.23 and 1.28 were prepared by heating in NMP in the microwave (300 W, 190° C.; 30-60 min); Example 1.13 was prepared by heating in DMF in the microwave (150 W, 170° C.; 10 min); and Example 1.51 was obtained as a by-product.

| Example | Structure | Yield (%) | Mass spectrum | HPLC retention time (method) |
|---|---|---|---|---|
| 1.8 | 2-(2-hydroxyethylamino)-4-methyl-6-[5-(4-chlorophenyl)pyridin-2-ylethynyl]quinoline | 4 | 414/416 [M + H]$^+$ | |

-continued

| Example | Structure | Yield (%) | Mass spectrum | HPLC retention time (method) |
|---|---|---|---|---|
| 1.9 | 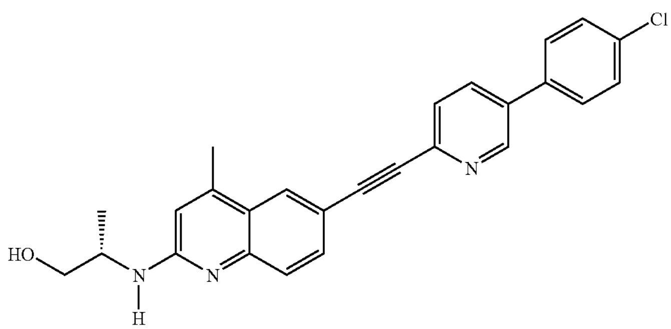 | 34 | 428/430 [M + H]⁺ | 5.4 min (C) |
| 1.10 | 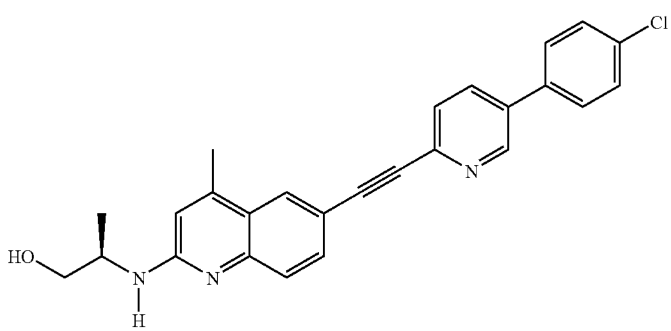 | | | |
| 1.11 | 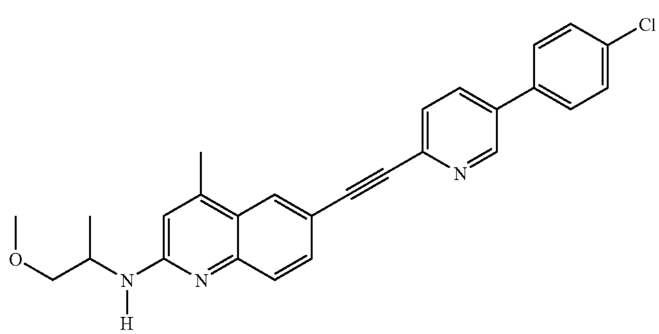 | 29 | 442/444 [M + H]⁺ | 5.9 min (C) |
| 1.12 | 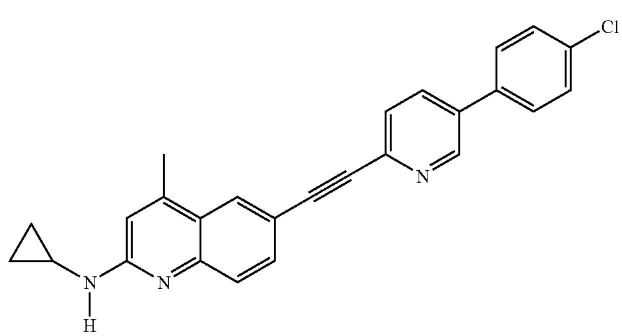 | 18 | 410/412 [M + H]⁺ | 4.79 min (B) |

-continued

| Example | Structure | Yield (%) | Mass spectrum | HPLC retention time (method) |
|---|---|---|---|---|
| 1.13 | 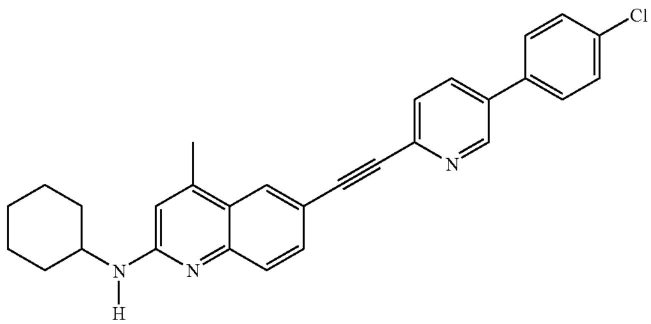 | 17 | 452/454 [M + H]+ | 6.64 min (C) |
| 1.14 | 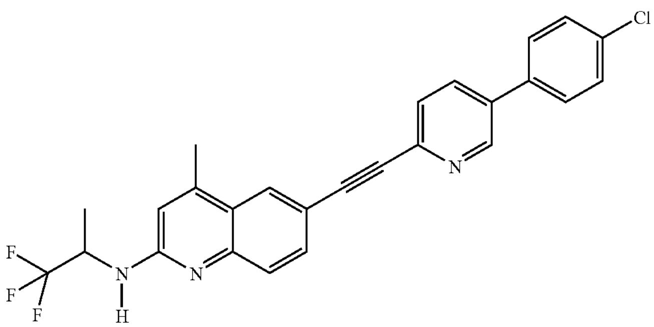 | | | |
| 1.15 | 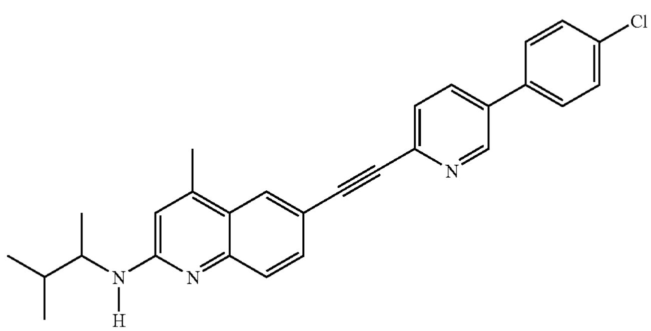 | 20 | 440/442 [M + H]+ | 6.5 min (C) |
| 1.16 | 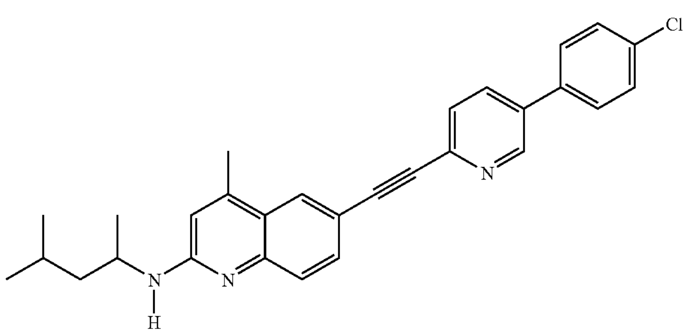 | 27 | 454/456 [M + H]+ | 6.8 min (C) |

-continued

| Example | Structure | Yield (%) | Mass spectrum | HPLC retention time (method) |
|---|---|---|---|---|
| 1.17 | 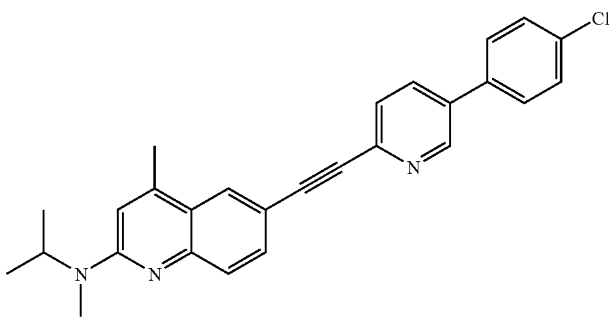 | 17 | 426/428 [M + H]⁺ | 6.0 min (C) |
| 1.18 | 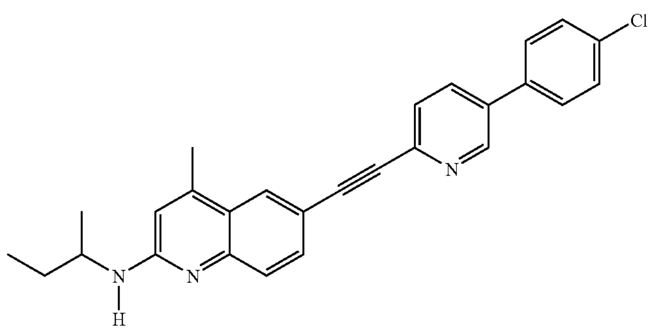 | 9 | 426/428 [M + H]⁺ | 6.2 min (C) |
| 1.19 | 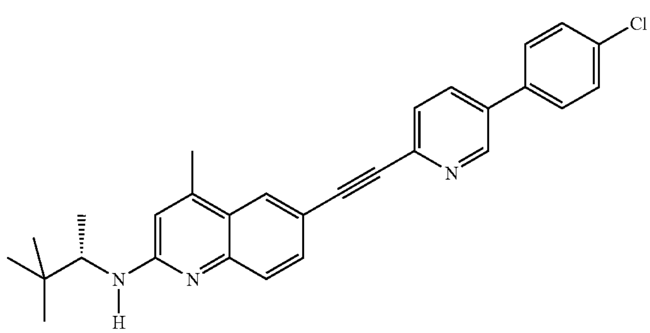 | 12 | 454/456 [M + H]⁺ | 6.7 min (C) |
| 1.20 | 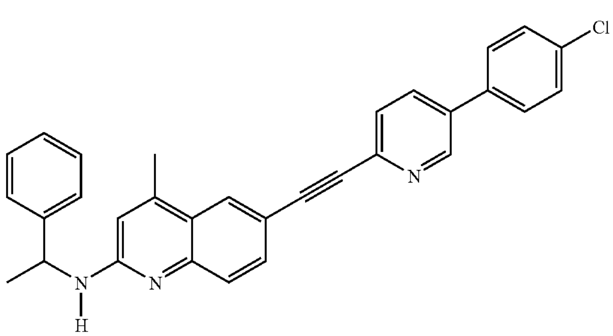 | 35 | 474/476 [M + H]⁺ | 6.9 min (C) |

-continued

| Example | Structure | Yield (%) | Mass spectrum | HPLC retention time (method) |
|---|---|---|---|---|
| 1.21 | 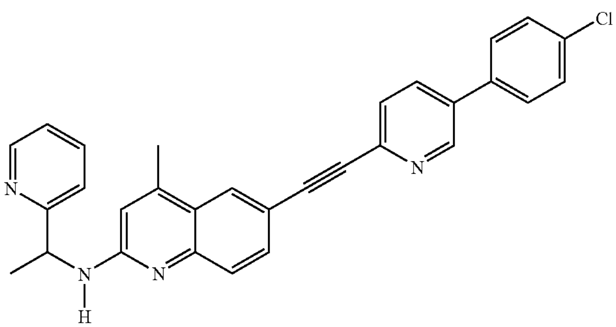 | 16 | 475/477 [M + H]+ | 6.3 min (C) |
| 1.22 | 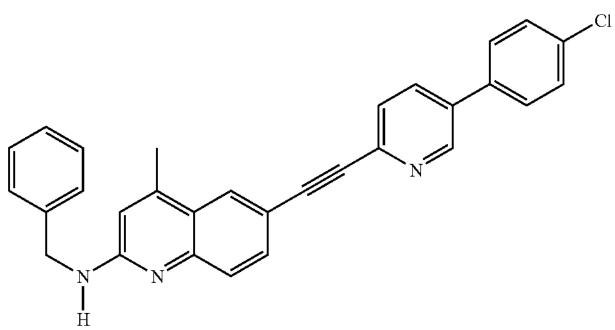 | | | |
| 1.23 | 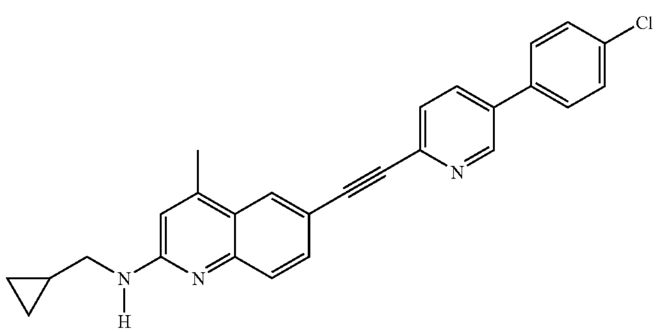 | 9 | 424/426 [M + H]+ | 6.11 min (C) |
| 1.24 | 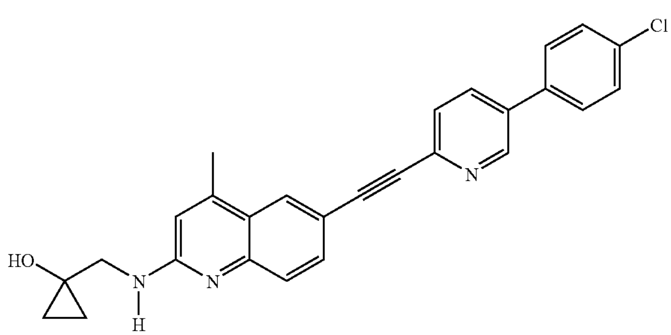 | | | |

| Example | Structure | Yield (%) | Mass spectrum | HPLC retention time (method) |
|---|---|---|---|---|
| 1.25 | 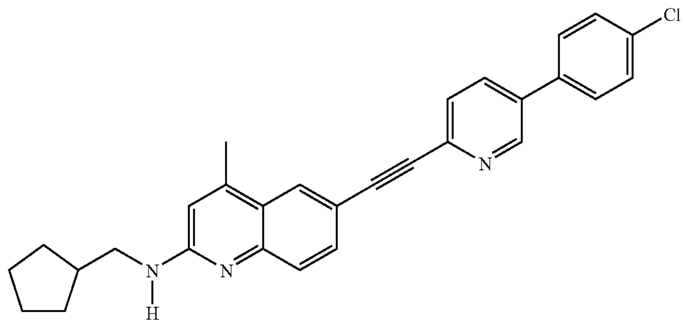 | | | |
| 1.26 | 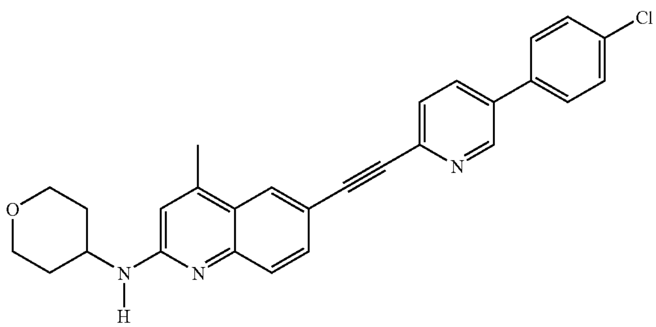 | | | |
| 1.27 | 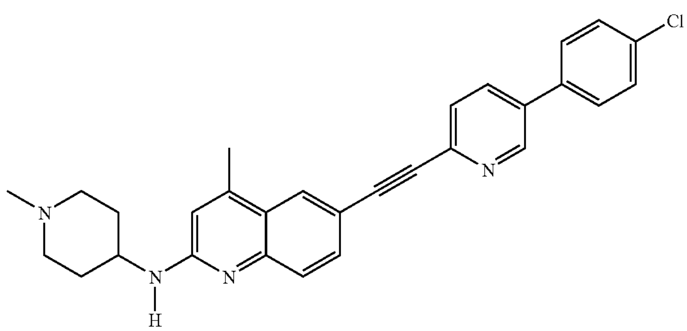 | | | |
| 1.28 | 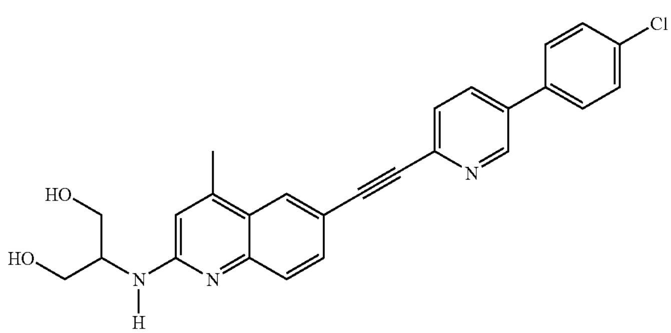 | 3 | 444/446 [M + H]+ | 5.4 min (C) |

-continued

| Example | Structure | Yield (%) | Mass spectrum | HPLC retention time (method) |
|---|---|---|---|---|
| 1.29 | 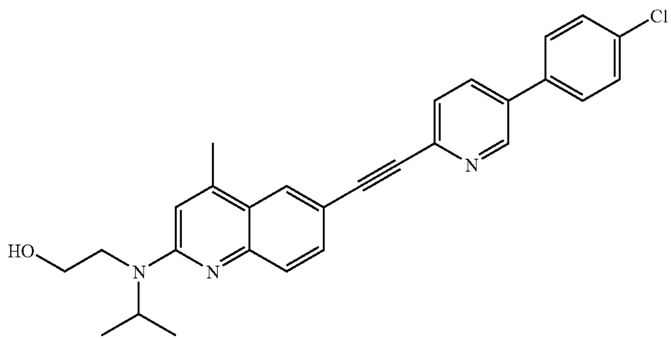 | | | |
| 1.30 | 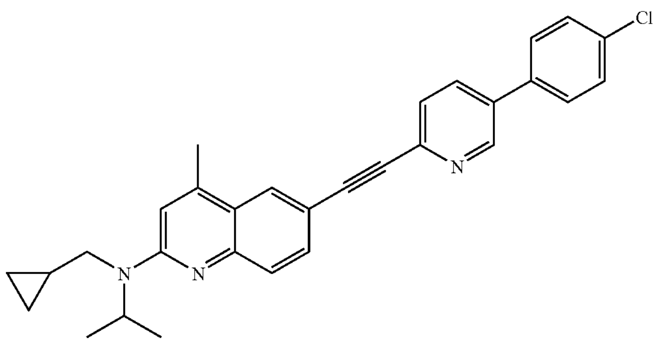 | | | |
| 1.31 | 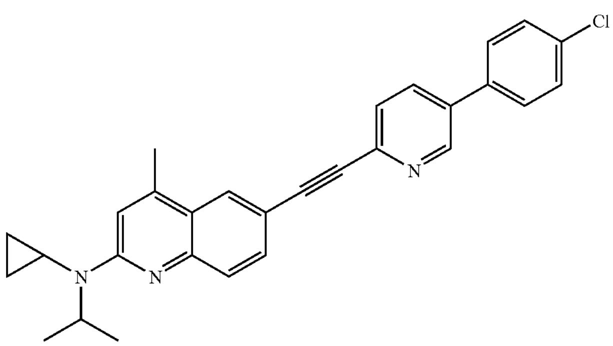 | | | |
| 1.32 | 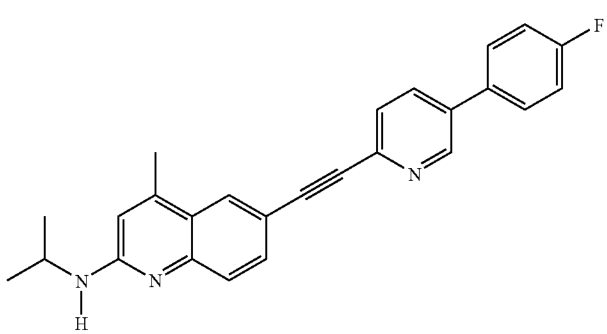 | | | |

-continued
| Example | Structure | Yield (%) | Mass spectrum | HPLC retention time (method) |
|---|---|---|---|---|
| 1.33 | 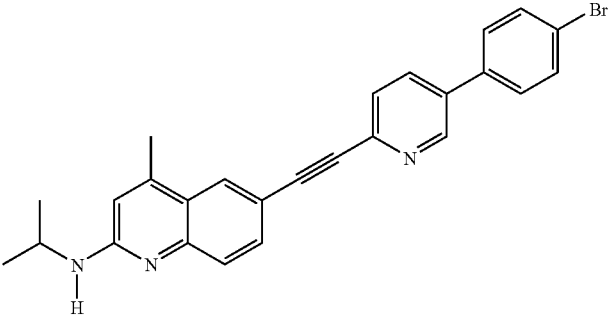 | | | |
| 1.34 | 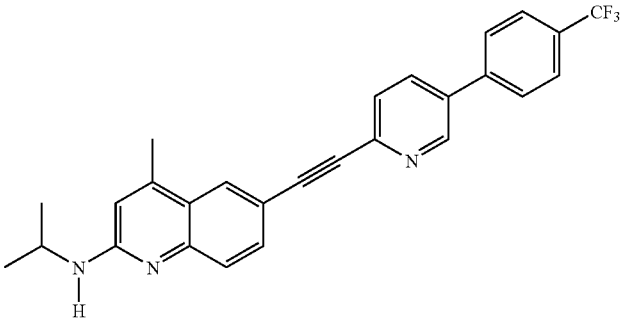 | | | |
| 1.35 | 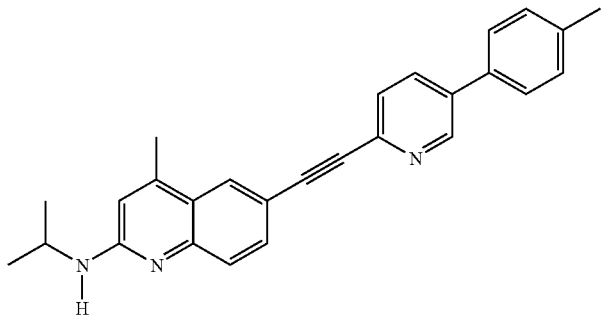 | | | |
| 1.36 | 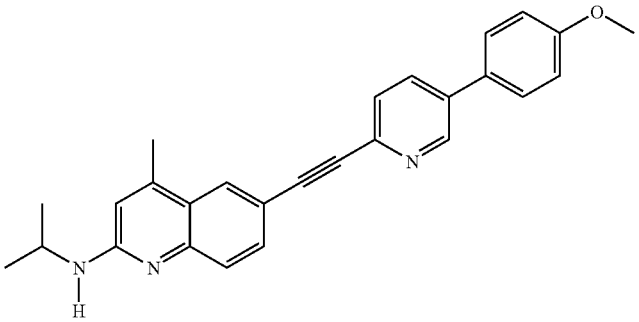 | | | |

-continued

| Example | Structure | Yield (%) | Mass spectrum | HPLC retention time (method) |
|---|---|---|---|---|
| 1.37 | 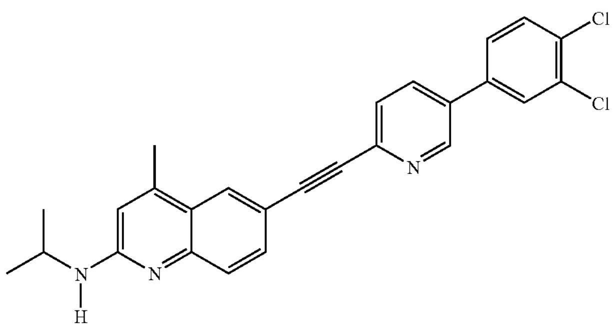 | | | |
| 1.38 | 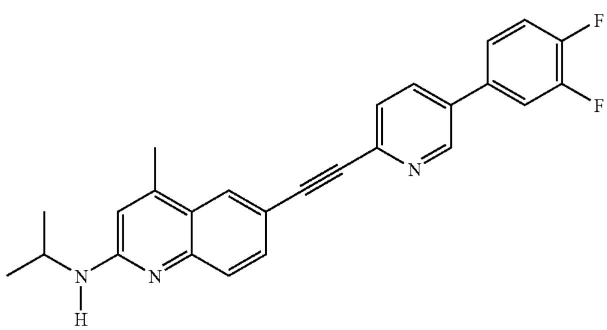 | | | |
| 1.39 | 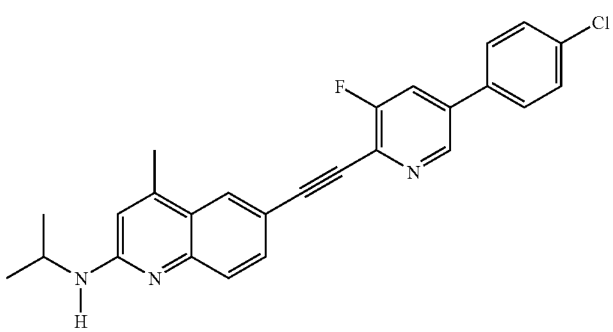 | | | |
| 1.40 | 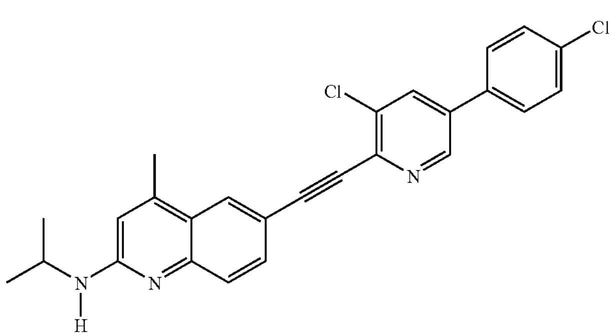 | | | |

EXAMPLE 1.41

6-[5-(4-chlorophenyl)pyridin-2-ylethynyl]-4-methyl-2-pyrrolidin-1-ylquinoline

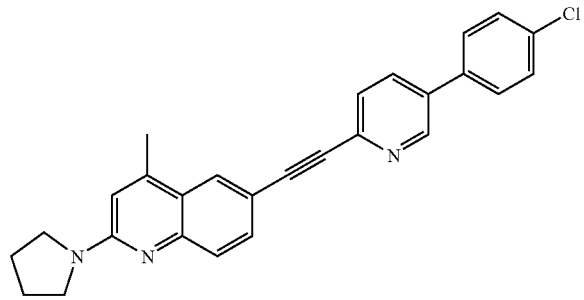

77 μL (0.925 mmol) of pyrrolidine is added to a solution of 90 mg (0.231 mmol) of 2-chloro-6-[5-(4-chlorophenyl)pyridin-2-ylethynyl]-4-methylquinoline in 5 mL of 1,4-dioxane and the reaction mixture is refluxed overnight. It is evaporated down in vacuo, and the residue is taken up in DMF and purified by HPLC-MS. The fractions containing the product are combined, evaporated down, and freeze-dried. The product is dissolved in DCM, evaporated down, and the residue is triturated with a little EtOAc, filtered, washed again with a little EtOAc, and dried at 50° C. in the circulating air dryer. Yield: 39 mg (39% of theoretical); $C_{27}H_{22}ClN_3$ (M=423.936); calc.: molpeak $(M+H)^+$: 424/426 (Cl); found: molpeak $(M+H)^+$: 424/426 (Cl); HPLC-MS: 5.8 min (method A).

EXAMPLE 1.42

6-[5-(4-chlorophenyl)pyridin-2-ylethynyl]-4-methyl-2-pyrrolidin-1-ylquinoline

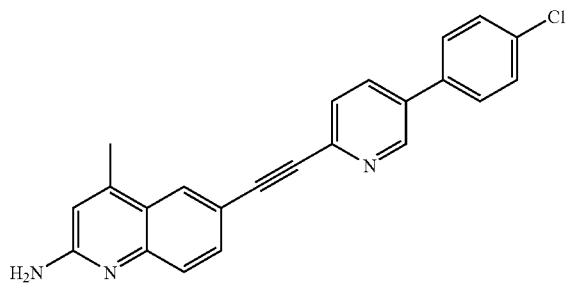

A mixture of 200 mg (0.514 mmol) of 2-chloro-6-[5-(4-chlorophenyl)pyridin-2-ylethynyl]-4-methylquinoline, 607 mg (10.28 mmol) of acetamide, and 355 mg (2.57 mmol) of potassium carbonate ($K_2CO_3$) are heated to 200° C. for 7 hours in a melt. After cooling, water is added, the mixture is exhaustively extracted with EtOAc, the combined organic phases are extracted twice with semisaturated sodium bicarbonate solution and dried over magnesium sulfate. After the desiccant and solvent have been eliminated, the residue is dissolved in DMF, filtered, and purified by HPLC-MS. Yield: 4 mg (2% of theoretical); $C_{23}H_{16}ClN_3$ (M=369.846); calc.: molpeak $(M+H)^+$: 370/372 (Cl); found: molpeak $(M+H)^+$: 370/372 (Cl); HPLC-MS: 5.5 min (method A).

EXAMPLE 1.43

6-[5-(4-chlorophenyl)pyridin-2-ylethynyl]-4-methyl-2-(4-methylpiperidin-1-yl)quinoline

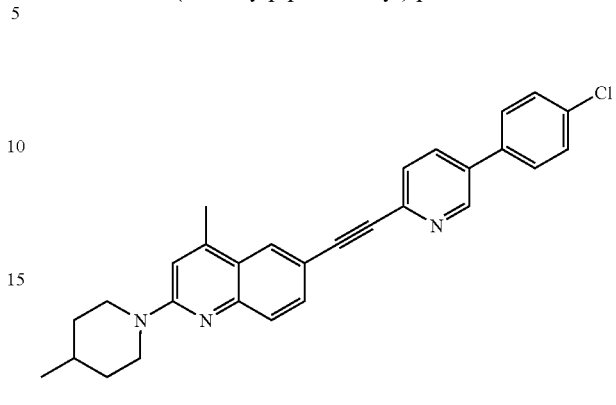

1.43a. 6-bromo-2-chloro-4-methylquinoline 25 mL of phosphorus oxychloride is added to 2.7 g (11.34 mmol) of 6-bromo-4-methyl-1H-quinolin-2-one (Example 1b) and the reaction mixture is refluxed for 2 hours. After cooling, the mixture is added batchwise to 250 mL of 10% $NH_3$ solution, the precipitate formed is filtered off, washed with water, and dried in the circulating air dryer at 30° C. Yield: 2.7 g (93% of theoretical); $C_{10}H_7BrClN$ (M=256.526); calc.: molpeak $(M+H)^+$: 256/258/260 (BrCl); found: molpeak $(M+H)^+$: 256/258/260 (BrCl); $R_f$ value: 0.95 (silica gel, DCM/MeOH 9:1).

1.43b. 6-bromo-4-methyl-2-(4-methylpiperidin-1-yl)quinoline 0.24 mL (2.0 mmol) of 4-methylpiperidine and 0.28 mL (2.0 mmol) of triethylamine are added to a solution of 0.51 g (2.0 mmol) of 6-bromo-2-chloro-4-methylquinoline in 15 mL of 1,4-dioxane and the reaction mixture is refluxed overnight. After cooling, the precipitate is filtered off, the filtrate is evaporated down, the residue is combined with acetonitrile and MTBE, filtered to remove insoluble ingredients, and the filtrate is evaporated down again. Yield: 0.69 g (100% of theoretical); $C_{16}H_{19}BrN_2$ (M=319.240); calc.: molpeak $(M+H)^+$: 319/321 (Br); found: molpeak $(M+H)^+$: 319/321 (Br); HPLC-MS: 4.7 min (method B).

1.43c. 6-iodo-4-methyl-2-(4-methylpiperidin-1-yl)quinoline

Under an argon atmosphere, 39 mg (0.2 mmol) of CuI, 0.6 g (4.0 mmol) of NaI, and 43 μL N,N'-dimethylethylenediamine are added to a solution of 0.69 g (2.0 mmol) of 6-bromo-4-methyl-2-(4-methylpiperidin-1-yl)quinoline in 2 mL of 1,4-dioxane and the reaction mixture is shaken for 14 hours at 110° C. After cooling, it is combined with 60 mL of EtOAc, and the organic phase is washed twice with 20 mL of 5% $NH_3$ solution and dried over magnesium sulfate. After the desiccant and solvent have been eliminated, the residue is reacted further without purification. Yield: 0.65 g (88% of theoretical); $C_{16}H_{19}IN_2$ (M=366.240); calc.: molpeak $(M+H)^+$: 367; found: molpeak $(M+H)^+$: 367; HPLC-MS: 7.0 min (method A).

1.43d. 6-[5-(4-chlorophenyl)pyridin-2-ylethynyl]-4-methyl-2-(4-methylpiperidin-1-yl)quinoline A solution of 293 mg (0.8 mmol) of 6-iodo-4-methyl-2-(4-methylpiperidin-1-yl)quinoline, 184 mg (0.8 mmol, 93% purity) 5-(4-chlorophenyl)-2-ethynylpyridine, and 158 μL (1.6 mmol) of piperidine in 4 mL of 1,4-dioxane is evacuated three times and gassed with argon. After the addition of 3 mg (0.016 mmol) of CuI and 13 mg (0.016 mmol) of PdCl$_2$ (dppf)-DCM complex, the reaction mixture is stirred for 4 hours at RT. It is combined with 10 mL of EtOAc, and the precipitate is filtered off, washed with a little EtOAc and MeOH, and dried in the air. Yield: 240 mg (66% of theoretical); C$_{29}$H$_{26}$ClN$_3$ (M=451.990); calc.: molpeak (M+H)$^+$: 452/454 (Cl); found: molpeak (M+H)$^+$: 452/454 (Cl); HPLC-MS: 6.1 min (method B).

EXAMPLE 1.44

{6-[5-(4-chlorophenyl)pyridin-2-ylethynyl]-4-methylquinolin-2-yl}isopropylamine

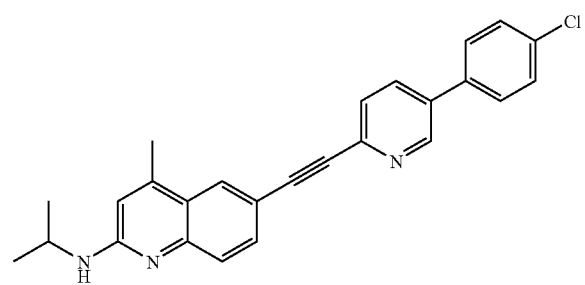

Prepared analogously in a sequence analogous to Example 1.43b (with 0.3 g of 6-bromo-2-chloro-4-methylquinoline; 61% yield), 1.43c (with 0.2 g of (6-bromo-4-methylquinolin-2-yl)-isopropylamine; 60% yield) and 1.43d (with 0.16 g of (6-iodo-4-methylquinolin-2-yl)-isopropylamine; 8% yield). C$_{26}$H$_{22}$ClN$_3$ (M=411.926); calc.: molpeak (M+H)$^+$: 412/414 (Cl); found: molpeak (M+H)$^+$: 412/414 (Cl); HPLC-MS: 5.6 min (method B).

The following Examples are prepared analogously to Example 1k starting from 90 mg of 2-chloro-6-[5-(4-chlorophenyl)pyridin-2-ylethynyl]-4-methylquinoline (Example 1h) and the corresponding amines.

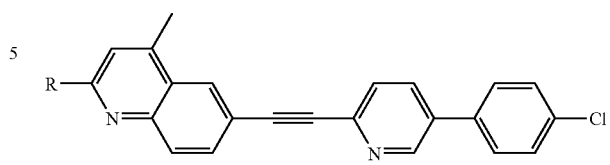

| Example | R | Yield (%) | Empirical formula | Mass spectrum | HPLC retention time in min (method) |
|---|---|---|---|---|---|
| 1.45 |  | 11 | C$_{26}$H$_{22}$ClN$_3$O | 428/430 [M + H]$^+$ | 5.5 (C) |
| 1.46 | 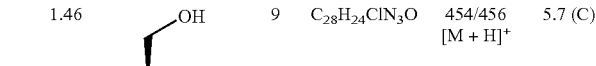 | 9 | C$_{28}$H$_{24}$ClN$_3$O | 454/456 [M + H]$^+$ | 5.7 (C) |
| 1.47 | 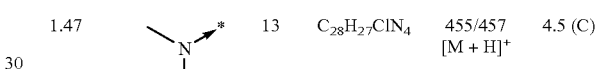 | 13 | C$_{28}$H$_{27}$ClN$_4$ | 455/457 [M + H]$^+$ | 4.5 (C) |
| 1.48 | 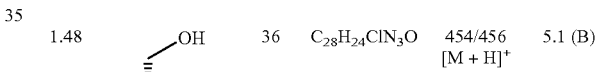 | 36 | C$_{28}$H$_{24}$ClN$_3$O | 454/456 [M + H]$^+$ | 5.1 (B) |

The following products are prepared from 100 mg of 2-chloro-6-[5-(4-chlorophenyl)pyridin-2-ylethynyl]-4-methylquinoline (Example 1h) and the corresponding amines by heating in NMP in the microwave (60 min 300 W, 190° C.).

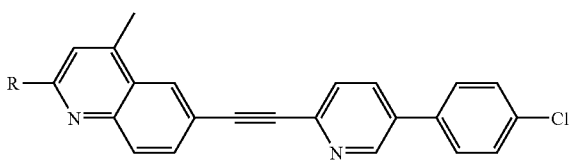

| Example | R | Yield (%) | Empirical formula | Mass spectrum | HPLC retention time in min (method) |
|---|---|---|---|---|---|
| 1.49 | 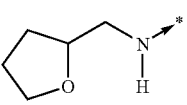 | 17 | C$_{28}$H$_{24}$ClN$_3$O | 454/456 [M + H]$^+$ | 5.9 (C) |

-continued

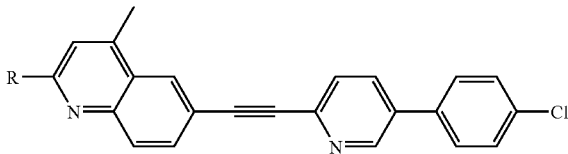

| Example | R | Yield (%) | Empirical formula | Mass spectrum | HPLC retention time in min (method) |
|---|---|---|---|---|---|
| 1.50 | H\N\*\n  \n —O | 9 | C₂₆H₂₂ClN₃O | 428/430 [M + H]⁺ | 7.8 (C) |

EXAMPLE 1.51

{6-[5-(4-chlorophenyl)pyridin-2-ylethynyl]-4-methylquinolin-2-yl}dimethylamine

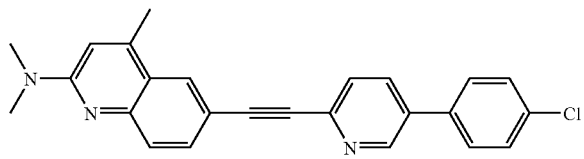

By-product of the preparation of Example 1.13. Yield: 61 mg (50% of theoretical based on 2-chloro-6-[5-(4-chlorophenyl)pyridin-2-ylethynyl]-4-methylquinoline). $C_{25}H_{20}ClN_3$ (M=397.899); calc.: molpeak (M+H)⁺: 398/400 (Cl). found: molpeak (M+H)⁺: 398/400 (Cl); HPLC-MS: 5.6 min (method C).

EXAMPLE 2.1

5-[5-(4-chlorophenyl)pyridin-2-ylethynyl]-2-pyrrolidin-1-yl-1H-benzimidazole ditrifluoroacetate

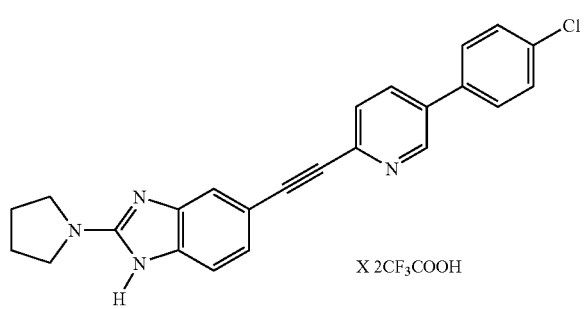

X 2CF₃COOH

2.1a. 5-bromo-1,3-dihydrobenzimidazol-2-one 4.29 g (26.46 mmol) of carbonyldiimidazole (CDI) is added to a solution of 4.5 g (24.05 mmol) of 4-bromobenzene-1,2-diamine in 95 mL of DMF and the reaction mixture is stirred for 5 hours at 80° C. Then the reaction mixture is poured onto water and the precipitate formed is filtered off. The precipitate is washed three times with water and dried in the circulating air dryer at 60° C. Yield: 4.6 g (90% of theoretical); $C_7H_5BrN_2O$ (M=213.03); calc.: molpeak (M+H)⁺: 213/215; found: molpeak(M+H)⁺: 213/215; $R_f$ value: 0.5 (silica gel, DCM/MeOH 10:1).

2.1b. 2,5-dibromo-1H-benzimidazole 4.5 g (21.12 mmol) of 5-bromo-1,3-dihydrobenzimidazol-2-one is added batchwise at 60° C. to a melt of 30.27 g (105.6 mmol) of phosphorus oxybromide and the reaction mixture is stirred for 5 hours at 110° C. Then the reaction mixture is poured onto water and the precipitate formed is filtered off. The precipitate is stirred with DIPE/acetone (4:1) and the solid is filtered off. The solid is dried in the circulating air dryer at 50° C. Yield: 3.4 g (58% of theoretical); $C_7H_4Br_2N_2$ (M=275.92); calc.: molpeak (M+H)⁺: 275/277/279; found: molpeak (M+H)⁺: 275/277/279; $R_f$ value: 0.6 (silica gel, DCM/MeOH 10:1).

2.1c. 5-bromo-2-pyrrolidin-1-yl-1H-benzimidazole

A suspension of 1 g (3.6 mmol) of 2,5-dibromo-1H-benzimidazole and 0.85 mL (10.18 mmol) of pyrrolidine in 45 mL of acetonitrile is heated for 2 hours at 150° C. in the microwave. The reaction mixture is poured onto water and extracted with EtOAc. The organic phase is washed three times with water and dried over sodium sulfate. The solvent is distilled off, and the residue is stirred with DIPE and the solid is filtered off. Yield: 0.43 g (45% of theoretical); $C_{11}H_{12}BrN_3$ (M=266.13); calc.: molpeak (M−H)—: 264/266; found: molpeak (M−H)⁻: 264/266; $R_f$ value: 0.5 (silica gel, DCM/MeOH 10:1).

2.1d. 5-iodo-2-pyrrolidin-1-yl-1H-benzimidazole 0.48 g (1.8 mmol) of 5-bromo-2-pyrrolidin-1-yl-1H-benzimidazole and 34 mg (0.18 mmol) of CuI are placed in a round flask. The reaction vessel is flushed with argon. Then 0.54 g (3.6 mmol) of NaI, 32 mg (0.36 mmol) of dimethylenediamine, and 3 mL of 1,4-dioxane are added under argon. The reaction mixture is stirred for 14 hours at 110° C. Subsequently, the cooled reaction mixture is combined with concentrated ammonia solution, diluted with water, and the precipitate formed is filtered off. The solid is stirred with methanol and again filtered. Yield: 0.3 g (53% of theoretical); $C_{11}H_{12}IN_3$ (M=313.13); calc.: molpeak (M+H)$^+$: 314; found: molpeak (M)$^+$: 314.

2.1e. 5-[5-(4-chlorophenyl)pyridin-2-ylethynyl]-2-pyrrolidin-1-yl-1H-benzimidazole ditrifluoroacetate 0.2 g (0.64 mmol) of 5-iodo-2-pyrrolidin-1-yl-1H-benzimidazole, 0.62 g (1.92 mmol) of cesium carbonate, 0.036 g (0,03 mmol) of tetrakistriphenylphosphine palladium, and 0.012 g (0.06 mmol) of CuI are suspended in 20 mL of absolute THF and the reaction mixture is degassed and ventilated with argon. Then 0.273 g (1.28 mmol) of 5-(4-chlorophenyl)-2-ethynylpyridine is added at RT under argon and the reaction mixture is stirred for 16 hours. The reaction mixture is poured into a 2N NH$_3$ solution and the precipitate formed is filtered off. The solid is washed with water. Then the solid is dissolved in DMF/trifluoroacetic acid and purified by HPLC (solvent: acetonitrile/water/0.5% trifluoroacetic acid). Yield: 40 mg (10% of theoretical); $C_{24}H_{19}ClN_4 \times 2$ $C_2HF_3O_2$ (M=626.93); melting point: 179° C.-180° C.; calc.: molpeak (M+H)$^+$: 399/401; found: molpeak (M+H)$^+$: 399/401.

The following compounds may be prepared analogously to Example 2.1.

| Example | Structure | Yield in % | Mass spectrum | retention time HPLC (method) |
|---|---|---|---|---|
| 2.2 | 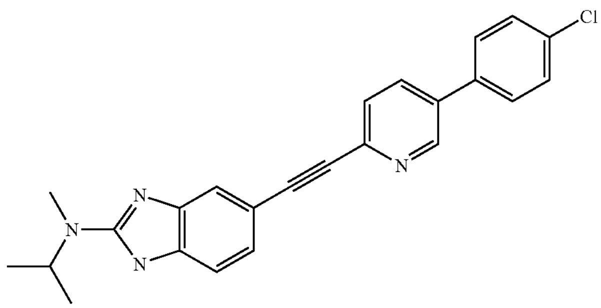 | 9 | 401/403 [M + H]$^+$ | 3.1 (C) |
| 2.3 | 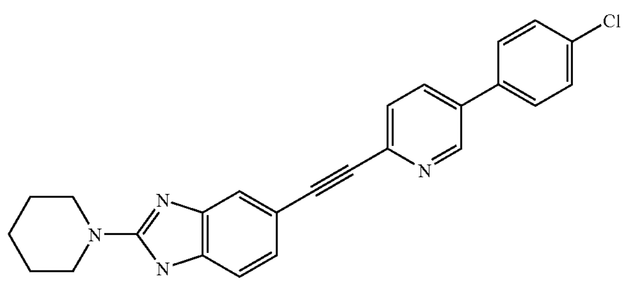 | | | |
| 2.4 | 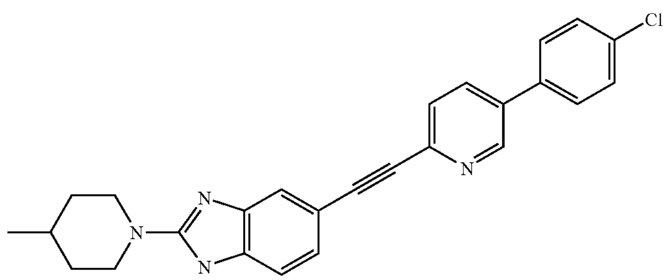 | | | |
| 2.5 | 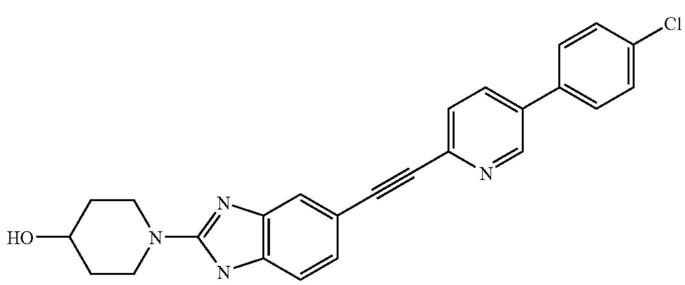 | | | |

| Example | Structure | Yield in % | Mass spectrum | retention time HPLC (method) |
|---|---|---|---|---|
| 2.6 | 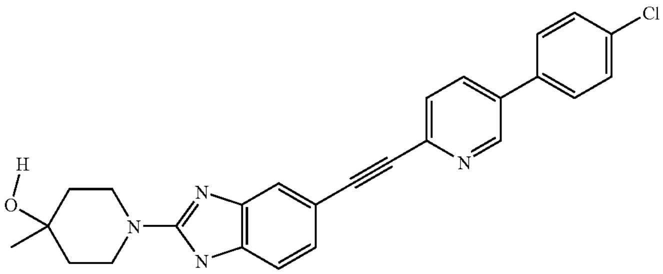 | | | |
| 2.7 | 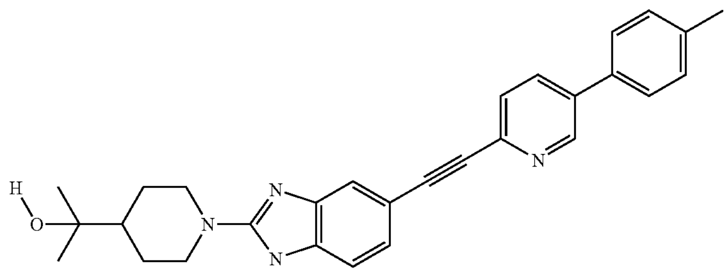 | | | |
| 2.8 | 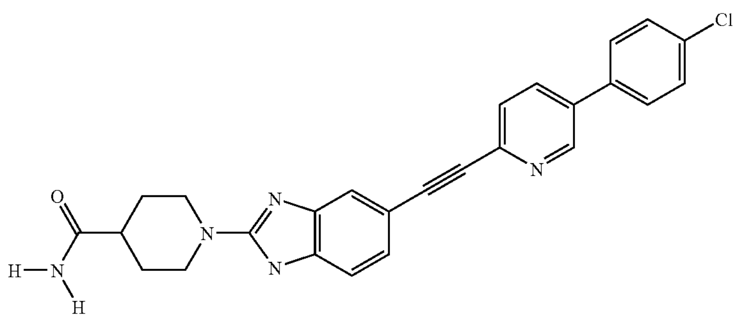 | | | |
| 2.9 | 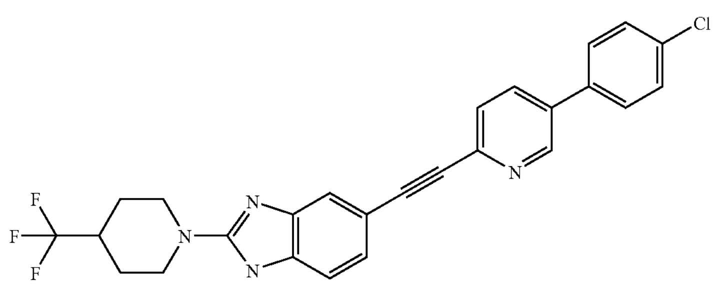 | | | |
| 2.10 | 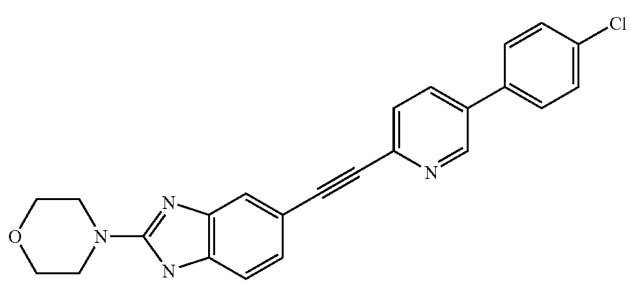 | | | |

-continued
| Example | Structure | Yield in % | Mass spectrum | retention time HPLC (method) |
|---|---|---|---|---|
| 2.11 | 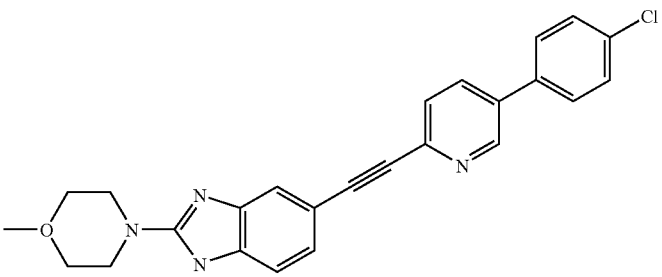 | | | |
| 2.12 | 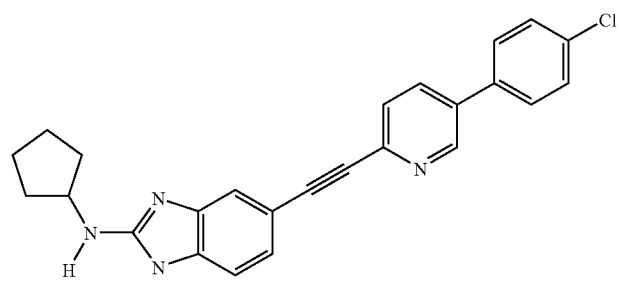 | | | |
| 2.13 | 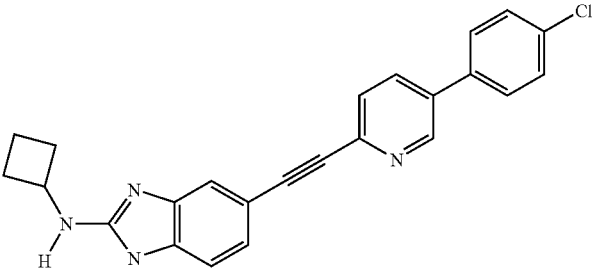 | | | |
| 2.14 | 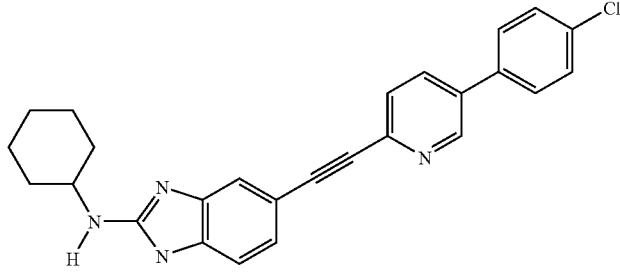 | | | |
| 2.15 | 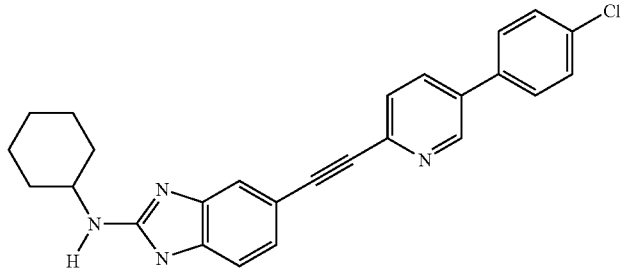 | | | |

| Example | Structure | Yield in % | Mass spectrum | retention time HPLC (method) |
|---|---|---|---|---|
| 2.16 | 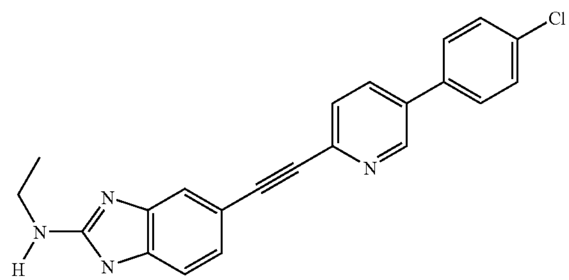 | | | |
| 2.17 | 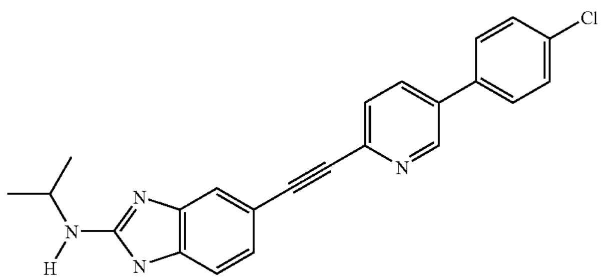 | | | |
| 2.18 | 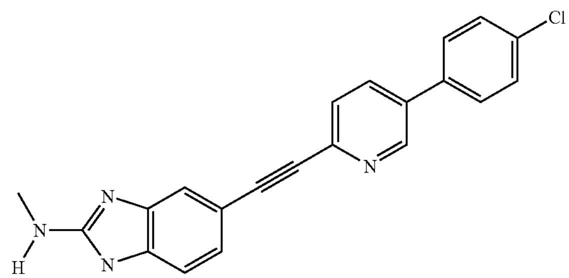 | | | |
| 2.19 | 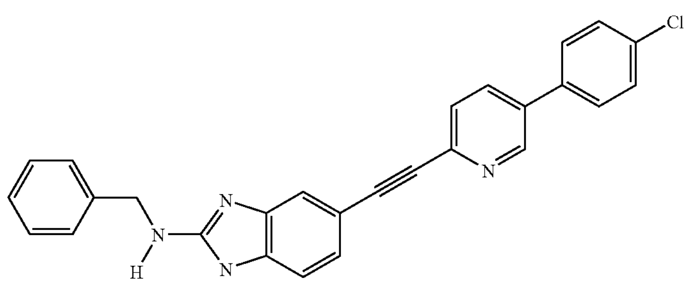 | | | |
| 2.20 | 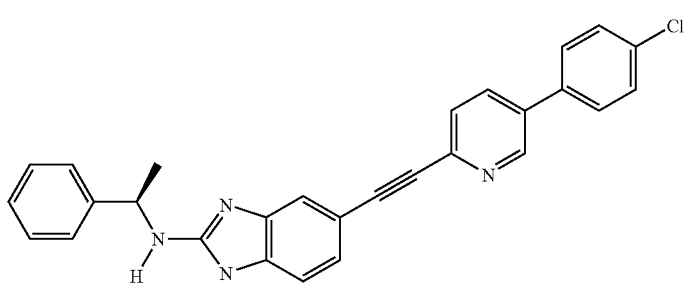 | | | |

-continued
| Example | Structure | Yield in % | Mass spectrum | retention time HPLC (method) |
|---|---|---|---|---|
| 2.21 | 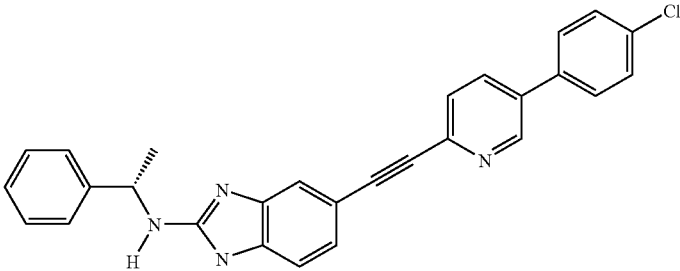 | | | |
| 2.22 | 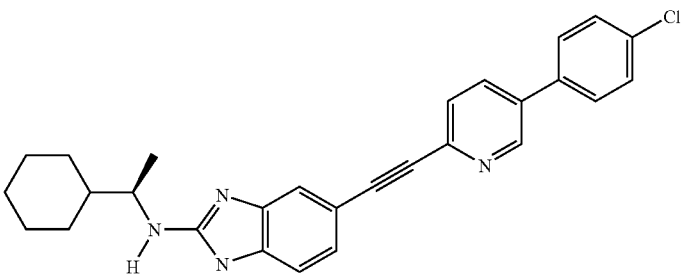 | | | |
| 2.23 | 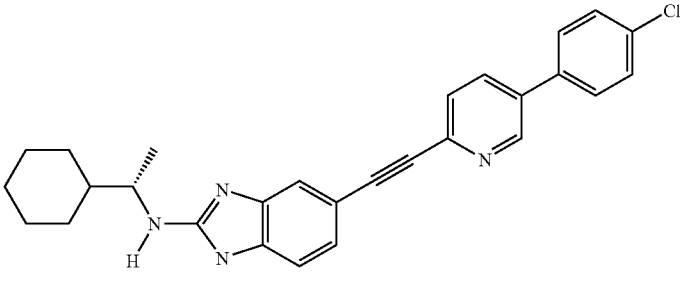 | | | |
| 2.24 | 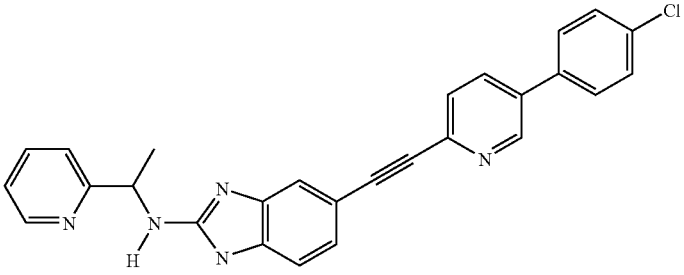 | | | |
| 2.25 | 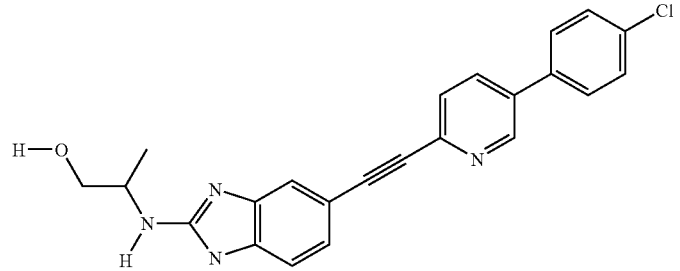 | | | |

-continued

| Example | Structure | Yield in % | Mass spectrum | retention time HPLC (method) |
|---|---|---|---|---|
| 2.26 | 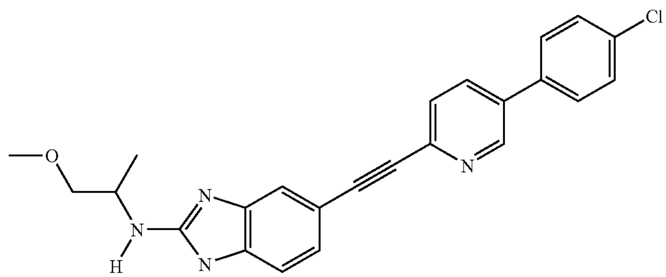 | | | |
| 2.27 | 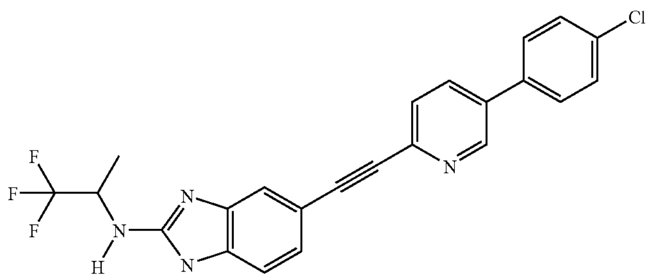 | | | |
| 2.28 | 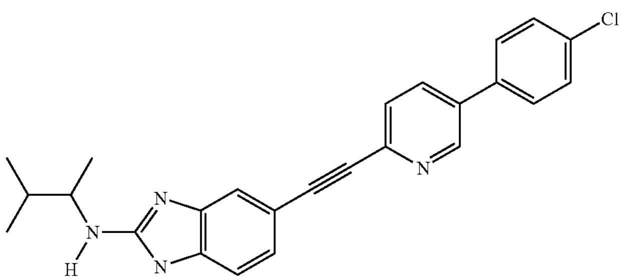 | | | |
| 2.29 | 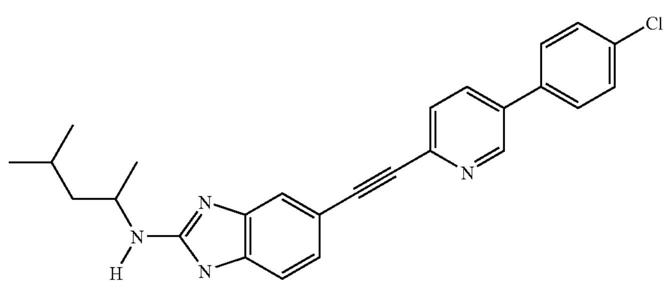 | | | |
| 2.30 | 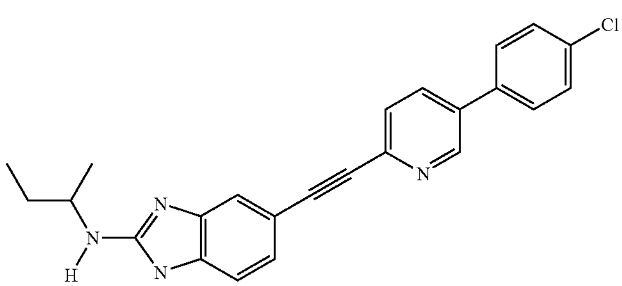 | | | |

-continued

| Example | Structure | Yield in % | Mass spectrum | retention time HPLC (method) |
|---------|-----------|------------|---------------|------------------------------|
| 2.31 | 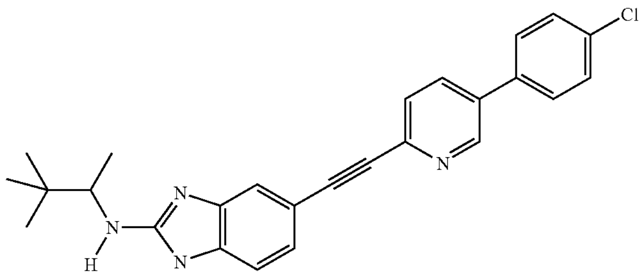 | | | |
| 2.32 | 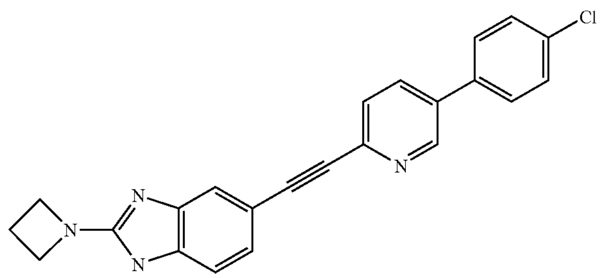 | | | |
| 2.33 | 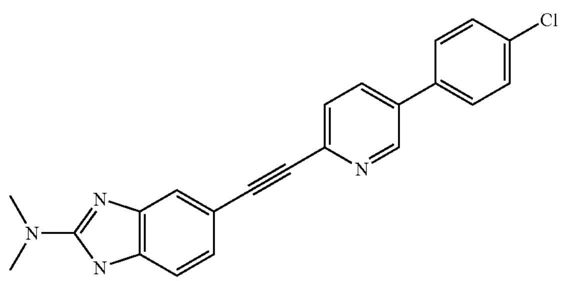 | | | |
| 2.34 | 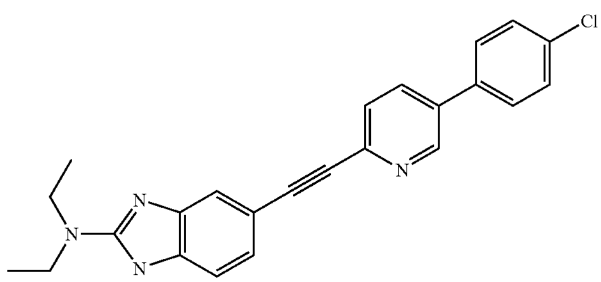 | | | |
| 2.35 | 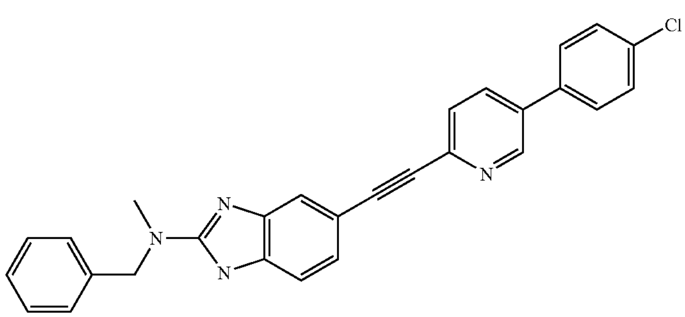 | | | |

-continued

| Example | Structure | Yield in % | Mass spectrum | retention time HPLC (method) |
|---|---|---|---|---|
| 2.36 | 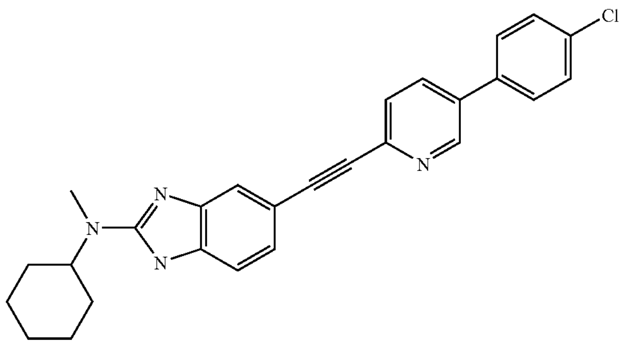 | | | |
| 2.37 | 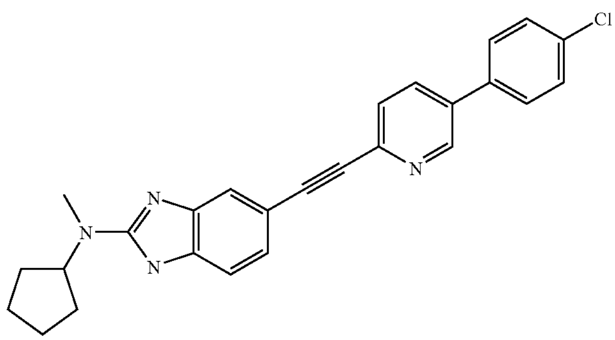 | | | |
| 2.38 | 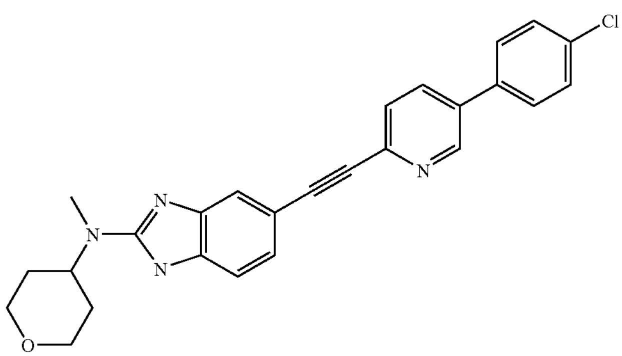 | | | |
| 2.39 | 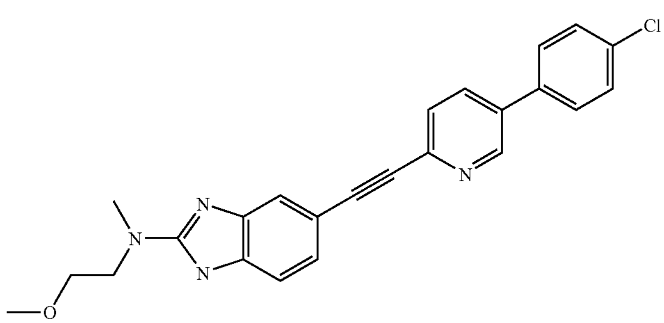 | | | |

-continued
| Example | Structure | Yield in % | Mass spectrum | retention time HPLC (method) |
|---|---|---|---|---|
| 2.40 | 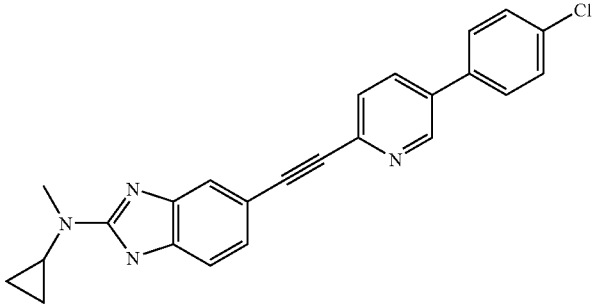 | | | |
| 2.41 | 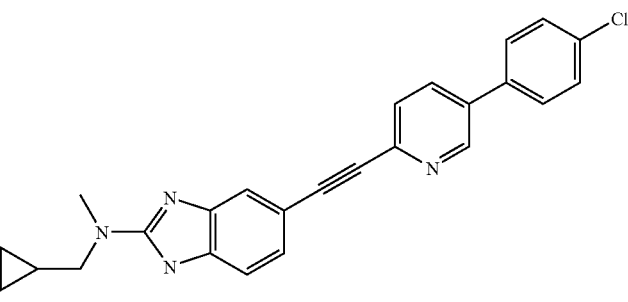 | | | |
| 2.42 | 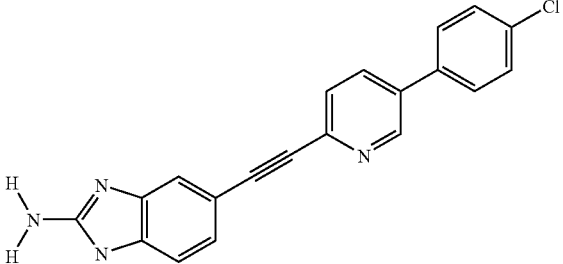 | | | |
| 2.43 | 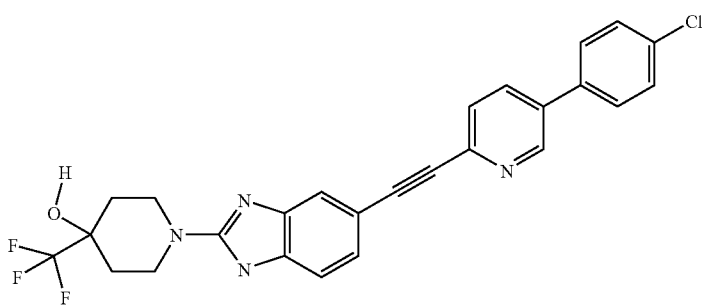 | | | |
| 2.44 | 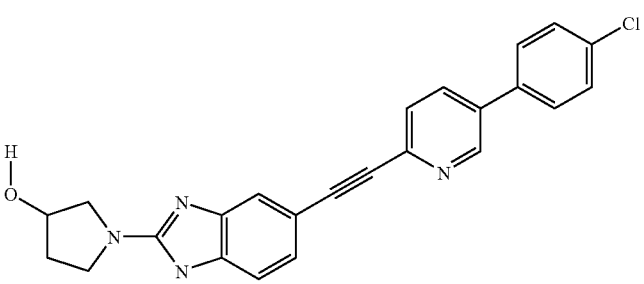 | | | |

-continued
| Example | Structure | Yield in % | Mass spectrum | retention time HPLC (method) |
|---------|-----------|------------|---------------|------------------------------|
| 2.45 | 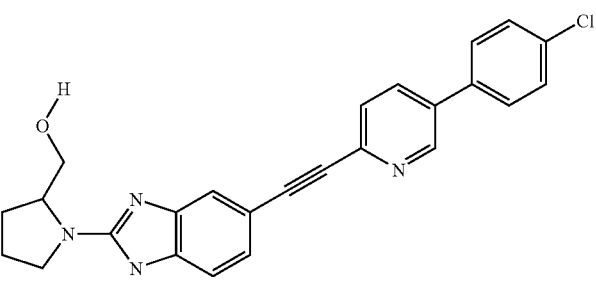 | | | |
| 2.46 | 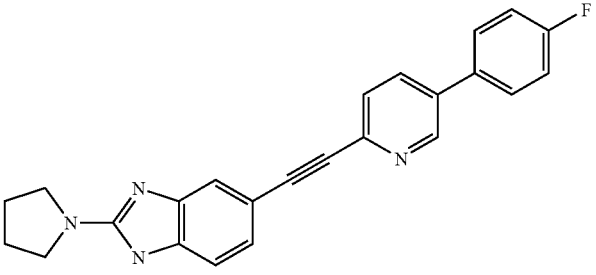 | | | |
| 2.47 | 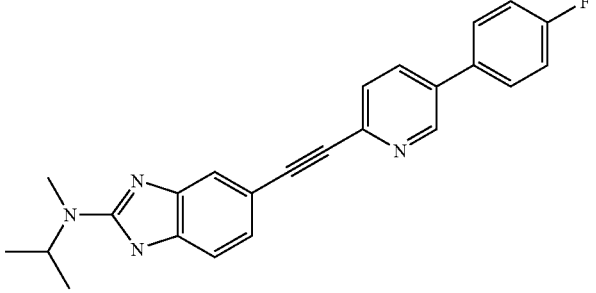 | | | |
| 2.48 | 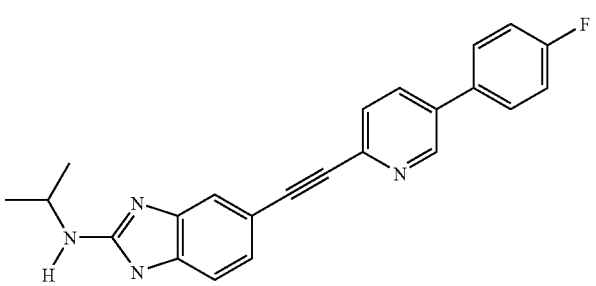 | | | |
| 2.49 | 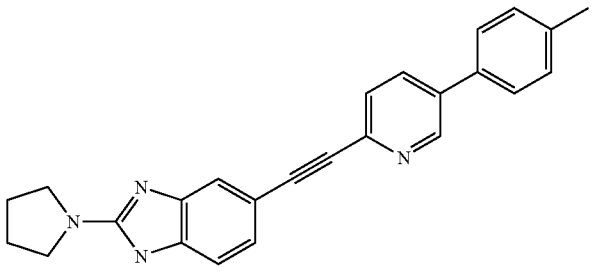 | | | |

-continued

| Example | Structure | Yield in % | Mass spectrum | retention time HPLC (method) |
|---|---|---|---|---|
| 2.50 | 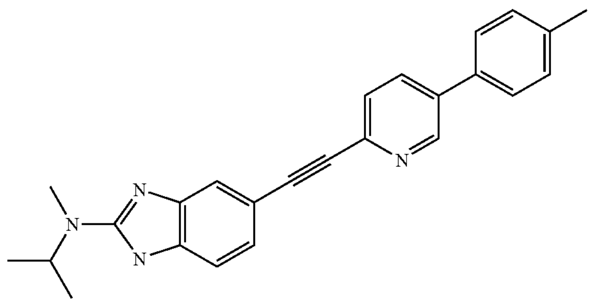 | | | |
| 2.51 | 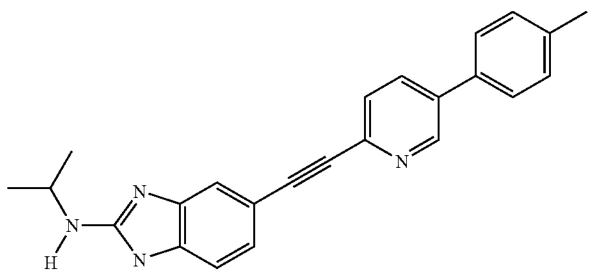 | | | |
| 2.52 | 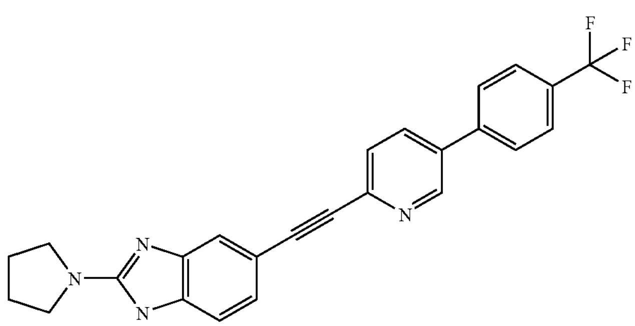 | | | |
| 2.53 | 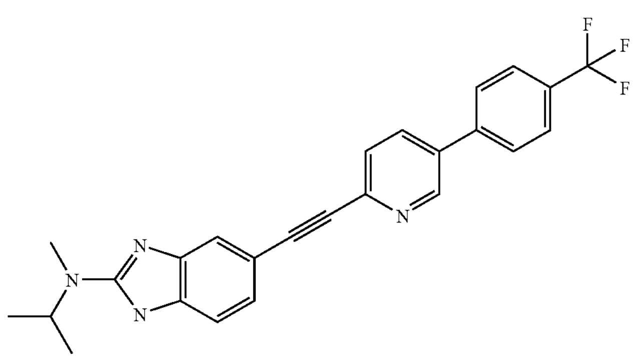 | | | |

-continued

| Example | Structure | Yield in % | Mass spectrum | retention time HPLC (method) |
|---|---|---|---|---|
| 2.54 | 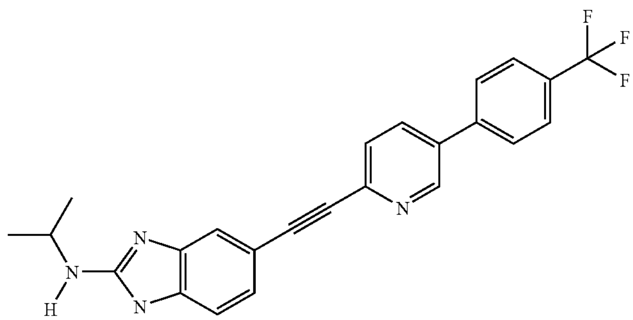 | | | |
| 2.55 | 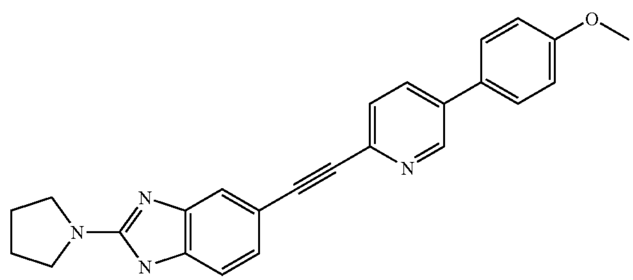 | | | |
| 2.56 | 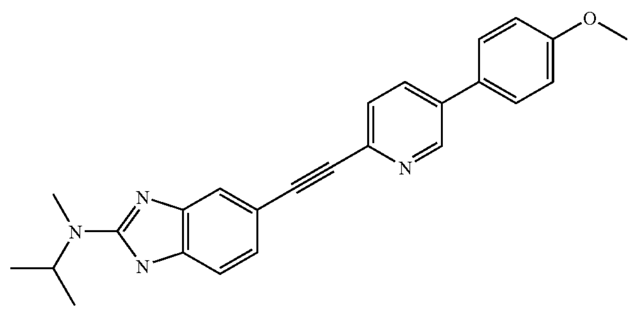 | | | |
| 2.57 | 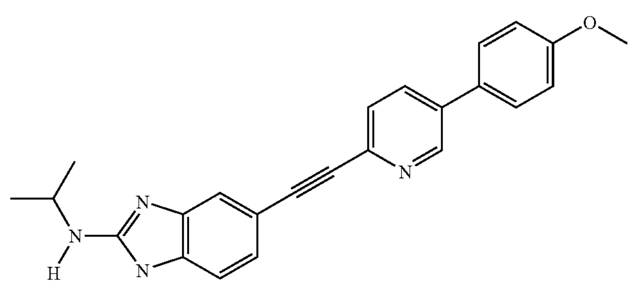 | | | |
| 2.58 | 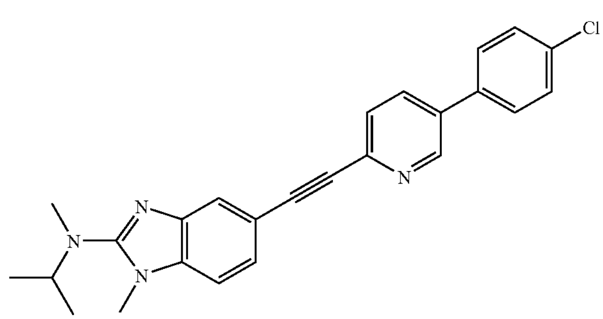 | 85 | 415/417 [M + H]⁺ | 0.21 (R$_f$ silica gel, EtOAc/PE 1:1) |

| Example | Structure | Yield in % | Mass spectrum | retention time HPLC (method) |
|---------|-----------|------------|---------------|------------------------------|
| 2.59 | 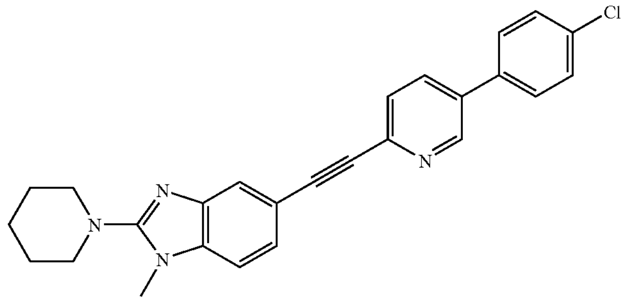 | | | |
| 2.60 | 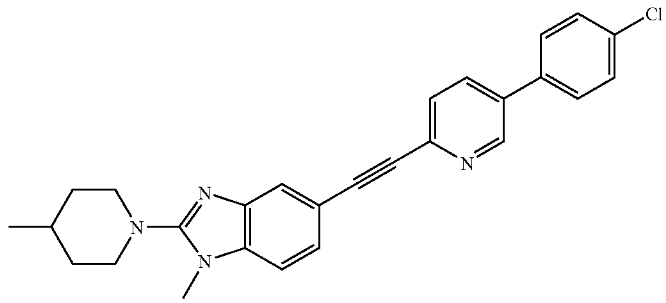 | | | |
| 2.61 | 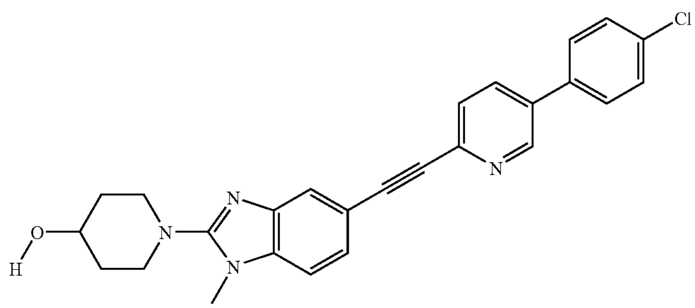 | | | |
| 2.62 | 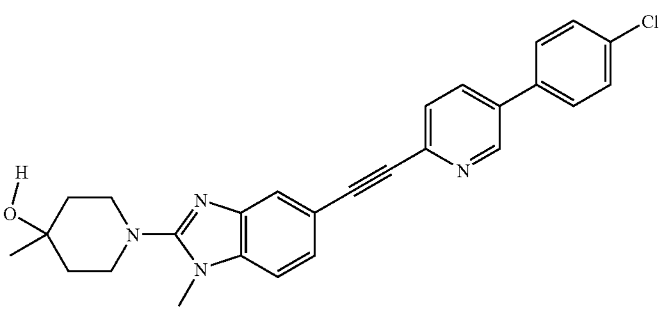 | | | |
| 2.63 | 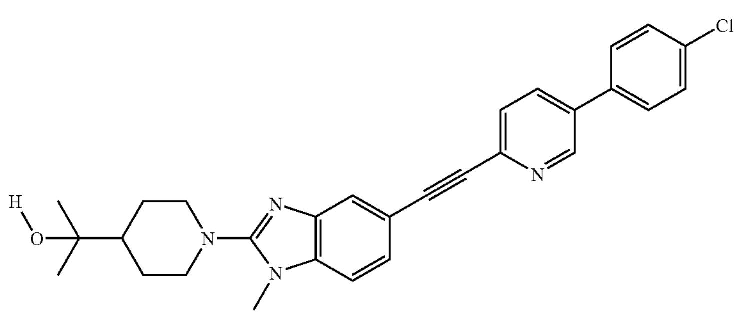 | | | |

-continued

| Example | Structure | Yield in % | Mass spectrum | retention time HPLC (method) |
|---|---|---|---|---|
| 2.64 | 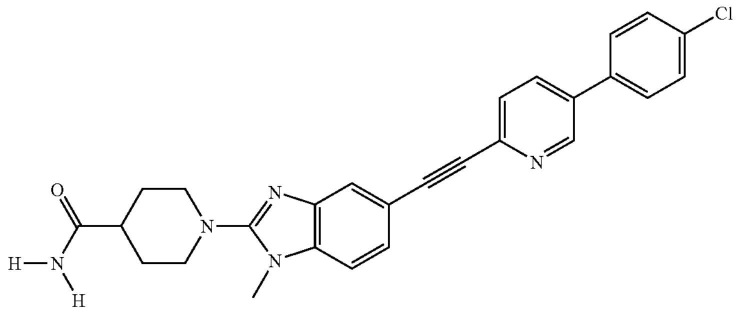 | | | |
| 2.65 | 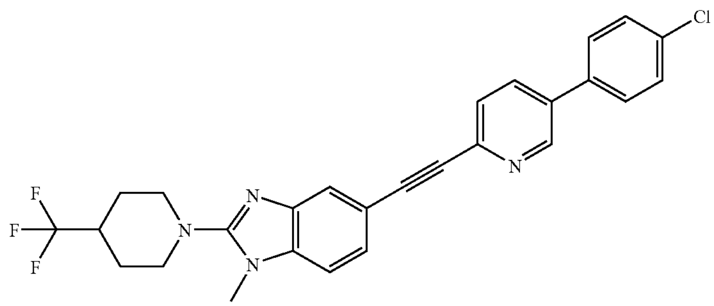 | | | |
| 2.66 | 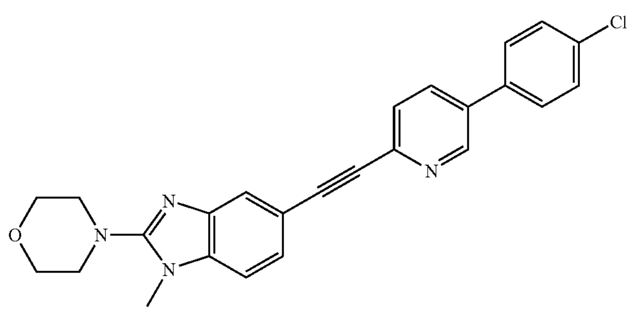 | | | |
| 2.67 | 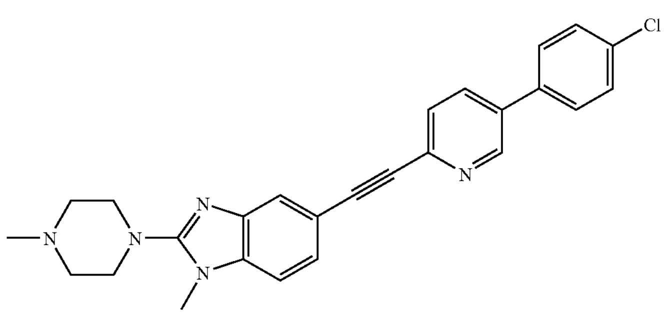 | | | |

| Example | Structure | Yield in % | Mass spectrum | retention time HPLC (method) |
|---|---|---|---|---|
| 2.68 | 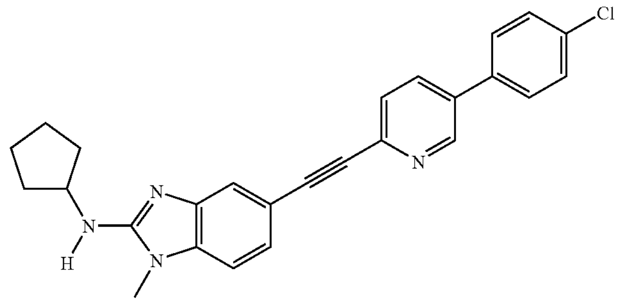 | | | |
| 2.69 | 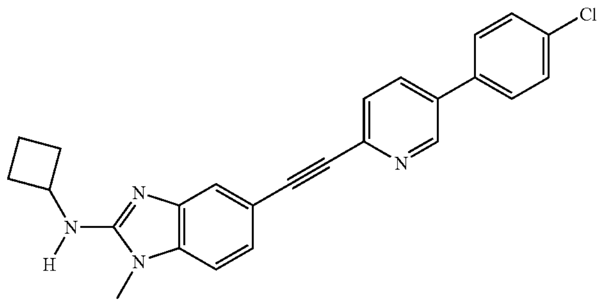 | | | |
| 2.70 | 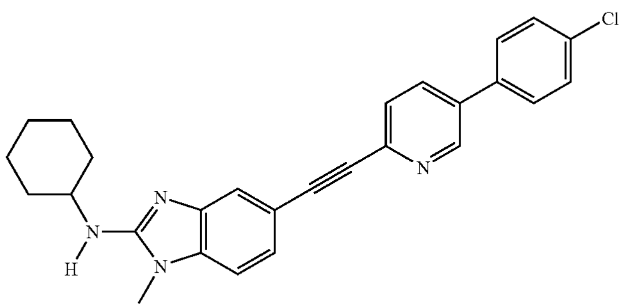 | | | |
| 2.71 | 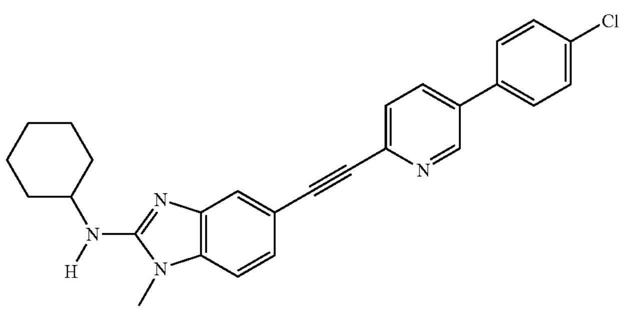 | | | |
| 2.72 | 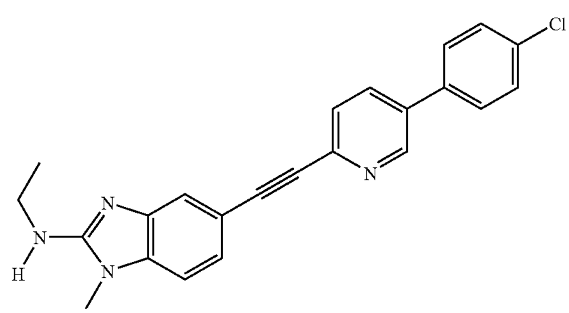 | | | |

| Example | Structure | Yield in % | Mass spectrum | retention time HPLC (method) |
|---|---|---|---|---|
| 2.73 | 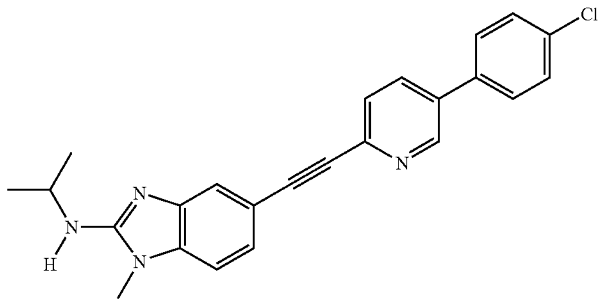 | | | |
| 2.74 | 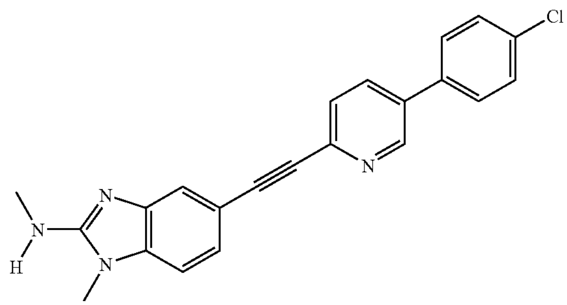 | | | |
| 2.75 | 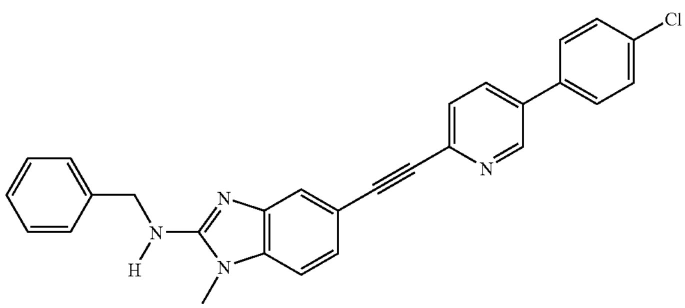 | | | |
| 2.76 | 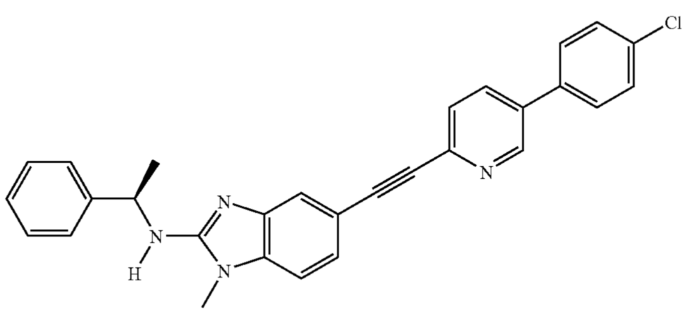 | | | |
| 2.77 | 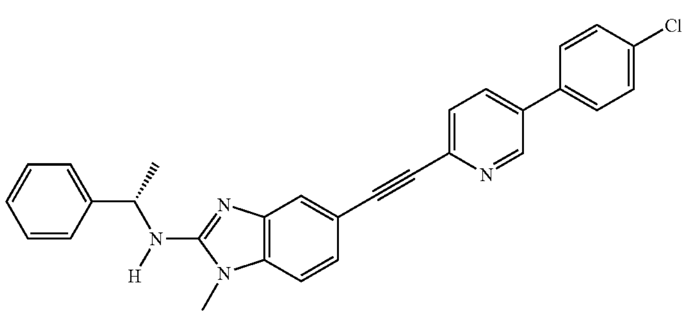 | | | |

| Example | Structure | Yield in % | Mass spectrum | retention time HPLC (method) |
|---|---|---|---|---|
| 2.78 | 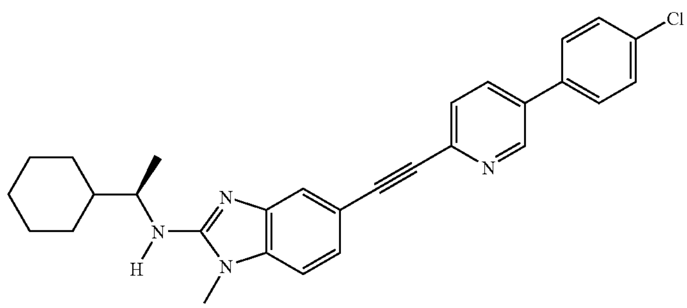 | | | |
| 2.79 | 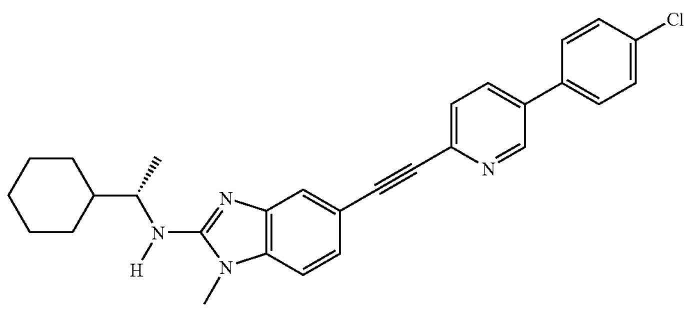 | | | |
| 2.80 | 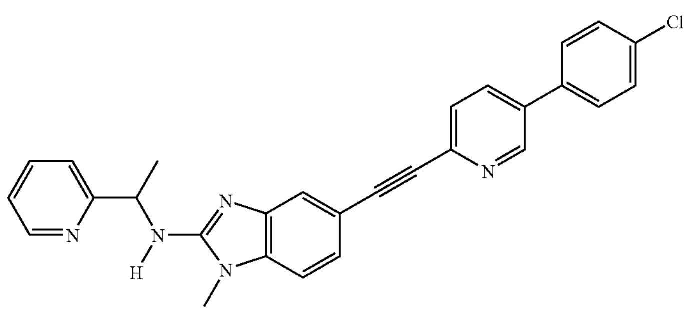 | | | |
| 2.81 | 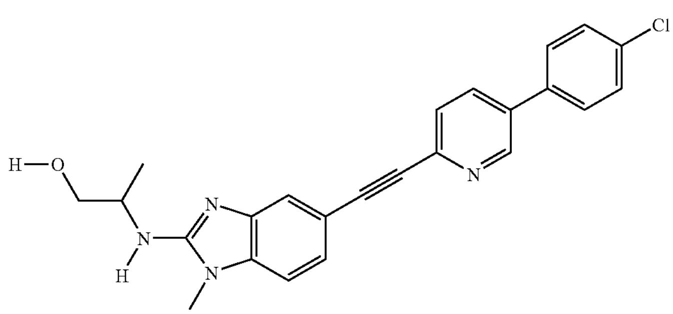 | | | |
| 2.82 | 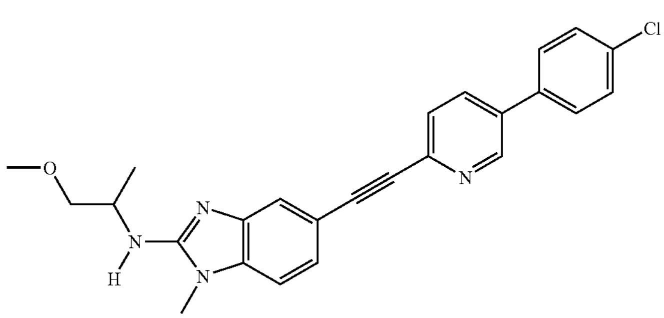 | | | |

-continued

| Example | Structure | Yield in % | Mass spectrum | retention time HPLC (method) |
|---|---|---|---|---|
| 2.83 | 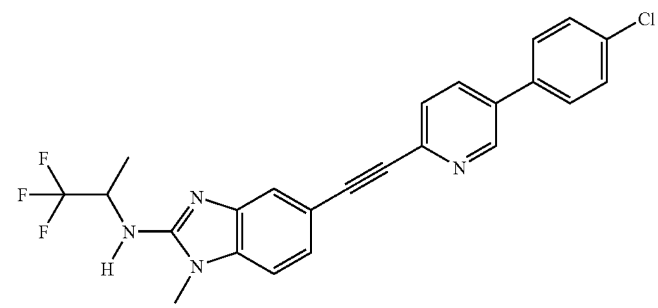 | | | |
| 2.84 | 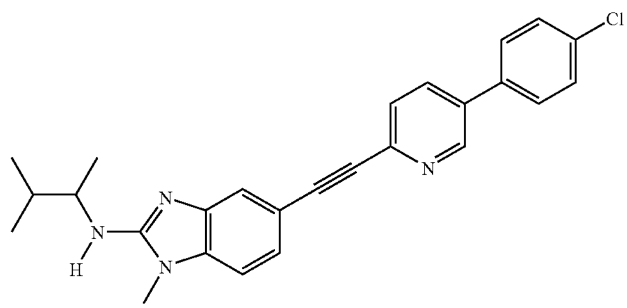 | | | |
| 2.85 | 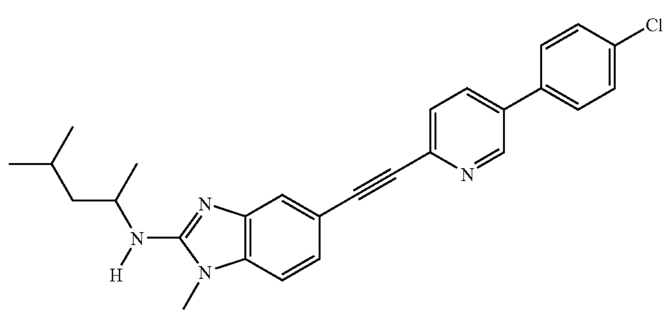 | | | |
| 2.86 | 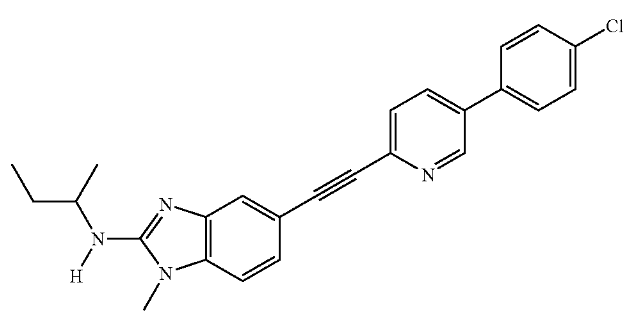 | | | |

-continued

| Example | Structure | Yield in % | Mass spectrum | retention time HPLC (method) |
|---|---|---|---|---|
| 2.87 | 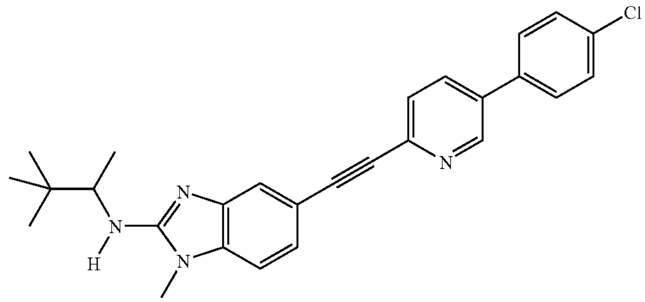 | | | |
| 2.88 | 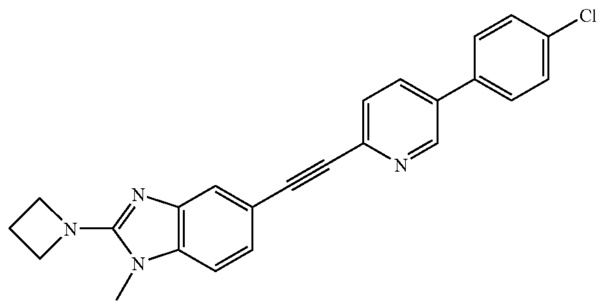 | | | |
| 2.89 | 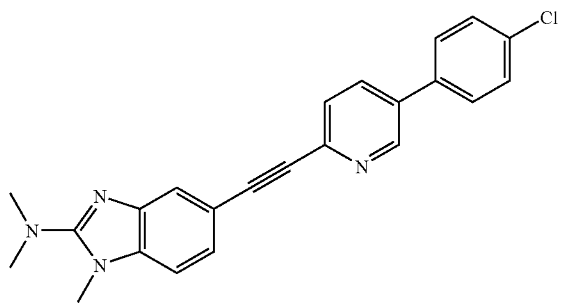 | | | |
| 2.90 | 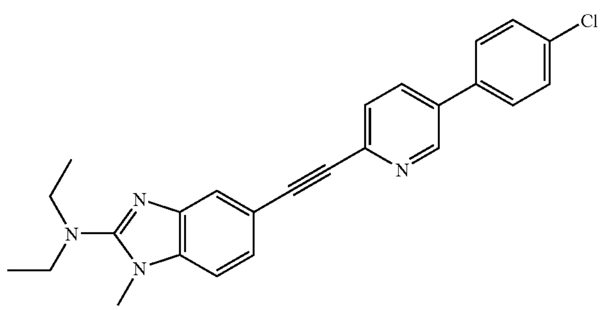 | | | |
| 2.91 | 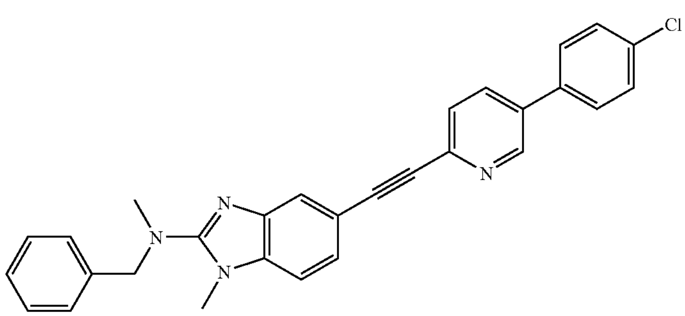 | | | |

-continued

| Example | Structure | Yield in % | Mass spectrum | retention time HPLC (method) |
|---|---|---|---|---|
| 2.92 | 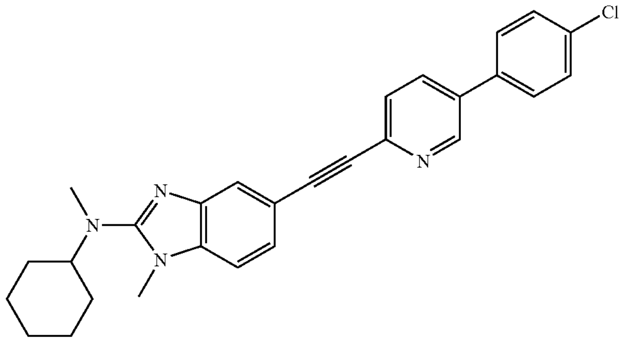 | | | |
| 2.93 | 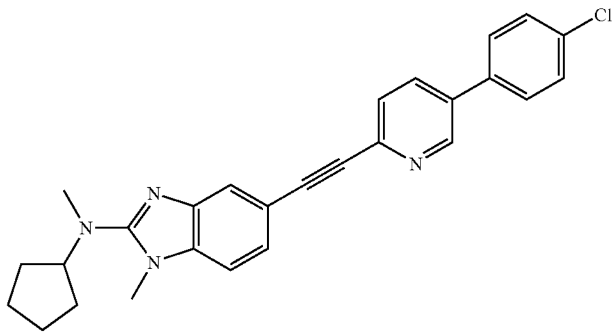 | | | |
| 2.94 | 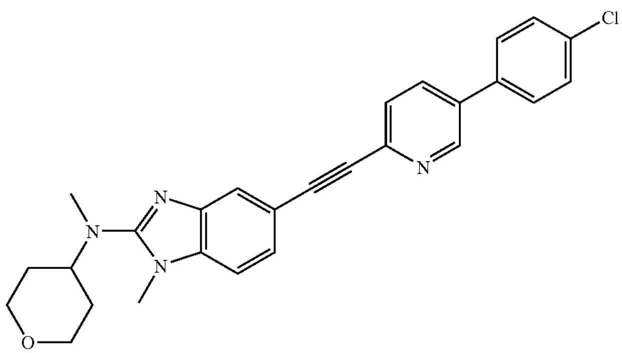 | | | |
| 2.95 | 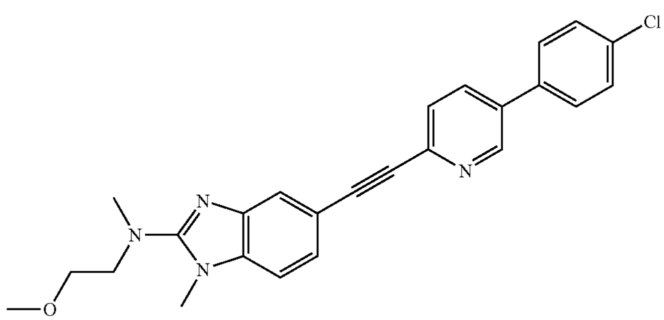 | | | |

-continued

| Example | Structure | Yield in % | Mass spectrum | retention time HPLC (method) |
|---|---|---|---|---|
| 2.96 | 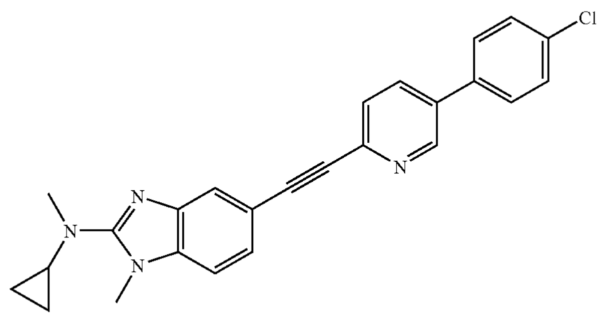 | | | |
| 2.97 | 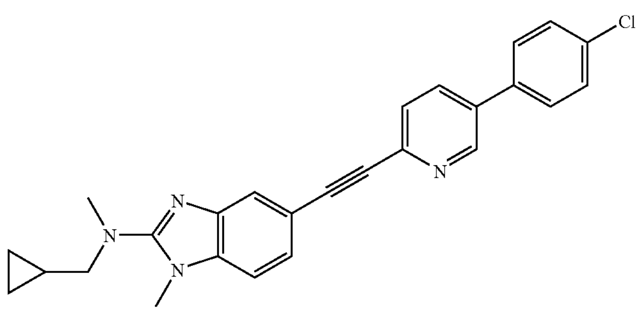 | | | |
| 2.98 | 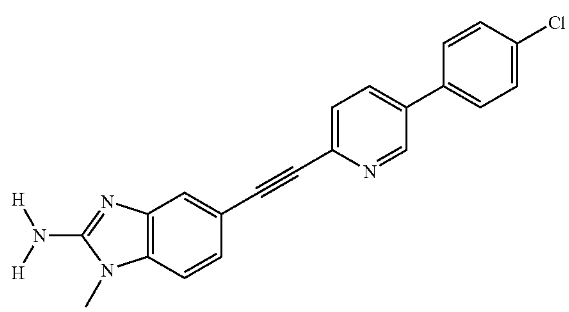 | | | |
| 2.99 | 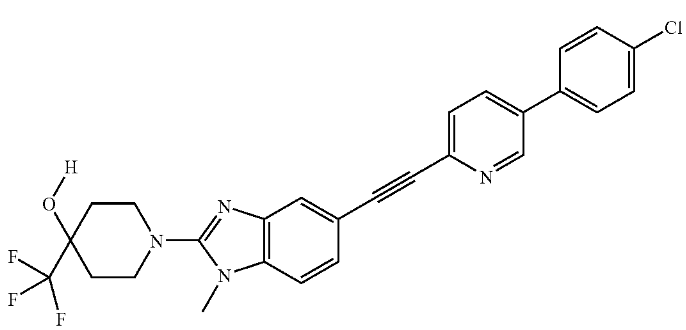 | | | |

-continued

| Example | Structure | Yield in % | Mass spectrum | retention time HPLC (method) |
|---|---|---|---|---|
| 2.100 | 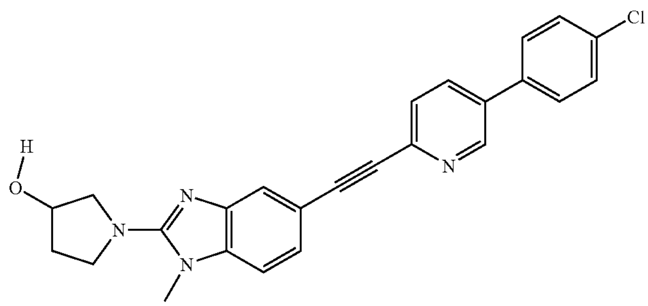 | | | |
| 2.101 | 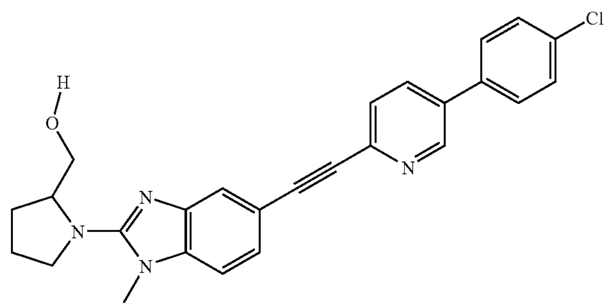 | | | |
| 2.102 | 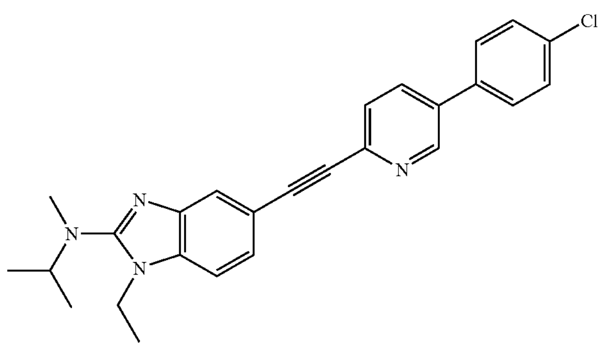 | | | |
| 2.103 | 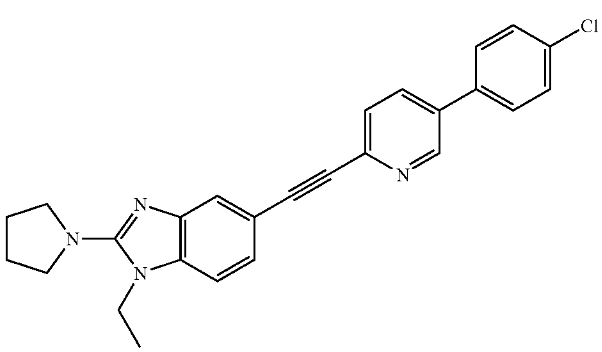 | | | |

| Example | Structure | Yield in % | Mass spectrum | retention time HPLC (method) |
|---|---|---|---|---|
| 2.104 | 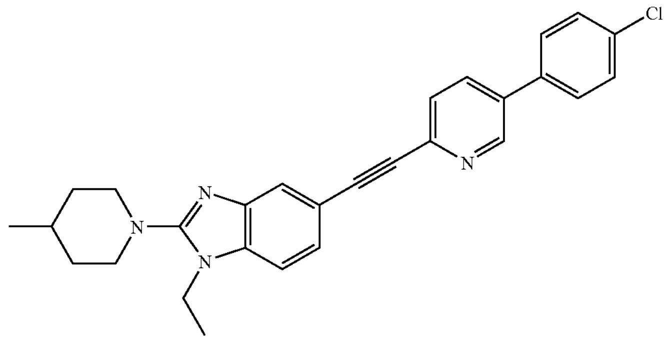 | | | |
| 2.105 | 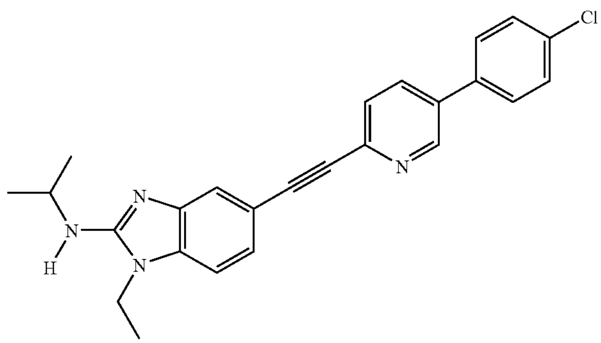 | | | |

Some test methods for determining an MCH-receptor antagonistic activity will now be described. In addition, other test methods known to the skilled person may be used, e.g., by inhibiting the MCH-receptor-mediated inhibition of cAMP production, as described in M. Hoogduijn et al., *Melanin-concentrating hormone and its receptor are expressed and functional in human skin*, Biochem. Biophys. Res Commun. 296 (2002) pp. 698-701, and by biosensory measurement of the binding of MCH to the MCH receptor in the presence of antagonistic substances by plasmon resonance, as described in O. P. Karlsson and S. Lofas, *Flow-Mediated On-Surface Reconstitution of G-Protein Coupled Receptors for Applications in Surface Plasmon Resonance Biosensors*, Anal. Biochem. 300 (2002), pp. 132-138. Other methods of testing antagonistic activity to MCH receptors are contained in the references and patent documents mentioned hereinbefore, and the description of the test methods used is hereby incorporated in this application.

MCH-1 Receptor Binding Test
Method: MCH binding to HMCH-$^1$R transfected cells
Species: Human
Test cell: hMCH-1R stably transfected into CHO/Galpha16 cells
Results: IC$_{50}$ values Membranes from CHO/Galpha16 cells stably transfected with human hMCH-1R are resuspended using a syringe (needle 0.6×25 mm) and diluted in test buffer (50 mM HEPES, 10 mM MgCl$_2$, 2 mM EGTA, pH 7.00; 0.1% bovine serum albumin (protease-free), 0.021% bacitracin, 1 μg/mL aprotinin, 1 μg/mL leupeptin and 1 μM phosphoramidone) to a concentration of 5 to 15 μg/mL. 200 μL of this membrane fraction (contains 1 to 3 μg of protein) are incubated for 60 minutes at ambient temperature with 100 μM of $^{125}$I-tyrosyl melanin concentrating hormone ($^{125}$I-MCH commercially obtainable from NEN) and increasing concentrations of the test compound in a final volume of 250 μL. After the incubation, the reaction is filtered using a cell harvester through 0.5% PEI treated fiberglass filters (GF/B, Unifilter Packard). The membrane-bound radioactivity retained on the filter is then determined after the addition of scintillator substance (Packard Microscint 20) in a measuring device (TopCount of Packard). The non-specific binding is defined as bound radioactivity in the presence of 1 micromolar MCH during the incubation period. The analysis of the concentration binding curve is carried out on the assumption of one receptor binding site. Standard: Non-labeled MCH competes with labeled $^{125}$I-MCH for the receptor binding with an IC50 value of between 0.06 and 0.15 nM. The KD value of the radioligand is 0.156 nM.

MCH-1 Receptor-Coupled Ca$^{2+}$ Mobilization Test
Method: Calcium mobilization test with human MCH (FLIPR$^{384}$)
Species: Human
Test cells: CHO/Galpha 16 cells stably transfected with hMCH—R1
Results: 1st measurement: % stimulation of the reference (MCH 10$^{-6}$ M); 2nd measurement: pKB value

| Reagents: | HBSS (10×) | (GIBCO) |
|---|---|---|
| | HEPES buffer (1M) | (GIBCO) |
| | Pluronic F-127 | (Molecular Probes) |
| | Fluo-4 | (Molecular Probes) |

-continued

| | |
|---|---|
| Probenecid | (Sigma) |
| MCH | (Bachem) |
| bovine serum albumin (protease-free) | (Serva) |
| DMSO | (Serva) |
| Ham's F12 | (Bio Whittaker) |
| FCS | (Bio Whittaker) |
| L-Glutamine | (GIBCO) |
| Hygromycin B | (GIBCO) |
| PENStrep | (Bio Whittaker) |
| Zeocin | (Invitrogen) |

Clonal CHO/Galpha16 hMCH-R1 cells are cultivated in Ham's F12 cell culture medium (with L-glutamine; BioWhittaker; Cat. No. BE12-615F). This contains per 500 mL: 10% FCS, 1% PENStrep, 5 mL of L-glutamine (200 mM stock solution), 3 mL of hygromycin B (50 mg/mL in PBS), and 1.25 mL of zeocin (100 µg/mL stock solution). One day before the experiment the cells are plated on a 384-well microtiter plate (black-walled with a transparent base, made by Costar) in a density of 2500 cells per cavity and cultivated in the above medium overnight at 37° C., 5% $CO_2$, and 95% relative humidity. On the day of the experiment, the cells are incubated with cell culture medium to which 2 mM Fluo-4 and 4.6 mM Probenicid have been added, at 37° C. for 45 minutes. After charging with fluorescent dye, the cells are washed four times with Hanks buffer solution (1× HBSS, 20 mM HEPES), which has been combined with 0.07% Probenicid. The test substances are diluted in Hanks buffer solution, combined with 2.5% DMSO. The background fluorescence of non-stimulated cells is measured in the presence of substance in the 384-well microtiter plate five minutes after the last washing step in the FLIPR$^{384}$ apparatus (Molecular Devices; excitation wavelength: 488 nm; emission wavelength: bandpass 510 to 570 nm). To stimulate the cells MCH is diluted in Hanks buffer with 0.1% BSA, pipetted into the 384-well cell culture plate 35 minutes after the last washing step and the MCH-stimulated fluorescence is then measured in the FLIPR$^{384}$ apparatus.

Data Analysis:
1st measurement: The cellular $Ca^{2+}$ mobilization is measured as the peak of the relative fluorescence minus the background and is expressed as the percentage of the maximum signal of the reference (MCH $10^{-6}$ M). This measurement serves to identify any possible agonistic effect of a test substance.

2nd measurement: The cellular $Ca^{2+}$ mobilization is measured as the peak of the relative fluorescence minus the background and is expressed as the percentage of the maximum signal of the reference (MCH $10^{-6}$ M, signal is standardized to 100%). The EC50 values of the MCH dosage activity curve with and without test substance (defined concentration) are determined graphically by the GraphPad Prism 2.01 curve program. MCH antagonists cause the MCH stimulation curve to shift to the right in the graph plotted.

The inhibition is expressed as a pKB value:

$$pKB = \log(EC_{50(testsubstance+MCH)}/EC_{50(MCH)} - 1) - \log C_{(testsubstance)}$$

The compounds according to the invention, including their salts, exhibit an MCH-receptor antagonistic activity in the tests mentioned above. Using the MCH-1 receptor binding test described above an antagonistic activity is obtained in a dosage range from about $10^{-10}$ M to $10^{-5}$ M, particularly from $10^{-9}$ M to $10^{-6}$ M.

The following $IC_{50}$ values were determined using the MCH-1 receptor binding test described above:

| Compound according to Example no. | Name of substance | $IC_{50}$ value |
|---|---|---|
| 1.44 | {6-[5-(4-chlorophenyl)pyridin-2-ylethynyl]-4-methylquinolin-2-yl}isopropylamine | 6.8 nM |
| 1.43 | 6-[5-(4-chlorophenyl)pyridin-2-ylethynyl]-4-methyl-2-(4-methylpiperidin-1-yl)quinoline | 246 nM |

Some examples of formulations will be described hereinafter, wherein the term "active substance" denotes one or more compounds according to the invention, including their salts. In the case of one of the combinations with one or more active substances described, the term "active substance" also includes the additional active substances.

EXAMPLE A

Capsules for Powder Inhalation Containing 1 mg Active Substance

Composition:
1 capsule for powder inhalation contains:

| | |
|---|---|
| active substance | 1.0 mg |
| lactose | 20.0 mg |
| hard gelatin capsules | 50.0 mg |
| | 71.0 mg |

Preparation: The active substance is ground to the particle size required for inhalation. The ground active substance is homogeneously mixed with the lactose. The mixture is packed into hard gelatin capsules.

EXAMPLE B

Inhalable Solution for Respimat® Containing 1 mg Active Substance

Composition:
1 spray contains:

| | |
|---|---|
| active substance | 1.0 mg |
| benzalkonium chloride | 0.002 mg |
| disodium edetate | 0.0075 mg |
| purified water | to 15.0 µL |

Preparation: The active substance and benzalkonium chloride are dissolved in water and packed into Respimat® cartridges.

EXAMPLE C

Inhalable Solution for Nebulizer Containing 1 mg Active Substance

Composition:
1 vial contains:

| | |
|---|---|
| active substance | 0.1 g |
| sodium chloride | 0.18 g |
| benzalkonium chloride | 0.002 g |
| purified water | to 20.0 mL |

Preparation: The active substance, sodium chloride, and benzalkonium chloride are dissolved in water.

EXAMPLE D

Propellant Type Metered Dose Aerosol Containing 1 mg Active Substance

Composition:
1 spray contains:

| | |
|---|---|
| active substance | 1.0 mg |
| lecithin | 0.1% |
| propellant gas | to 50.0 µL |

Preparation: The micronized active substance is homogeneously suspended in the mixture of lecithin and propellant gas. The suspension is transferred into a pressurised container with a metering valve.

EXAMPLE E

Nasal Spray Containing 1 mg Active Substance

Composition:

| | |
|---|---|
| active substance | 1.0 mg |
| sodium chloride | 0.9 mg |
| benzalkonium chloride | 0.025 mg |
| disodium edetate | 0.05 mg |
| purified water | to 0.1 mL |

Preparation: The active substance and the excipients are dissolved in water and transferred into a corresponding container.

EXAMPLE F

Injectable Solution Containing 5 mg of Active Substance Per 5 mL

Composition:

| | |
|---|---|
| active substance | 5 mg |
| glucose | 250 mg |
| human serum albumin | 10 mg |
| glycofurol | 250 mg |
| water for injections | to 5 mL |

Preparation: Glycofurol and glucose are dissolved in water for injections (WfI); human serum albumin is added; active ingredient is dissolved with heating; made up to specified volume with WfI; transferred into ampoules under nitrogen gas.

EXAMPLE G

Injectable Solution Containing 100 mg of Active Substance Per 20 mL

Composition:

| | |
|---|---|
| active substance | 100 mg |
| monopotassium dihydrogen phosphate = $KH_2PO_4$ | 12 mg |
| disodium hydrogen phosphate = $Na_2HPO_4 \cdot 2H_2O$ | 2 mg |
| sodium chloride | 180 mg |
| human serum albumin | 50 mg |
| Polysorbate 80 | 20 mg |
| water for injections | to 20 mL |

Preparation: Polysorbate 80, sodium chloride, monopotassium dihydrogen phosphate, and disodium hydrogen phosphate are dissolved in water for injections (WfI); human serum albumin is added; active ingredient is dissolved with heating; made up to specified volume with WfI; transferred into ampoules.

EXAMPLE H

Lyophilisate Containing 10 mg of Active Substance

Composition:

| | |
|---|---|
| Active substance | 10 mg |
| Mannitol | 300 mg |
| human serum albumin | 20 mg |

Preparation: Mannitol is dissolved in water for injections (WfI); human serum albumin is added; active ingredient is dissolved with heating; made up to specified volume with WfI; transferred into vials; freeze-dried.

Solvent for lyophilisate:

| | |
|---|---|
| Polysorbate 80 = Tween 80 | 20 mg |
| mannitol | 200 mg |
| water for injections | to 10 mL |

Preparation: Polysorbate 80 and mannitol are dissolved in water for injections (WfI); transferred into ampoules.

EXAMPLE I

Tablets Containing 20 mg of Active Substance

Composition:

| | |
|---|---|
| active substance | 20 mg |
| lactose | 120 mg |
| maize starch | 40 mg |
| magnesium stearate | 2 mg |
| Povidone K 25 | 18 mg |

Preparation: Active substance, lactose, and maize starch are homogeneously mixed; granulated with an aqueous solution of povidone; mixed with magnesium stearate; compressed in a tablet press; weight of tablet: 200 mg.

EXAMPLE J

Capsules Containing 20 mg Active Substance

Composition:

| | |
|---|---|
| active substance | 20 mg |
| maize starch | 80 mg |
| highly dispersed silica | 5 mg |
| magnesium stearate | 2.5 mg |

Preparation: Active substance, maize starch, and silica are homogeneously mixed; mixed with magnesium stearate; the mixture is packed into size 3 hard gelatin capsules in a capsule filling machine.

EXAMPLE K

Suppositories Containing 50 mg of Active Substance

Composition:

| | |
|---|---|
| active substance | 50 mg |
| hard fat (*Adeps solidus*) | q.s. ad 1700 mg |

Preparation: Hard fat is melted at about 38° C.; ground active substance is homogeneously dispersed in the molten hard fat; after cooling to about 35° C. it is poured into chilled moulds.

EXAMPLE L

Injectable Solution Containing 10 mg of Active Substance Per 1 mL

Composition:

| | |
|---|---|
| active substance | 10 mg |
| mannitol | 50 mg |
| human serum albumin | 10 mg |
| water for injections | to 1 mL |

Preparation: Mannitol is dissolved in water for injections (WfI); human serum albumin is added; active ingredient is dissolved with heating; made up to specified volume with WfI; transferred into ampoules under nitrogen gas.

We claim:
1. A compound of formula I

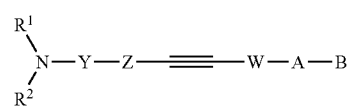

I wherein:
$R^1$ and $R^2$ are each independently H, $C_{1-8}$-alkyl, $C_{3-7}$-cycloalkyl, or a phenyl or pyridinyl group optionally mono- or polysubstituted by identical or different groups $R^{20}$ and/or monosubstituted by nitro, wherein the alkyl or cycloalkyl group are optionally mono- or polysubstituted by identical or different groups $R^{11}$, and a —$CH_2$— group in position 3 or 4 of a 5-, 6-, or 7-membered cycloalkyl group may be replaced by —O—, —S—, or —$NR^{13}$—, or $R^1$ and $R^2$ are linked together, such that $R^1R^2N$— denotes a group which is selected from pyrrolidine, piperidine, piperazine in which the free imine function is substituted by $R^{13}$, and morpholine, wherein in the alkylene bridge one or more H atoms are optionally replaced by identical or different groups $R^{14}$, and the alkylene bridge is optionally substituted by one or two identical or different carbo- or heterocyclic groups Cy in such a way that the bond between the alkylene bridge and the group Cy is made via a single or double bond, via a common C atom to form a spirocyclic ring system, via two common adjacent C and/or N atoms to form a fused bicyclic ring system, or via three or more C and/or N atoms to form a bridged ring system;

W and Z are each independently a single bond or a $C_{1-2}$-alkylene bridge, wherein two adjacent C atoms are optionally joined together with an additional $C_{1-4}$-alkylene bridge, and one or two C atoms are independently substituted by one or two identical or different $C_{1-3}$-alkyl groups, wherein two alkyl groups are optionally joined together to form a carbocyclic ring;

Y denotes:

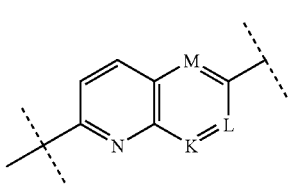

Y1

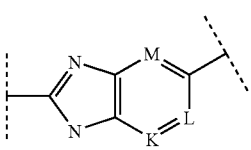

Y6 wherein the groups M, K, and L represent a CH group, and in the partial formulae Y1, and Y6 one or more CH groups may be substituted independently of one another by $R^{20}$, and in partial formula Y6 an NH group may be substituted by $C_{1-4}$ alkyl A is phenyl, pyridinyl, pyrimidinyl, pyrazinyl, or pyridazinyl, each optionally mono- or polysubstituted at one or more C atoms by identical or different groups $R^{20}$, or, in the case of a phenyl ring, is optionally additionally monosubstituted by nitro;

B is independently selected from the group comprising phenyl, pyridyl, thienyl, and furanyl, or denotes $C_{1-6}$-alkyl, $C_{1-6}$-alkenyl, $C_{1-6}$-alkynyl, $C_{3-7}$-cycloalkyl, $C_{5-7}$cycloalkenyl, $C_{3-7}$cycloalkyl-$C_{1-3}$-alkyl, $C_{3-7}$-cycloalkenyl-$C_{1-3}$-alkyl, $C_{3-7}$- cycloalkyl-$C_{1-3}$-alkenyl, or $C_{3-7}$-cycloalkyl-$C_{1-3}$-alkynyl, wherein one or more C atoms are optionally independently mono- or polysubstituted by halogen and/or monosubstituted by hydroxy or cyano and/or cyclic groups are optionally mono- or polysubstituted by identical or different groups $R^{20}$;

Cy is $C_{3-7}$-cycloalkyl and aza-$C_{4-7}$-cycloalkyl, while the group Cy may be mono- or polysubstituted by $R^{20}$;

$R^{11}$ is halogen, $C_{1-6}$-alkyl, $C_{2-6}$-alkenyl, $C_{2-6}$-alkynyl, $R^{15}$—O—, $R^{15}$—O—CO—, $R^{15}$—CO—O—, cyano, $R^{16}R^{17}N$, $R^{18}R^{19}N$—CO— or Cy, wherein one or more C atoms thereof are optionally independently substituted by halogen, OH, CN, $CF_3$, $C_{1-3}$-alkyl, or hydroxy-$C_{1-3}$-alkyl;

$R^{13}$ independently is $R^{17}$, $R^{14}$ is F, Cl, Br, cyano, $C_{1-4}$-alkyl, $C_{2-4}$-alkenyl, $C_{2-4}$-alkynyl, $C_{3-7}$-cycloalkyl, $C_{3-7}$-cycloalkyl-$C_{1-3}$-alkyl, hydroxy, hydroxy-$C_{1-3}$-alkyl, $C_{1-4}$-alkoxy, ω-($C_{1-4}$ alkoxy)-$C_{1-3}$-alkyl, $C_{1-4}$-alkyl-carbonyl, carboxy, $C_{1-4}$-alkoxycarbonyl, hydroxy-carbonyl-$C_{1-3}$-alkyl, $C_{1-4}$-alkoxy-carbonyl-$C_{1-3}$-alkyl, $C_{1-4}$-alkoxy-carbonylamino, $C_{1-4}$-alkoxy-carbonylamino-$C_{1-3}$-alkyl, amino, $C_{1-4}$alkyl-amino, $C_{3-7}$cycloalkyl-amino, N—($C_{3-7}$-cycloalkyl)—N—($C_{1-4}$-alkyl)-amino, di-($C_{1-4}$-alkyl)-amino, cyclo-$C_{3-6}$-alkyleneimino, amino-$C_{1-3}$-alkyl, $C_{1-4}$-alkyl-amino-$C_{1-3}$-alkyl, $C_{3-7}$-cycloalkyl-amino-$C_{1-3}$-alkyl, N—($C_{3-7}$-cycloalkyl)—N—($C_{1-4}$-alkyl)-amino-$C_{1-3}$-alkyl, di-($C_{1-4}$-alkyl)-amino-$C_{1-3}$-alkyl, cyclo-$C_{3-6}$-alkyleneimino-$C_{1-3}$-alkyl, aminocarbonyl, $C_{1-4}$-alkyl-aminocarbonyl, $C_{3-7}$-cycloalkyl-aminocarbonyl, N—($C_{3-7}$cycloalkyl)—N—($C_{1-4}$-alkyl)-aminocarbonyl, di-($C_{1-4}$-alkyl)-aminocarbonyl, pyridinyloxy, pyridinylamino, or pyridinyl-$C_{1-3}$-alkyl-amino;

$R^{15}$ is H, $C_{1-4}$-alkyl, $C_{3-7}$-cycloalkyl, $C_{3-7}$-cycloalkyl-$C_{1-3}$-alkyl, phenyl, phenyl-$C_{1-3}$-alkyl, pyridinyl, or pyridinyl-$C_{1-3}$-alkyl;

$R^{16}$ is H, $C_{1-6}$-alkyl, $C_{3-7}$-cycloalkyl, $C_{3-7}$-cycloalkyl-$C_{1-3}$-alkyl, $C_{4-7}$-cycloalkenyl, $C_{4-7}$-cycloalkenyl-$C_{1-3}$-alkyl, ω-hydroxy-$C_{2-3}$-alkyl, ω-($C_{1-4}$-alkoxy)-$C_{2-3}$-alkyl, amino-$C_{2-6}$- alkyl, $C_{1-4}$-alkyl-amino-$C_{2-6}$-alkyl, di-($C_{1-4}$-alkyl)-amino-$C_{2-6}$-alkyl, or cyclo-$C_{3-6}$-alkyleneimino-$C_{2-6}$-alkyl;

$R^{17}$ is independently $R^{16}$ or phenyl, phenyl-$C_{1-3}$-alkyl, pyridinyl, $C_{1-4}$-alkylcarbonyl, hydroxycarbonyl-$C_{1-3}$-alkyl, $C_{1-4}$-alkoxycarbonyl, $C_{1-4}$-alkoxycarbonyl-$C_{1-3}$-alkyl, $C_{1-4}$-alkylcarbonylamino-$C_{2-3}$-alkyl, N—($C_{1-4}$-alkylcarbonyl)—N—($C_{1-4}$-alkyl)-amino-$C_{2-3}$-alkyl, $C_{1-4}$-alkylsulfonyl, $C_{1-4}$-alkylsulfonylamino-$C_{2-3}$-alkyl, or N—($C_{1-4}$-alkylsulfonyl)—N(—$C_{1-4}$-alkyl)-amino-$C_{2-3}$-alkyl;

$R^{18}$ and $R^{19}$ are each independently H or $C_{1-6}$-alkyl;

$R^{20}$ is halogen, hydroxy, cyano, $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, hydroxy-$C_{1-3}$-alkyl, $R^{22}$-$C_{1-3}$-alkyl, or is independently $R^{22}$;

$R^{21}$ is $C_{1-4}$-alkyl, ω-hydroxy-$C_{2-6}$-alkyl, ω-$C_{1-4}$-alkoxy-$C_{2-6}$-alkyl, ω-$C_{1-4}$-alkyl-amino-$C_{2-6}$-alkyl, ω-di-($C_{1-4}$-alkyl)-amino-$C_{2-6}$-alkyl, ω-cyclo-$C_{3-6}$-alkyleneimino-$C_{2-6}$-alkyl, phenyl, phenyl-$C_{1-3}$-alkyl, $C_{1-4}$-alkylcarbonyl, $C_{1-4}$-alkoxy-carbonyl, $C_{1-4}$-alkylsulfonyl, aminosulfonyl, $C_{1-4}$-alkylaminosulfonyl, di-$C_{1-4}$-alkylaminosulfonyl, or cyclo-$C_{3-6}$-alkylene-iminosulfonyl; and $R^{22}$ is $C_{1-4}$-alkoxy, $C_{1-4}$-alkylthio, $C_{1-4}$-alkylcarbonyl, $C_{1-4}$-alkoxycarbonyl, aminocarbonyl, $C_{1-4}$-alkylaminocarbonyl, di-($C_{1-4}$-alkyl)-aminocarbonyl, $C_{1-4}$-alkylsulfonyl, $C_{1-4}$-alkyl-sulfinyl, $C_{1-4}$-alkyl-sulfonylamino, amino, $C_{1-4}$-alkylamino, di-($C_{1-4}$-alkyl)-amino, $C_{1-4}$alkyl-carbonylamino, hydroxy-$C_{1-3}$-alkylaminocarbonyl, aminocarbonylamino, or $C_{1-4}$alkylaminocarbonylamino, wherein in each of the abovementioned groups and residues one or more C atoms are additionally optionally mono- or polysubstituted by F and/or one or two C atoms are independently optionally monosubstituted by Cl or Br and/or one or more phenyl rings independently optionally contain one, two, or three substituents selected from F, Cl, Br, I, cyano, $C_{1-4}$-alkyl, $C_{1-4}$-alkoxy, difluoromethyl, trifluoromethyl, hydroxy, amino, $C_{1-3}$-alkylamino, di-($C_{1-3}$-alkyl)-amino, acetylamino, aminocarbonyl, difluoromethoxy, trifluoromethoxy, amino-$C_{1-3}$-alkyl, $C_{1-3}$-alkylamino-$C_{1-3}$-alkyl-, and di-($C_{1-3}$-alkyl)-amino-$C_{1-3}$-alkyl and/or are optionally monosubstituted by nitro, and the H atom of any carboxy group present or an H atom bound to an N atom are each optionally replaced by a group which can be cleaved in vivo, and the tautomers, enantiomers, salts, and mixtures thereof.

2. The compound of formula (I) according to claim 1, wherein:

$R^1$ and $R^2$ are independently H, $C_{1-6}$-alkyl, $C_{3-5}$-alkenyl, $C_{3-5}$-alkynyl, $C_{3-7}$-cycloalkyl, hydroxy-$C_{3-7}$-cycloalkyl, $C_{3-7}$-cycloalkyl-$C_{1-3}$-alkyl, (hydroxy-$C_{3-7}$-cycloalkyl)-$C_{1-3}$-alkyl, hydroxy-$C_{2-4}$-alkyl, ω—NC—$C_{2-3}$ -alkyl, $C_{1-4}$-alkoxy-$C_{2-4}$-alkyl, hydroxy-$C_{1-4}$-alkoxy- $C_{2-4}$-alkyl, $C_{1-4}$-alkoxy-carbonyl-$C_{1-4}$-alkyl, carboxyl-$C_{1-4}$-alkyl, amino-$C_{2-4}$-alkyl, $C_{1-4}$-alkyl-amino-$C_{2-4}$-alkyl, di-($C_{1-4}$-alkyl)-amino-$C_{2-4}$-alkyl, cyclo-$C_{3-6}$-alkyleneimino-$C_{2-4}$- alkyl, pyrrolidin-3-yl, N—($C_{1-4}$-alkyl)-pyrrolidin-3-yl, pyrrolidinyl-$C_{1-3}$-alkyl, N—($C_{1-4}$-alkyl)-pyrrolidinyl-$C_{1-3}$-alkyl, piperidin-3-yl, piperidin-4-yl, N—($C_{1-4}$-alkyl)-piperidin-3-yl, N—($C_{1-4}$-alkyl)-piperidin-4-yl, piperidinyl-$C_{1-3}$-alkyl, N—($C_{1-4}$-alkyl)-piperidinyl-$C_{1-3}$-alkyl, tetrahydropyran-3-yl, tetrahydropyran-4-yl, tetrahydrofuran-2-ylmethyl, tetrahydrofuran-3-ylmethyl, phenyl, phenyl-$C_{1-3}$-alkyl, pyridyl, or pyridyl-$C_{1-3}$-alkyl, wherein one or more C atoms thereof are optionally independently mono- or polysubstituted by F, $C_{1-3}$-alkyl, or hydroxy-$C_{1-3}$-alkyl, and/or one or two C atoms are independently monosubstituted by Cl, Br, OH, $CF_3$, or CN, and the phenyl or pyridyl group is optionally mono- or polysubstituted by identical or different groups $R^{20}$, or, in the case of a phenyl group, is optionally additionally monosubstituted by nitro.

3. The compound of formula (I) according to claim 1, wherein:

$R^1$ and $R^2$ together with the N atom to which they are bound are selected from the group consisting of

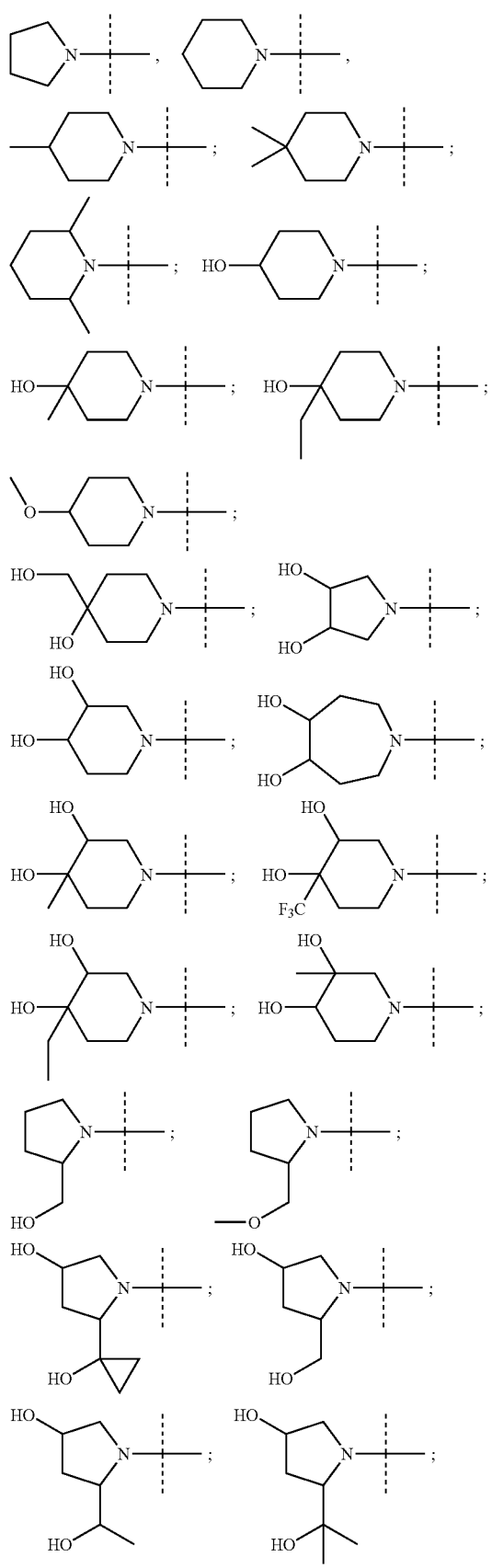

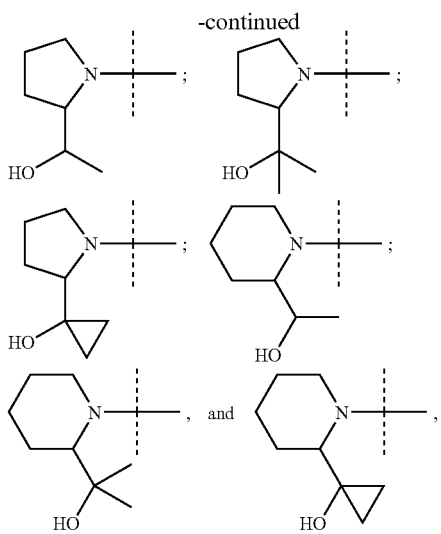

wherein the groups mentioned are not further substituted, or wherein methyl or ethyl groups may be mono-, di-, or trisubstituted by fluorine, and wherein one or more H atoms of the heterocycle formed by the group $R^1R^2N$— which are bound to carbon may be substituted independently of one another by fluorine, chlorine, CN, $CF_3$, $C_{1-3}$-alkyl, or hydroxy-$C_{1-3}$-alkyl, particularly $C_{1-3}$-alkyl or $CF_3$.

4. The compound of formula (I) according to claim 1, wherein:
Z is a single bond or ethylene; and
W is a single bond.

5. The compound of formula (I) according to claim 1, wherein:
Y denotes:

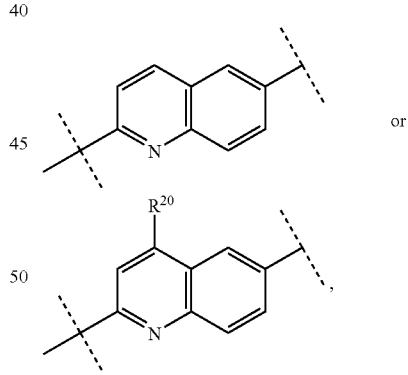

where $R^{20}$ denotes $C_{1-3}$alkyl.

6. The compound of formula (I) according to claim 1, wherein:
A is

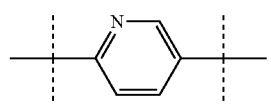

or

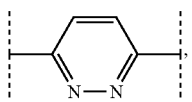

each optionally mono- or polysubstituted at one or more C atoms by identical or different groups $R^{20}$.

7. The compound of formula (I) according to claim 1, wherein:

B is phenyl, cyclohexenyl, pyridyl, thienyl, or furanyl, each optionally mono- or polysubstituted at one or more C atoms by identical or different groups $R^{20}$, or, in the case of a phenyl group, are optionally additionally monosubstituted by nitro.

8. The compound of formula (I) according to claim 1, wherein:

Y is 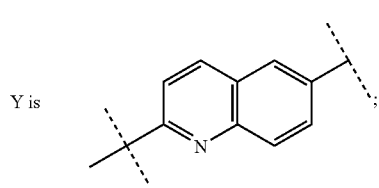

A is 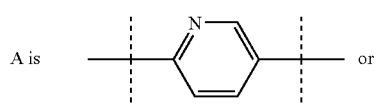 or

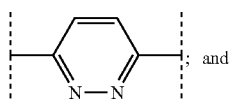 and

B is phenyl, cyclohexenyl, pyridyl, thienyl, or furanyl, wherein Y and A are unsubstituted or monosubstituted by $R^{20}$, and B is unsubstituted or independently mono-, di-, or trisubstituted by $R^{20}$, or, in the case of a phenyl ring, are optionally additionally monosubstituted by nitro.

9. The compound of formula (I) according to claim 1, wherein:

$R^{20}$ is F, Cl, Br, I, OH, cyano, methyl, difluoromethyl, trifluoromethyl, ethyl, n-propyl, isopropyl, amino, acetyl, methoxy, difluoromethoxy, trifluoromethoxy, ethoxy, n-propoxy, or isopropoxy, wherein each $R^{20}$ is identical or different.

10. A physiologically acceptable salt of the compound according to claim 1.

11. A pharmaceutical formulation comprising the compound according to claim 1 and one or more physiologically acceptable excipients or inert carriers or diluents.

12. A pharmaceutical formulation comprising the compound according to claim 2 and one or more physiologically acceptable excipients or inert carriers or diluents.

13. A pharmaceutical formulation comprising the compound according to claim 3 and one or more physiologically acceptable excipients or inert carriers or diluents.

14. A pharmaceutical formulation comprising the physiologically acceptable salt according to claim 10 and one or more physiologically acceptable excipients or inert carriers or diluents.

15. The pharmaceutical formulation according to claim 11 further comprising a second active substance selected from the group consisting of active substances for the treatment of diabetes, active substances for the treatment of diabetic complications, active substances for the treatment of obesity, active substances for the treatment of high blood pressure, active substances for the treatment of hyperlipidemia or arteriosclerosis, active substances for the treatment of arthritis, active substances for the treatment of anxiety states, and active substances for the treatment of depression.

16. The pharmaceutical formulation according to claim 12 further comprising a second active substance selected from the group consisting of active substances for the treatment of diabetes, active substances for the treatment of diabetic complications, active substances for the treatment of obesity, active substances for the treatment of high blood pressure, active substances for the treatment of hyperlipidemia or arteriosclerosis, active substances for the treatment of arthritis, active substances for the treatment of anxiety states, and active substances for the treatment of depression.

17. The pharmaceutical formulation according to claim 13 further comprising a second active substance selected from the group consisting of active substances for the treatment of diabetes, active substances for the treatment of diabetic complications, active substances for the treatment of obesity, active substances for the treatment of high blood pressure, active substances for the treatment of hyperlipidemia or arteriosclerosis, active substances for the treatment of arthritis, active substances for the treatment of anxiety states, and active substances for the treatment of depression.

18. The pharmaceutical formulation according to claim 14 further comprising a second active substance selected from the group consisting of active substances for the treatment of diabetes, active substances for the treatment of diabetic complications, active substances for the treatment of obesity, active substances for the treatment of high blood pressure, active substances for the treatment of hyperlipidemia or arteriosclerosis, active substances for the treatment of arthritis, active substances for the treatment of anxiety states, and active substances for the treatment of depression.

19. A compound selected from the group consisting of:

1.11
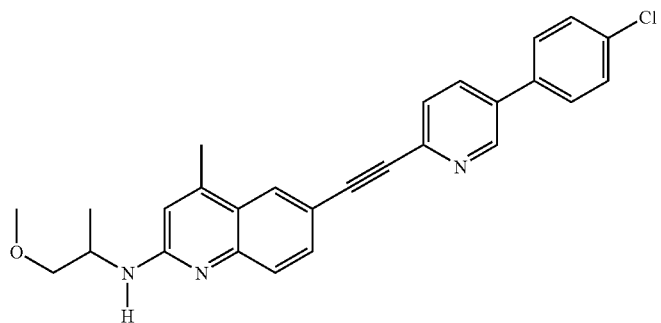

1.42
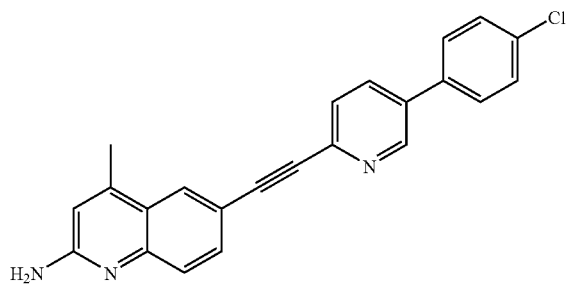

1.44
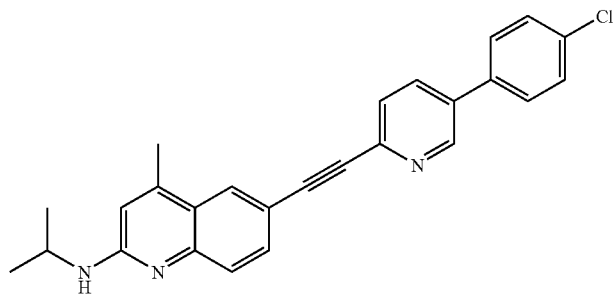

1.51
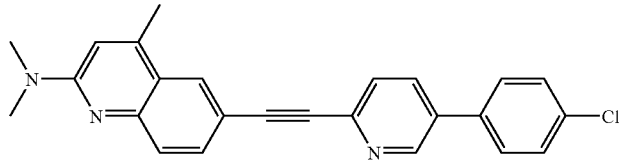

2.2
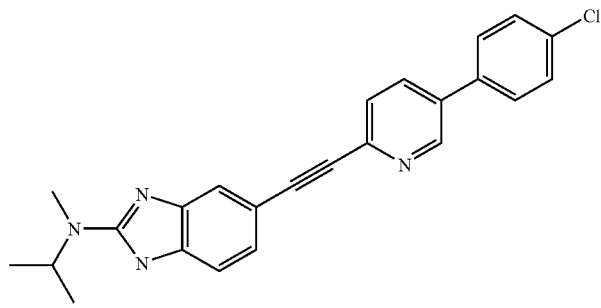

or a pharmaceutically acceptable salt thereof.

20. The compound of formula (I) according to claim 1, wherein:

$R^1$ and $R^2$ are independently H, $C_{1-4}$-alkyl, hydroxy-$C_{1-4}$-alkyl, $C_{3-5}$-alkenyl, $C_{3-5}$-alkynyl, $C_{3-7}$-cycloalkyl, hydroxy-$C_{3-7}$-cycloalkyl, dihydroxy-$C_{3-6}$-alkyl, $C_{3-7}$-cycloalkyl-$C_{1-3}$-alkyl, tetrahydropyran-3-yl, tetrahydropyran-4-yl, tetrahydrofuran-2-ylmethyl, tetrahydrofuran-3-ylmethyl, (hydroxy-$C_{3-7}$-cycloalkyl)-$C_{1-3}$-alkyl, ω-($C_{1-4}$-alkoxy)-$C_{2-3}$-alkyl, di-($C_{1-3}$-alkyl)amino-$C_{2-3}$-alkyl, pyrrolidin—N—yl-$C_{2-3}$-alkyl, piperidin—N—yl-$C_{2-3}$-alkyl, pyridyl, and benzyl, while an alkyl, cycloalkyl or cycloalkyl-alkyl group may additionally be mono- or disubstituted by hydroxy and/or hydroxy-$C_{1-3}$-alkyl, and/or mono- or polysubstituted by F or $C_{1-3}$-alkyl and/or monosubstituted by $CF_3$, Br, Cl, or CN.

21. The compound of formula IIa, IIb, IIc or IId

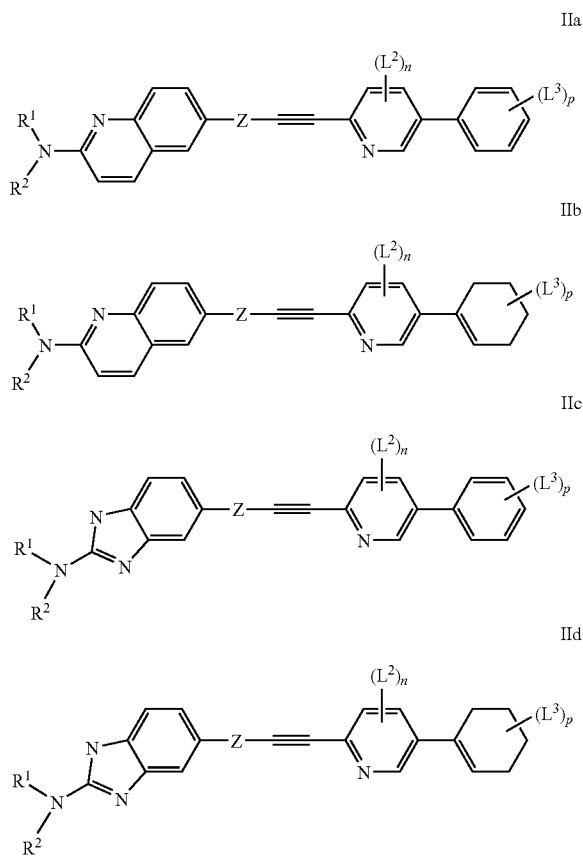

wherein:

the quinoline and benzimidazole groups are unsubstituted or mono- or disubstituted by $L^1$;

$R^1$, $R^2$, and Z are defined as in claim 1, 2, 3 or 4;

$L^1$, $L^2$, and $L^3$ independently of one another have one of the meanings given for $R^{20}$, wherein $R^{20}$ is defined as in claim 1 or 9; and n and p independently of one another represent the values 0, 1, or 2, and p also denotes the value 3.

22. The compound according to claim 21, wherein Z denotes a single bond;

$L^1$ denotes fluorine, chlorine, bromine, cyano, $C_{1-3}$-alkyl, $C_{1-3}$-alkoxy, $C_{1-4}$-alkoxycarbonyl, trifluoromethyl, trifluoromethoxy, or nitro, particularly $C_{1-3}$-alkyl;

$L^2$ denotes fluorine, chlorine, bromine, CN, amino, $CF_3$, methoxy, or $C_{1-3}$-alkyl;

n denotes 0 or 1;

$L^3$ are selected independently of one another from the meanings fluorine, chlorine, bromine, cyano, nitro, $C_{1-4}$-alkyl, hydroxy, ω-hydroxy-$C_{1-3}$-alkyl, $C_{1-4}$-alkoxy, trifluoromethyl, trifluoromethoxy, $C_{2-4}$-alkynyl, carboxy, $C_{1-4}$-alkoxycarbonyl, ω-($C_{1-4}$-alkoxy)-$C_{1-3}$-alkyl, $C_{1-4}$-alkoxy-carbonylamino, amino, $C_{1-4}$-alkyl-amino, di-($C_{1-4}$-alkyl)-amino, cyclo-$C_{3-6}$-alkyleneimino, aminocarbonyl, $C_{1-4}$-alkyl-aminocarbonyl, or di-($C_{1-4}$-alkyl)-aminocarbonyl, particularly preferred are fluorine, chlorine, bromine, cyano, $CF_3$, $C_{1-3}$-alkyl, $C_{1-4}$-alkoxy, and trifluoromethoxy, with the proviso that a phenyl ring may only be monosubstituted by nitro; and p denotes 0, 1, 2, or 3.

23. A physiologically acceptable salt of the compound according to claim 21.

24. A pharmaceutical formulation comprising the compound according to claim 21 and one or more physiologically acceptable excipients or inert carriers or diluents.

25. A pharmaceutical formulation comprising the physiologically acceptable salt according to claim 23 and one or more physiologically acceptable excipients or inert carriers or diluents.

26. The pharmaceutical formulation according to claim 24 further comprising a second active substance selected from the group consisting of active substances for the treatment of diabetes, active substances for the treatment of diabetic complications, active substances for the treatment of obesity, active substances for the treatment of high blood pressure, active substances for the treatment of hyperlipidemia or arteriosclerosis, active substances for the treatment of arthritis, active substances for the treatment of anxiety states, and active substances for the treatment of depression.

27. The pharmaceutical formulation according to claim 25 further comprising a second active substance selected from the group consisting of active substances for the treatment of diabetes, active substances for the treatment of diabetic complications, active substances for the treatment of obesity, active substances for the treatment of high blood pressure, active substances for the treatment of hyperlipidemia or arteriosclerosis, active substances for the treatment of arthritis, active substances for the treatment of anxiety states, and active substances for the treatment of depression.

* * * * *